(12) United States Patent
Boese

(10) Patent No.: US 12,016,736 B2
(45) Date of Patent: Jun. 25, 2024

(54) CALIBRATION OF 2D IMAGES FOR DIGITAL TEMPLATING USING MONOMARKER

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventor: Christoph K. Boese, Hamburg (DE)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 399 days.

(21) Appl. No.: 17/524,349

(22) Filed: Nov. 11, 2021

(65) Prior Publication Data

US 2023/0149114 A1    May 18, 2023

(51) Int. Cl.
*A61B 90/00* (2016.01)
*A61B 34/10* (2016.01)
*G06T 7/80* (2017.01)

(52) U.S. Cl.
CPC .............. *A61B 90/36* (2016.02); *A61B 34/10* (2016.02); *G06T 7/80* (2017.01); *A61B 2034/105* (2016.02); *A61B 2090/363* (2016.02); *A61B 2090/367* (2016.02); *G06T 2207/30008* (2013.01)

(58) Field of Classification Search
CPC ... A61B 90/36; A61B 34/10; A61B 2034/105; A61B 2090/363; A61B 2090/367; G06T 7/80; A06T 2207/30008

USPC ........................................................ 382/128
See application file for complete search history.

(56) References Cited

U.S. PATENT DOCUMENTS

| | | | |
|---|---|---|---|
| 9,514,533 B2* | 12/2016 | Chabanas | G06T 17/30 |
| 10,813,715 B1* | 10/2020 | Chojnowski | G06F 3/0304 |
| 11,348,257 B2* | 5/2022 | Lang | A61B 90/13 |
| 11,553,969 B1* | 1/2023 | Lang | G06T 7/0012 |
| 11,786,232 B1* | 10/2023 | McCandless | A61B 17/025 |
| | | | 606/90 |
| 11,786,313 B1* | 10/2023 | Roh | A61B 34/30 |
| | | | 700/250 |
| 2004/0087852 A1* | 5/2004 | Chen | A61B 6/547 |
| | | | 600/407 |
| 2006/0189864 A1* | 8/2006 | Paradis | A61B 6/505 |
| | | | 600/407 |

(Continued)

*Primary Examiner* — William D Titcomb
(74) *Attorney, Agent, or Firm* — DLA Piper LLP

(57) ABSTRACT

A method of calibrating a frontal 2D image of a pelvis of a patient is disclosed. Frontal and lateral 2D images are received, where a fiducial marker is positioned on the patient's suprapubic region during image capture. A first distance of the fiducial marker from the imaging detector is determined based on the fiducial marker's measured diameter in the frontal image. A second distance of the fiducial marker from a coronal plane of the pelvis is determined based on the fiducial marker's measured diameter in the lateral image. The second distance is corrected based on a rotational offset of the patient in the lateral image. A third distance of the coronal plane from the imaging detector in the frontal image is determined from the first distance and corrected second distance. A calibration factor for the frontal image is calculated from the third distance and used to scale the frontal image.

21 Claims, 32 Drawing Sheets

(56) References Cited

U.S. PATENT DOCUMENTS

| | | | |
|---|---|---|---|
| 2008/0056433 A1* | 3/2008 | Steinle | A61B 90/36 378/4 |
| 2008/0269596 A1* | 10/2008 | Revie | A61B 90/39 705/28 |
| 2013/0304429 A1* | 11/2013 | Haimerl | A61B 34/10 703/1 |
| 2021/0093393 A1* | 4/2021 | Quist | A61B 5/4528 |
| 2021/0220054 A1* | 7/2021 | Parker | A61B 90/36 |
| 2022/0087746 A1* | 3/2022 | Lang | A61B 17/1742 |
| 2022/0370152 A1* | 11/2022 | Lavallee | A61B 6/4085 |

* cited by examiner

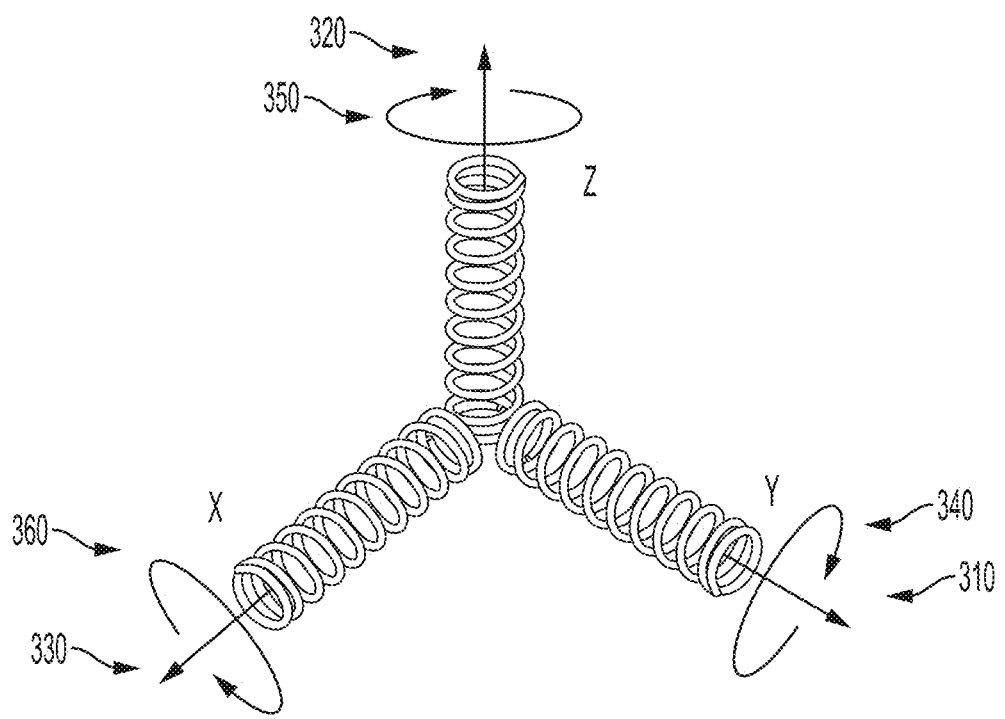
FIG. 3A
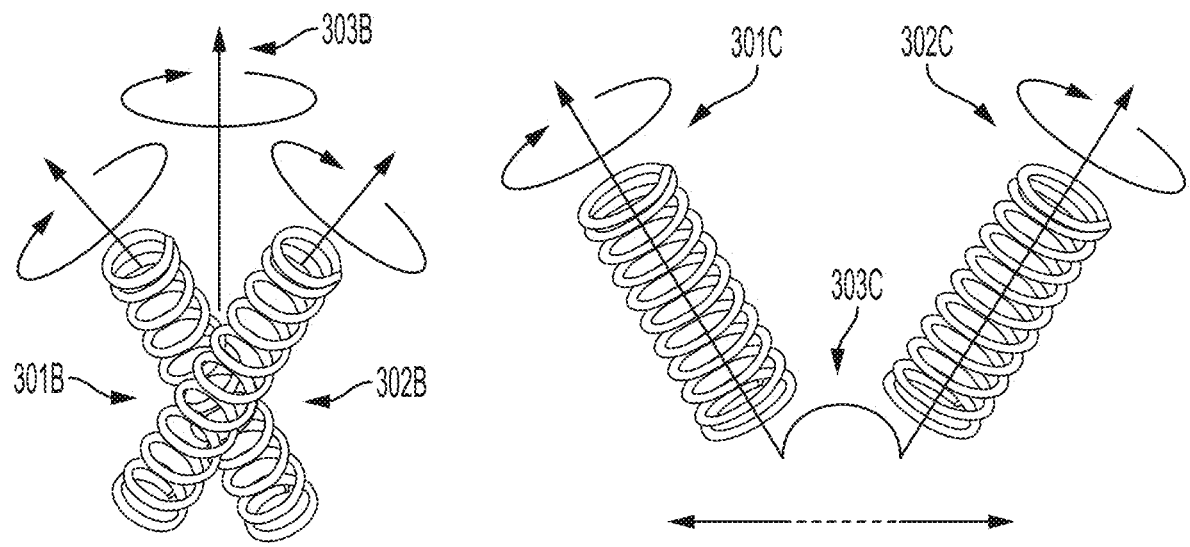
FIG. 3B
FIG. 3C

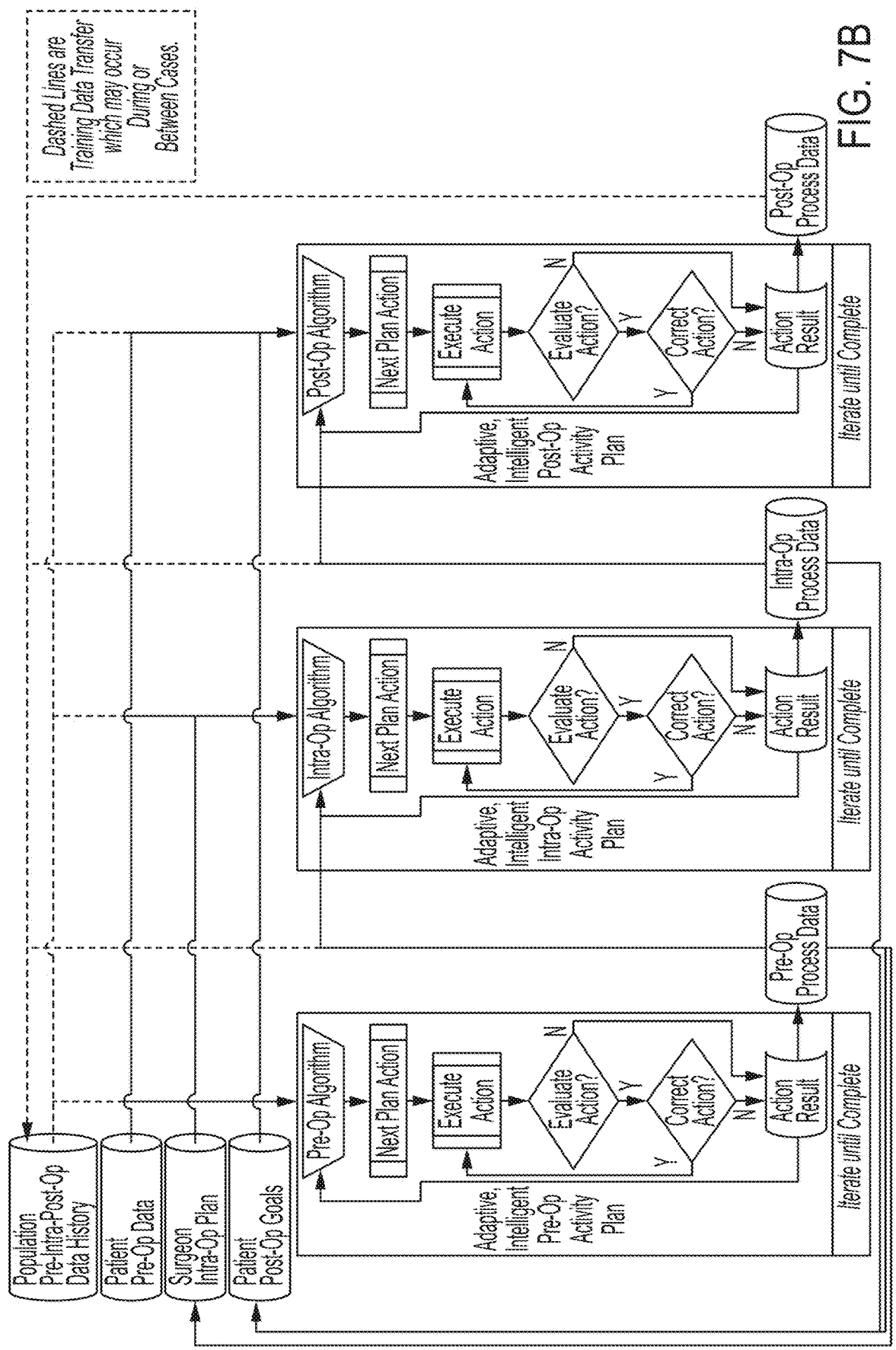

CALIBRATION OF 2D IMAGES FOR DIGITAL TEMPLATING USING MONOMARKER

TECHNICAL FIELD

The present disclosure relates generally to methods, systems, and apparatuses for pre-operative joint imaging. More particularly, the present disclosure relates to methods and systems for calibration and scaling of two-dimensional images for digital templating using a monomarker system. The disclosed techniques may be applied in advance of, for example, hip arthroplasties as well as other surgical interventions such as arthroscopic procedures, spinal procedures, maxillofacial procedures, rotator cuff procedures, ligament repair and replacement procedures.

BACKGROUND

Orthopaedic implants are used for resurfacing or replacing joints, such as hips, knees, shoulders, ankles, and elbows, that typically experience high levels of stress and wear or traumatic injury. Computer assisted systems allow a user to plan an implant procedure, such as a total hip arthroplasty (THA), or an arthroplasty of another joint, and to select or design surgical instruments based on 2D imaging. For example, X-ray images of the joint may be captured and used in digital templating software such as the VISION-AIRE system from SMITH & NEPHEW, INC. or the TRAUMACAD system from BRAINLAB, INC. to select or design a prosthetic implant.

However, when relying solely on X-ray imaging, the X-ray images must be calibrated to represent the true dimensions of the patient anatomy. Current solutions include using fiducial markers with known dimensions in the imaging field to properly scale the captured 2D images. For example, the KINGMARK calibration system from BRAIN-LAB, INC. utilizes two fiducial markers placed above and below the patient to assist in calibration of the captured 2D images.

Several difficulties may arise when using conventional systems. For example, patients may be required to lay on top of a rigid plate or other fiducial marker, which may be uncomfortable and affect the patient's pose during imaging. Further, conventional systems require precise placement of the fiducial markers by an imaging technician or other professional. Misplacement may seriously affect the accuracy of calibration. While an effective system that utilizes a single marker would be desirable for its simplicity during imaging, such systems may face issues due to the limited information received from a single marker. For example, the shape of the marker may be distorted by projectional effects in two-dimensional images. Furthermore, any variation in the location of the marker with respect to the patient may create added difficulties in assessing the image to accurately scale the image for digital templating.

As such, it would be advantageous to have a system that facilitates image calibration in supine and/or standing imaging with a single fiducial marker in a manner that corrects for distortions in the 2D image and variation of the precise fiducial marker placement during imaging.

SUMMARY

A computer-implemented method of calibrating a frontal 2D image of a pelvis of a patient positioned on an imaging surface is provided. The computer-implemented method comprises receiving a frontal 2D image of the pelvis captured by an imaging detector, wherein the frontal 2D image comprises a first representation of a fiducial marker positioned on a suprapubic region of the patient during capture; measuring a diameter of the first representation of the fiducial marker in the frontal 2D image; determining, based on the diameter of the first representation and a known diameter of the fiducial marker, a first distance of the fiducial marker from the imaging detector; receiving a lateral 2D image of the pelvis, wherein the lateral 2D image comprises a second representation of the fiducial marker positioned on the suprapubic region of the patient during capture; measuring a diameter of the second representation of the fiducial marker in the lateral 2D image; determining, based on the diameter of the second representation and the known diameter of the fiducial marker, a second distance of the fiducial marker from a coronal plane of the pelvis in the lateral 2D image; correcting the second distance based on a rotational offset of the patient in the lateral 2D image; calculating, based on the first distance and the corrected second distance, a third distance of the coronal plane from the imaging detector in the frontal 2D image; calculating, based on the third distance, a calibration factor for the frontal 2D image; scaling the frontal 2D image based on the calibration factor; and outputting the scaled frontal 2D image to a computer-readable storage device.

According to some embodiments, calculating the third distance comprises subtracting the corrected second distance from the first distance.

According to some embodiments, correcting the second distance comprises measuring a lateral offset of a center of the first representation from a central beam in the frontal 2D image; calculating an angle of the rotational offset based on the frontal 2D image and the lateral 2D image; calculating an adjustment distance based on the lateral offset and the angle; and adjusting the second distance by the adjustment distance to correct the second distance.

According to additional embodiments, calculating an angle of the rotational offset comprises determining a hip-to-hip distance in the frontal 2D image; determining a projected hip-to-hip distance in the lateral 2D image; and calculating the angle based on the hip-to-hip distance and the projected hip-to-hip distance.

According to additional embodiments, correcting the second distance further comprises determining a direction of the rotational offset based on one or more of the frontal 2D image and the lateral 2D image. According to further embodiments, determining a direction of the rotational offset comprises assessing a size of one or more features of the pelvis in the lateral 2D image. According to further embodiments, determining a direction of the rotational offset comprises identifying one or more anatomical abnormalities associated with a hip joint of the pelvis. According to further embodiments, determining a direction of the rotational offset comprises identifying one or more foreign bodies associated with a hip joint of the pelvis. According to further embodiments, determining a direction of the rotational offset comprises assessing a representation of one or more directional markers in the one or more of the frontal 2D image and the lateral 2D image, wherein the one or more directional markers are positioned on the patient during capture. According to still further embodiments, the one or more directional markers are positioned on a portion of the pelvis of the patient. According to still further embodiments, the one or more directional markers are positioned on or near an anterior superior iliac spine of the pelvis. According to still further embodiments, the one or more directional markers are coupled to the fiducial marker.

According to additional embodiments, adjusting the second distance by the adjustment distance comprises subtracting the adjustment distance from the second distance.

According to additional embodiments, adjusting the second distance by the adjustment distance comprises adding the adjustment distance to the second distance.

According to some embodiments, determining the first distance comprises measuring a lateral offset of a center of the first representation from a central beam in the frontal 2D image; and calculating the first distance based on the lateral offset, the diameter of the first representation, and the known diameter of the fiducial marker.

According to some embodiments, determining the second distance comprises measuring a lateral offset of a center of the second representation from a central beam in the lateral 2D image; and calculating the second distance based on the lateral offset, the diameter of the second representation, and the known diameter of the fiducial marker.

According to some embodiments, the frontal 2D image is an anterior-posterior 2D image of the hip joint of the patient.

A system for calibration of a 2D image of a hip of a patient is also provided. The system comprises a calibration device comprising a belt configured to be positioned about a waist of the patient, and a single fiducial marker coupled to the belt, where the single fiducial marker is configured to be positioned on the suprapubic region of the patient; at least one processor; and a non-transitory, computer-readable medium storing instructions that, when executed, cause the at least one processor to receive a frontal 2D image of the pelvis captured by an imaging detector, wherein the frontal 2D image comprises a first representation of a fiducial marker positioned on a suprapubic region of the patient during capture; measure a diameter of the first representation of the fiducial marker in the frontal 2D image; determine, based on the diameter of the first representation and a known diameter of the fiducial marker, a first distance of the fiducial marker from the imaging detector; receive a lateral 2D image of the pelvis, wherein the lateral 2D image comprises a second representation of the fiducial marker positioned on the suprapubic region of the patient during capture; measure a diameter of the second representation of the fiducial marker in the lateral 2D image; determine, based on the diameter of the second representation and the known diameter of the fiducial marker, a second distance of the fiducial marker from a coronal plane of the pelvis in the lateral 2D image; correct the second distance based on a rotational offset of the patient in the lateral 2D image; calculate, based on the first distance and the corrected second distance, a third distance of the coronal plane from the imaging detector in the frontal 2D image; calculate, based on the third distance, a calibration factor for the frontal 2D image; scale the frontal 2D image based on the calibration factor; and output the scaled frontal 2D image to a computer-readable storage device.

According to some embodiments, the instructions that cause the at least one processor to correct the second distance comprise instructions that, when executed, cause the at least one processor to measure a lateral offset of a center of the first representation from a central beam in the frontal 2D image; calculate an angle of the rotational offset based on the frontal 2D image and the lateral 2D image; calculate an adjustment distance based on the lateral offset and the angle; and adjust the second distance by the adjustment distance to correct the second distance. According to additional embodiments, the instructions that cause the at least one processor to calculate an angle of the rotational offset comprise instructions that, when executed, cause the at least one processor to determine a hip-to-hip distance in the frontal 2D image; determine a projected hip-to-hip distance in the lateral 2D image; and calculate the angle based on the hip-to-hip distance and the projected hip-to-hip distance. According to additional embodiments, the instructions that cause the at least one processor to correct the second distance further comprise instructions that, when executed, cause the at least one processor to determine a direction of the rotational offset based on one or more of the frontal 2D image and the lateral 2D image.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings:

FIG. 3A depicts an alternative example of an electromagnetic sensor device, with three perpendicular coils, according to some embodiments.

FIG. 3B depicts an alternative example of an electromagnetic sensor device, with two nonparallel, affixed coils, according to some embodiments.

FIG. 3C depicts an alternative example of an electromagnetic sensor device, with two nonparallel, separate coils, according to some embodiments.

FIG. 7B depicts an illustrative flow diagram for determining an episode of care including pre-operative, intraoperative, and post-operative actions in accordance with an embodiment.

DETAILED DESCRIPTION

This disclosure is not limited to the particular systems, devices and methods described, as these may vary. The terminology used in the description is for the purpose of describing the particular versions or embodiments only and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Definitions

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon also could apply, in some embodiments to a technician or nurse.

The systems, methods, and devices disclosed herein are particularly well adapted for surgical procedures that utilize surgical navigation systems, such as the NAVIO® surgical navigation system. NAVIO is a registered trademark of BLUE BELT TECHNOLOGIES, INC. of Pittsburgh, PA, which is a subsidiary of SMITH & NEPHEW, INC. of Memphis, TN.

CASS Ecosystem Overview

Figure 1:
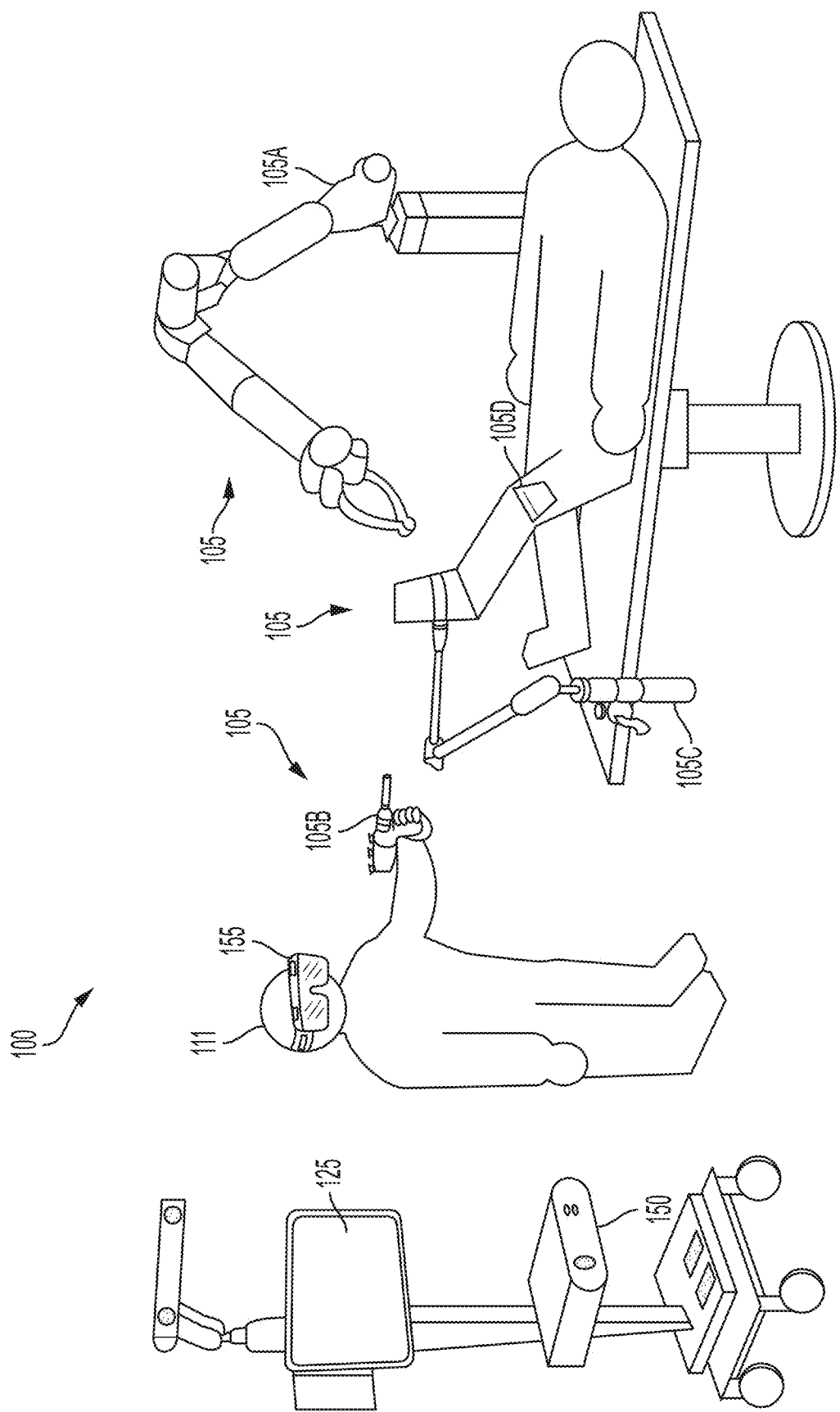
FIG. 1 depicts an operating theatre including an illustrative computer-assisted surgical system (CASS) in accordance with an embodiment.

FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a NAVIO® hand piece or a cutting guide or jig) or, alternatively, the End Effector 105B can include a device or instrument held or positioned by a Robotic Arm 105A. While one Robotic Arm 105A is illustrated in FIG. 1, in some embodiments there may be multiple devices. As examples, there may be one Robotic Arm 105A on each side of an operating table T or two devices on one side of the table T. The Robotic Arm 105A may be mounted directly to the table T, be located next to the table T on a floor platform (not shown), mounted on a floor-to-ceiling pole, or mounted on a wall or ceiling of an operating room. The floor platform may be fixed or moveable. In one particular embodiment, the robotic arm 105A is mounted on a floor-to-ceiling pole located between the patient's legs or feet. In some embodiments, the End Effector 105B may include a suture holder or a stapler to assist in closing wounds. Further, in the case of two robotic arms 105A, the surgical computer 150 can drive the robotic arms 105A to work together to suture the wound at closure. Alternatively, the surgical computer 150 can drive one or more robotic arms 105A to staple the wound at closure.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below). While one Limb Positioner 105C is illustrated in FIG. 1, in some embodiments there may be multiple devices. As examples, there may be one Limb Positioner 105C on each side of the operating table T or two devices on one side of the table T. The Limb Positioner 105C may be mounted directly to the table T, be located next to the table T on a floor platform (not shown), mounted on a pole, or mounted on a wall or ceiling of an operating room. In some embodiments, the Limb Positioner 105C can be used in non-conventional ways, such as a retractor or specific bone holder. The Limb Positioner 105C may include, as examples, an ankle boot, a soft tissue clamp, a bone clamp, or a soft-tissue retractor spoon, such as a hooked, curved, or angled blade. In some embodiments, the Limb Positioner 105C may include a suture holder to assist in closing wounds.

The Effector Platform 105 may include tools, such as a screwdriver, light or laser, to indicate an axis or plane, bubble level, pin driver, pin puller, plane checker, pointer, finger, or some combination thereof.

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, reciprocating devices (such as a rasp or broach), and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 also can include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure. In addition to positional data, data from the Tracking System 115 also can be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems. Using the data provided by the tracking system 115, the surgical computer 150 can detect objects and prevent collision. For example, the surgical computer 150 can prevent the Robotic Arm 105A and/or the End Effector 105B from colliding with soft tissue.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system. In some embodiments, the camera may be mounted on the Robotic Arm 105A.

Although, as discussed herein, the majority of tracking and/or navigation techniques utilize image-based tracking systems (e.g., IR tracking systems, video or image based tracking systems, etc.). However, electromagnetic (EM) based tracking systems are becoming more common for a variety of reasons. For example, implantation of standard optical trackers requires tissue resection (e.g., down to the cortex) as well as subsequent drilling and driving of cortical pins. Additionally, because optical trackers require a direct line of sight with a tracking system, the placement of such trackers may need to be far from the surgical site to ensure they do not restrict the movement of a surgeon or medical professional.

Figure 2:
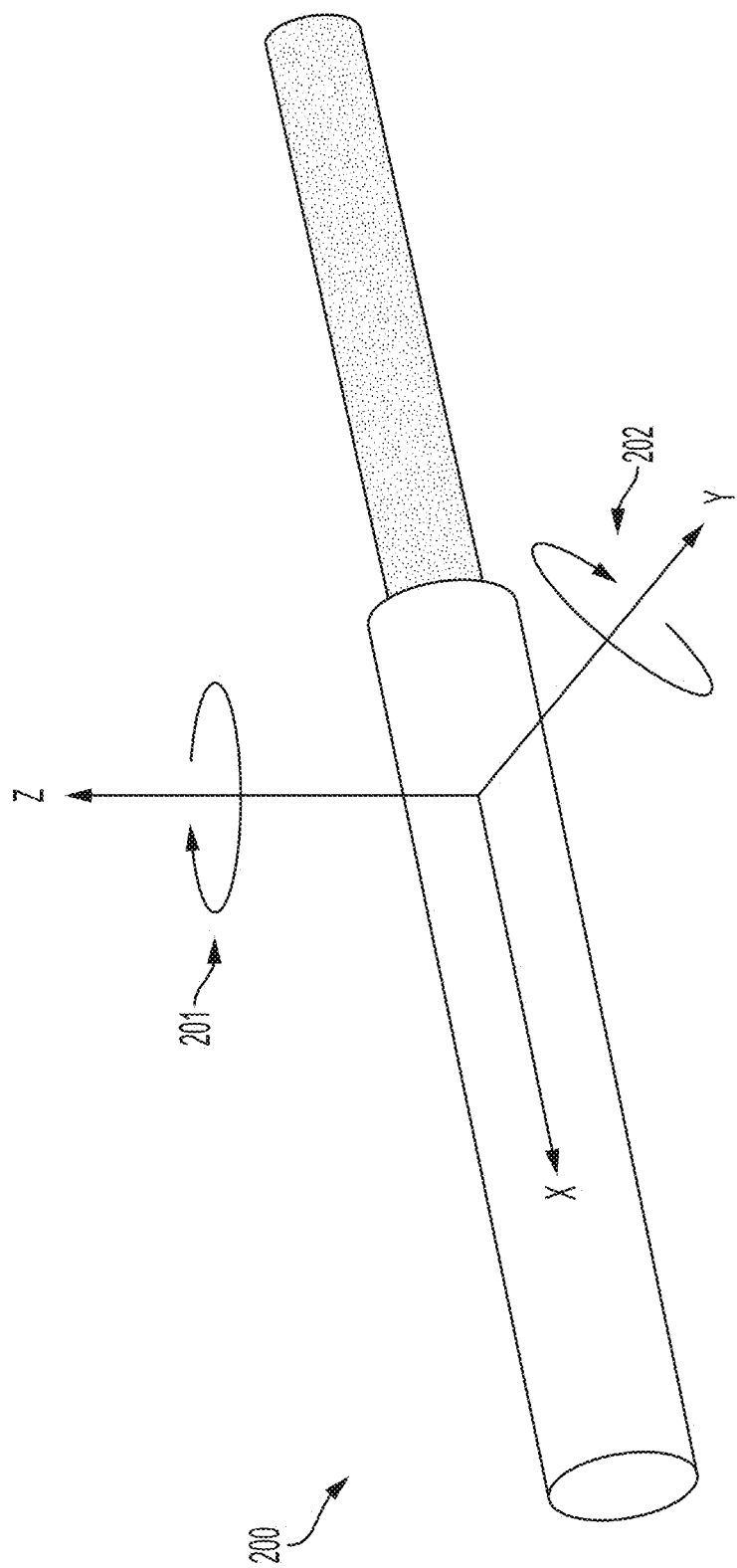
FIG. 2 depicts an example of an electromagnetic sensor device according to some embodiments.

Generally, EM based tracking devices include one or more wire coils and a reference field generator. The one or more wire coils may be energized (e.g., via a wired or wireless power supply). Once energized, the coil creates an electromagnetic field that can be detected and measured (e.g., by the reference field generator or an additional device) in a manner that allows for the location and orientation of the one or more wire coils to be determined. As should be understood by someone of ordinary skill in the art, a single coil, such as is shown in FIG. 2, is limited to detecting five (5) total degrees-of-freedom (DOF). For example, sensor 200 may be able to track/determine movement in the X, Y, or Z direction, as well as rotation around the Y-axis 202 or Z-axis 201. However, because of the electromagnetic properties of a coil, it is not possible to properly track rotational movement around the X axis.

Accordingly, in most electromagnetic tracking applications, a three coil system, such as that shown in FIG. 3A is used to enable tracking in all six degrees of freedom that are possible for a rigid body moving in a three-dimensional space (i.e., forward/backward 310, up/down 320, left/right 330, roll 340, pitch 350, and yaw 360). However, the inclusion of two additional coils and the 90° offset angles at which they are positioned may require the tracking device to be much larger. Alternatively, as one of skill in the art would know, less than three full coils may be used to track all 6DOF. In some EM based tracking devices, two coils may be affixed to each other, such as is shown in FIG. 3B. Because the two coils 301B and 302B are rigidly affixed to each other, not perfectly parallel, and have locations that are known relative to each other, it is possible to determine the sixth degree of freedom 303B with this arrangement.

Although the use of two affixed coils (e.g., 301B and 302B) allows for EM based tracking in 6DOF, the sensor device is substantially larger in diameter than a single coil because of the additional coil. Thus, the practical application of using an EM based tracking system in a surgical environment may require tissue resection and drilling of a portion of the patient bone to allow for insertion of a EM tracker. Alternatively, in some embodiments, it may be possible to implant/insert a single coil, or 5DOF EM tracking device, into a patient bone using only a pin (e.g., without the need to drill or carve out substantial bone).

Thus, as described herein, a solution is needed for which the use of an EM tracking system can be restricted to devices small enough to be inserted/embedded using a small diameter needle or pin (i.e., without the need to create a new incision or large diameter opening in the bone). Accordingly, in some embodiments, a second 5DOF sensor, which is not attached to the first, and thus has a small diameter, may be used to track all 6DOF. Referring now to FIG. 3C, in some embodiments, two 5DOF EM sensors (e.g., 301C and 302C) may be inserted into the patient (e.g., in a patient bone) at different locations and with different angular orientations (e.g., angle 303C is non-zero).

Figure 4:
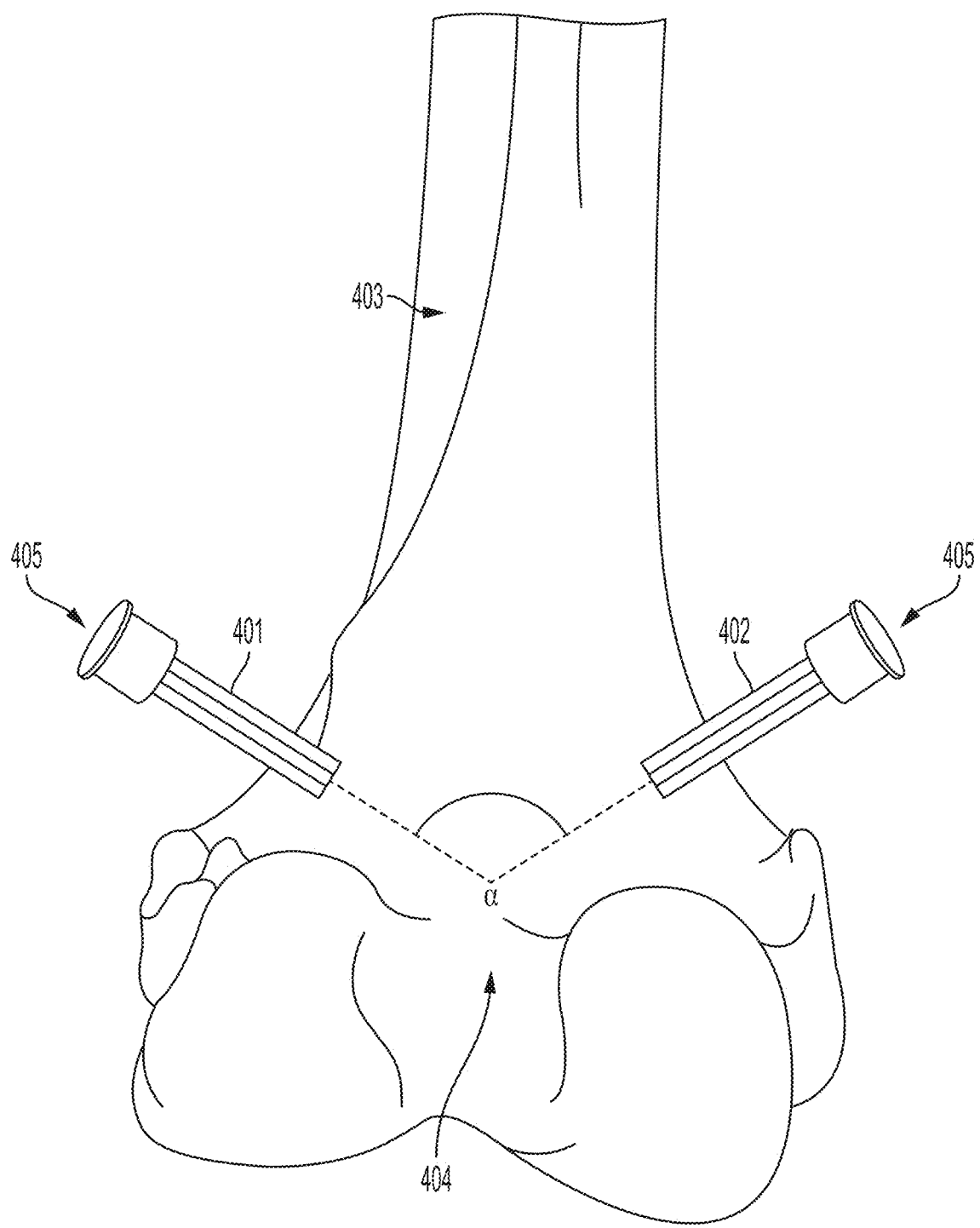
FIG. 4 depicts an example of electromagnetic sensor devices and a patient bone according to some embodiments.

Referring now to FIG. 4, an example embodiment is shown in which a first 5DOF EM sensor 401 and a second 5DOF EM sensor 402 are inserted into the patient bone 403 using a standard hollow needle 405 that is typical in most OR(s). In a further embodiment, the first sensor 401 and the second sensor 402 may have an angle offset of "α" 404. In some embodiments, it may be necessary for the offset angle "α" 404 to be greater than a predetermined value (e.g., a minimum angle of 0.50°, 0.75°, etc.). This minimum value may, in some embodiments, be determined by the CASS and provided to the surgeon or medical professional during the surgical plan. In some embodiments, a minimum value may be based on one or more factors, such as, for example, the orientation accuracy of the tracking system, a distance between the first and second EM sensors. The location of the field generator, a location of the field detector, a type of EM sensor, a quality of the EM sensor, patient anatomy, and the like.

Accordingly, as discussed herein, in some embodiments, a pin/needle (e.g., a cannulated mounting needle, etc.) may be used to insert one or more EM sensors. Generally, the pin/needle would be a disposable component, while the sensors themselves may be reusable. However, it should be understood that this is only one potential system, and that various other systems may be used in which the pin/needle and/or EM sensors are independently disposable or reusable.

In a further embodiment, the EM sensors may be affixed to the mounting needle/pin (e.g., using a luer-lock fitting or the like), which can allow for quick assembly and disassembly. In additional embodiments, the EM sensors may utilize an alternative sleeve and/or anchor system that allows for minimally invasive placement of the sensors.

In another embodiment, the above systems may allow for a multi-sensor navigation system that can detect and correct for field distortions that plague electromagnetic tracking systems. It should be understood that field distortions may result from movement of any ferromagnetic materials within the reference field. Thus, as one of ordinary skill in the art would know, a typical OR has a large number of devices (e.g., an operating table, LCD displays, lighting equipment, imaging systems, surgical instruments, etc.) that may cause interference. Furthermore, field distortions are notoriously difficult to detect. The use of multiple EM sensors enables the system to detect field distortions accurately, and/or to warn a user that the current position measurements may not be accurate. Because the sensors are rigidly fixed to the bony anatomy (e.g., via the pin/needle), relative measurement of sensor positions (X, Y, Z) may be used to detect field distortions. By way of non-limiting example, in some embodiments, after the EM sensors are fixed to the bone, the relative distance between the two sensors is known and should remain constant. Thus, any change in this distance could indicate the presence of a field distortion.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they also can be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient also can involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process also can include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Powered Impaction and Acetabular Reamer Devices

Part of the flexibility of the CASS design described above with respect to FIG. 1 is that additional or alternative devices can be added to the CASS 100 as necessary to support particular surgical procedures. For example, in the context of hip surgeries, the CASS 100 may include a powered impaction device. Impaction devices are designed to repeatedly apply an impaction force that the surgeon can use to perform activities such as implant alignment. For example, within a total hip arthroplasty (THA), a surgeon will often insert a prosthetic acetabular cup into the implant host's acetabulum using an impaction device. Although impaction devices can be manual in nature (e.g., operated by the surgeon striking an impactor with a mallet), powered impaction devices are generally easier and quicker to use in the surgical setting. Powered impaction devices may be powered, for example, using a battery attached to the device. Various attachment pieces may be connected to the powered impaction device to allow the impaction force to be directed in various ways as needed during surgery. Also, in the context of hip surgeries, the CASS 100 may include a powered, robotically controlled end effector to ream the acetabulum to accommodate an acetabular cup implant.

In a robotically-assisted THA, the patient's anatomy can be registered to the CASS 100 using CT or other image data, the identification of anatomical landmarks, tracker arrays attached to the patient's bones, and one or more cameras. Tracker arrays can be mounted on the iliac crest using clamps and/or bone pins and such trackers can be mounted externally through the skin or internally (either posterolaterally or anterolaterally) through the incision made to perform the THA. For a THA, the CASS 100 can utilize one or more femoral cortical screws inserted into the proximal femur as checkpoints to aid in the registration process. The CASS 100 also can utilize one or more checkpoint screws inserted into the pelvis as additional checkpoints to aid in the registration process. Femoral tracker arrays can be secured to or mounted in the femoral cortical screws. The CASS 100 can employ steps where the registration is verified using a probe that the surgeon precisely places on key areas of the proximal femur and pelvis identified for the surgeon on the display 125. Trackers can be located on the robotic arm 105A or end effector 105B to register the arm and/or end effector to the CASS 100. The verification step also can utilize proximal and distal femoral checkpoints. The CASS 100 can utilize color prompts or other prompts to inform the surgeon that the registration process for the relevant bones and the robotic arm 105A or end effector 105B has been verified to a certain degree of accuracy (e.g., within 1 mm).

For a THA, the CASS 100 can include a broach tracking option using femoral arrays to allow the surgeon to intraoperatively capture the broach position and orientation and calculate hip length and offset values for the patient. Based on information provided about the patient's hip joint and the planned implant position and orientation after broach tracking is completed, the surgeon can make modifications or adjustments to the surgical plan.

For a robotically-assisted THA, the CASS 100 can include one or more powered reamers connected or attached to a robotic arm 105A or end effector 105B that prepares the pelvic bone to receive an acetabular implant according to a surgical plan. The robotic arm 105A and/or end effector 105B can inform the surgeon and/or control the power of the reamer to ensure that the acetabulum is being resected (reamed) in accordance with the surgical plan. For example, if the surgeon attempts to resect bone outside of the boundary of the bone to be resected in accordance with the surgical plan, the CASS 100 can power off the reamer or instruct the surgeon to power off the reamer. The CASS 100 can provide the surgeon with an option to turn off or disengage the robotic control of the reamer. The display 125 can depict the progress of the bone being resected (reamed) as compared to the surgical plan using different colors. The surgeon can view the display of the bone being resected (reamed) to guide the reamer to complete the reaming in accordance with the surgical plan. The CASS 100 can provide visual or audible prompts to the surgeon to warn the surgeon that resections are being made that are not in accordance with the surgical plan.

Following reaming, the CASS 100 can employ a manual or powered impactor that is attached or connected to the robotic arm 105A or end effector 105B to impact trial implants and final implants into the acetabulum. The robotic arm 105A and/or end effector 105B can be used to guide the impactor to impact the trial and final implants into the acetabulum in accordance with the surgical plan. The CASS 100 can cause the position and orientation of the trial and final implants vis-à-vis the bone to be displayed to inform the surgeon as to how the trial and final implant's orientation and position compare to the surgical plan, and the display 125 can show the implant's position and orientation as the surgeon manipulates the leg and hip. The CASS 100 can provide the surgeon with the option of re-planning and re-doing the reaming and implant impaction by preparing a new surgical plan if the surgeon is not satisfied with the original implant position and orientation.

Preoperatively, the CASS 100 can develop a proposed surgical plan based on a three dimensional model of the hip joint and other information specific to the patient, such as the mechanical and anatomical axes of the leg bones, the epicondylar axis, the femoral neck axis, the dimensions (e.g., length) of the femur and hip, the midline axis of the hip joint, the ASIS axis of the hip joint, and the location of anatomical landmarks such as the lesser trochanter landmarks, the distal landmark, and the center of rotation of the hip joint. The CASS-developed surgical plan can provide a recommended optimal implant size and implant position and orientation based on the three dimensional model of the hip joint and other information specific to the patient. The CASS-developed surgical plan can include proposed details on offset values, inclination and anteversion values, center of rotation, cup size, medialization values, superior-inferior fit values, femoral stem sizing and length.

For a THA, the CASS-developed surgical plan can be viewed preoperatively and intraoperatively, and the surgeon can modify CASS-developed surgical plan preoperatively or intraoperatively. The CASS-developed surgical plan can display the planned resection to the hip joint and superimpose the planned implants onto the hip joint based on the planned resections. The CASS 100 can provide the surgeon with options for different surgical workflows that will be displayed to the surgeon based on a surgeon's preference. For example, the surgeon can choose from different workflows based on the number and types of anatomical landmarks that are checked and captured and/or the location and number of tracker arrays used in the registration process.

According to some embodiments, a powered impaction device used with the CASS 100 may operate with a variety of different settings. In some embodiments, the surgeon adjusts settings through a manual switch or other physical mechanism on the powered impaction device. In other embodiments, a digital interface may be used that allows setting entry, for example, via a touchscreen on the powered impaction device. Such a digital interface may allow the available settings to vary based, for example, on the type of attachment piece connected to the power attachment device. In some embodiments, rather than adjusting the settings on the powered impaction device itself, the settings can be changed through communication with a robot or other computer system within the CASS 100. Such connections may be established using, for example, a Bluetooth or Wi-Fi networking module on the powered impaction device. In another embodiment, the impaction device and end pieces may contain features that allow the impaction device to be aware of what end piece (cup impactor, broach handle, etc.) is attached with no action required by the surgeon, and adjust the settings accordingly. This may be achieved, for example, through a QR code, barcode, RFID tag, or other method.

Examples of the settings that may be used include cup impaction settings (e.g., single direction, specified frequency range, specified force and/or energy range); broach impaction settings (e.g., dual direction/oscillating at a specified frequency range, specified force and/or energy range); femoral head impaction settings (e.g., single direction/single blow at a specified force or energy); and stem impaction settings (e.g., single direction at specified frequency with a specified force or energy). Additionally, in some embodiments, the powered impaction device includes settings related to acetabular liner impaction (e.g., single direction/single blow at a specified force or energy). There may be a plurality of settings for each type of liner such as poly, ceramic, oxinium, or other materials. Furthermore, the powered impaction device may offer settings for different bone quality based on preoperative testing/imaging/knowledge and/or intraoperative assessment by surgeon. In some embodiments, the powered impactor device may have a dual function. For example, the powered impactor device not only could provide reciprocating motion to provide an impact force, but also could provide reciprocating motion for a broach or rasp.

In some embodiments, the powered impaction device includes feedback sensors that gather data during instrument use and send data to a computing device, such as a controller within the device or the Surgical Computer 150. This computing device can then record the data for later analysis and use. Examples of the data that may be collected include, without limitation, sound waves, the predetermined resonance frequency of each instrument, reaction force or rebound energy from patient bone, location of the device with respect to imaging (e.g., fluoro, CT, ultrasound, MRI, etc.) registered bony anatomy, and/or external strain gauges on bones.

Once the data is collected, the computing device may execute one or more algorithms in real-time or near real-time to aid the surgeon in performing the surgical procedure. For example, in some embodiments, the computing device uses the collected data to derive information such as the proper final broach size (femur); when the stem is fully seated (femur side); or when the cup is seated (depth and/or orientation) for a THA. Once the information is known, it may be displayed for the surgeon's review, or it may be used to activate haptics or other feedback mechanisms to guide the surgical procedure.

Additionally, the data derived from the aforementioned algorithms may be used to drive operation of the device. For example, during insertion of a prosthetic acetabular cup with a powered impaction device, the device may automatically extend an impaction head (e.g., an end effector) moving the implant into the proper location, or turn the power off to the device once the implant is fully seated. In one embodiment, the derived information may be used to automatically adjust settings for quality of bone where the powered impaction device should use less power to mitigate femoral/acetabular/pelvic fracture or damage to surrounding tissues.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 also can place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

The examples below describe uses of the robotic device in the context of a hip surgery; however, it should be understood that the robotic arm may have other applications for surgical procedures involving knees, shoulders, etc. One example of use of a robotic arm in the context of forming an anterior cruciate ligament (ACL) graft tunnel is described in WIPO Publication No. WO 2020/047051, filed Aug. 28, 2019, entitled "Robotic Assisted Ligament Graft Placement and Tensioning," the entirety of which is incorporated herein by reference.

A robotic arm 105A may be used for holding the retractor. For example in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

The robotic arm 105A may be a passive arm. As an example, the robotic arm 105A may be a CIRQ robot arm available from Brainlab AG. CIRQ is a registered trademark of Brainlab AG, Olof-Palme-Str. 9 81829, Munchen, FED REP of GERMANY. In one particular embodiment, the robotic arm 105A is an intelligent holding arm as disclosed in U.S. patent application Ser. No. 15/525,585 to Krinninger et al., U.S. patent application Ser. No. 15/561,042 to Nowatschin et al., U.S. patent application Ser. No. 15/561,048 to Nowatschin et al., and U.S. Pat. No. 10,342,636 to Nowatschin et al., the entire contents of each of which is herein incorporated by reference.

Surgical Procedure Data Generation and Collection

The various services that are provided by medical professionals to treat a clinical condition are collectively referred to as an "episode of care." For a particular surgical intervention the episode of care can include three phases: pre-operative, intra-operative, and post-operative. During each phase, data is collected or generated that can be used to analyze the episode of care in order to understand various features of the procedure and identify patterns that may be used, for example, in training models to make decisions with minimal human intervention. The data collected over the episode of care may be stored at the Surgical Computer 150 or the Surgical Data Server 180 as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure. In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. patent application Ser. No. 13/814,531 filed Aug. 15, 2011 and entitled "Systems and Methods for Optimizing Parameters for Orthopaedic Procedures"; U.S. patent application Ser. No. 14/232,958 filed Jul. 20, 2012 and entitled "Systems and Methods for Optimizing Fit of an Implant to Anatomy"; and U.S. patent application Ser. No. 12/234,444 filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 5C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 5A:
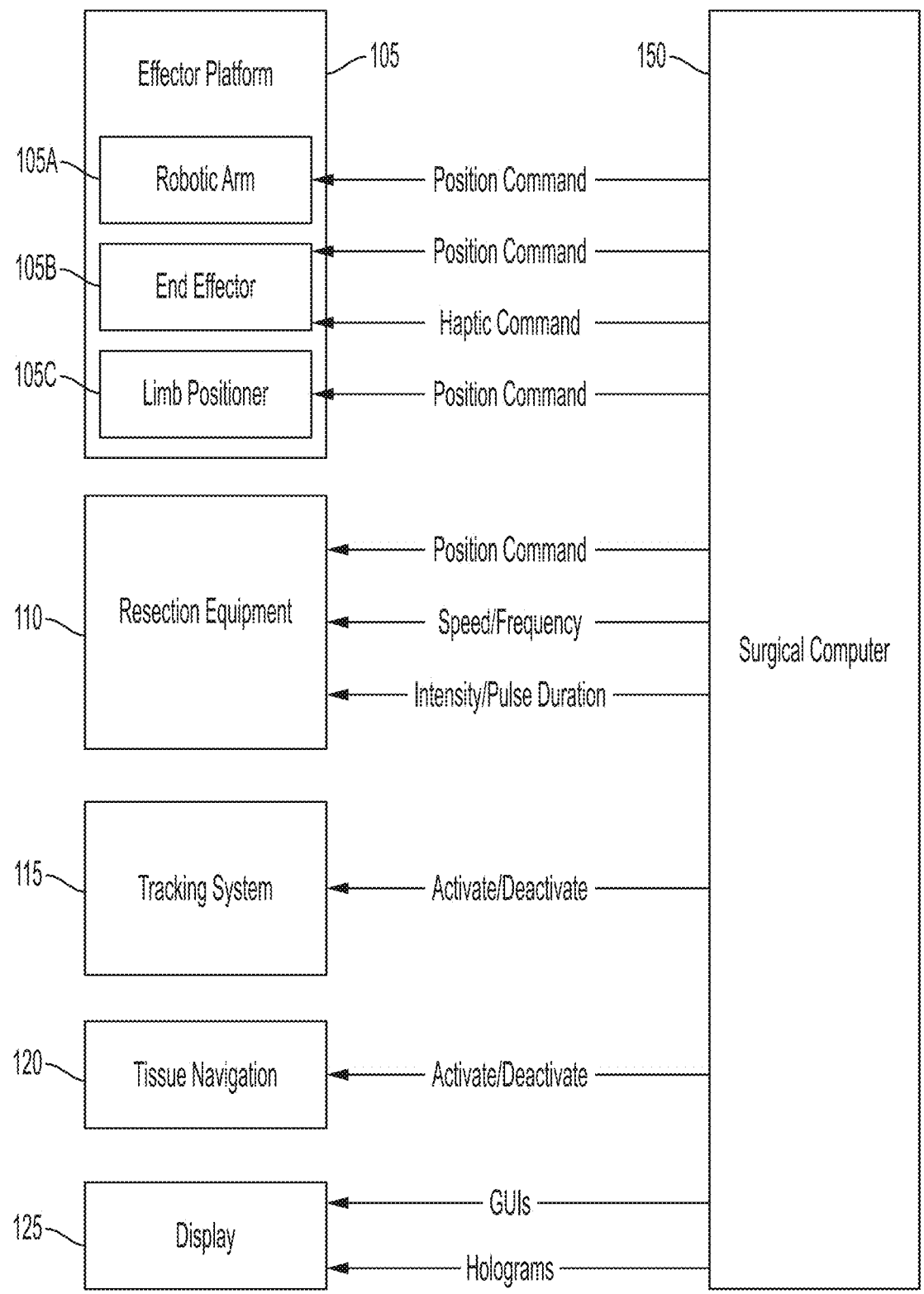
FIG. 5A depicts illustrative control instructions that a surgical computer provides to other components of a CASS in accordance with an embodiment.
Figure 5B:
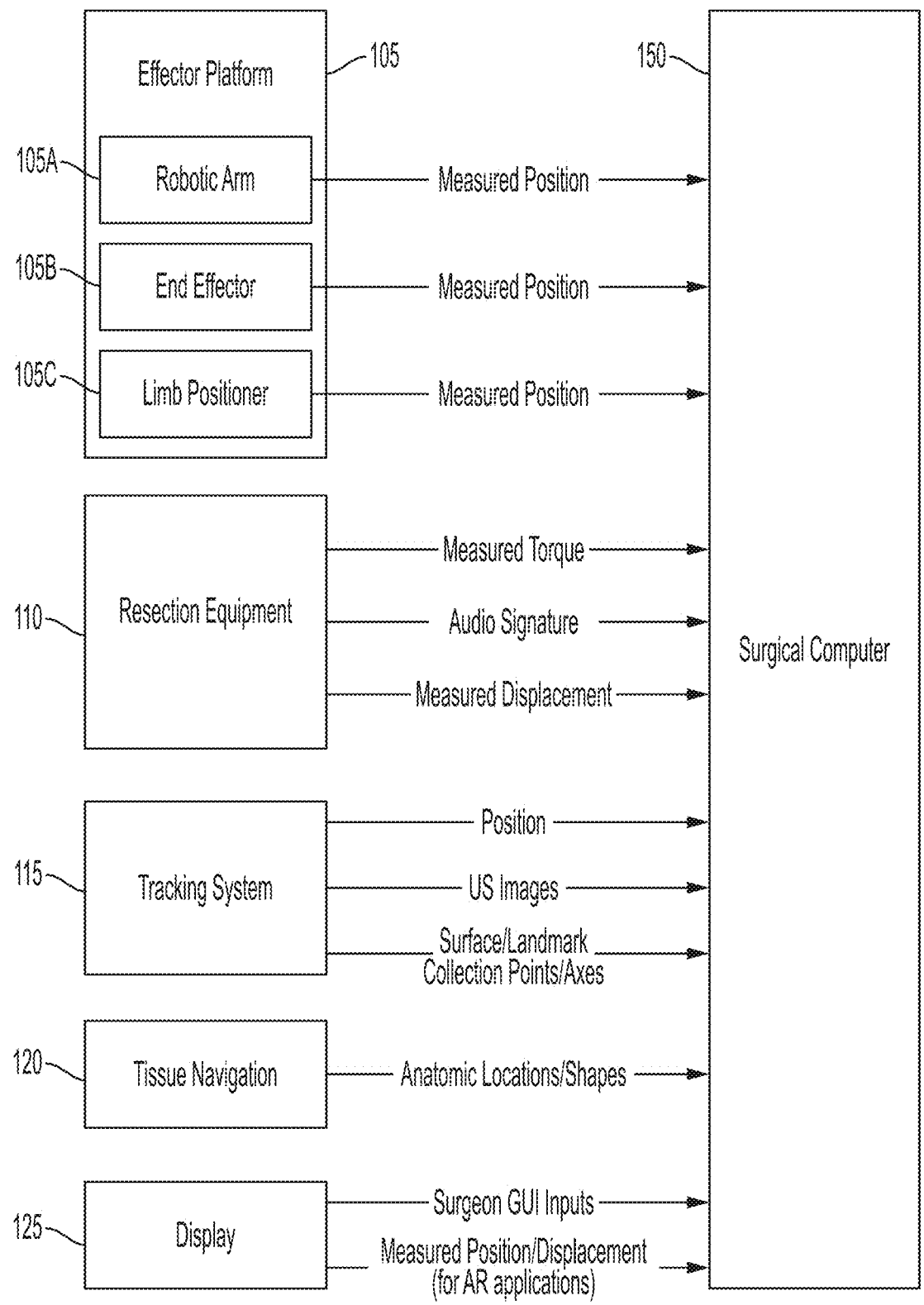
FIG. 5B depicts illustrative control instructions that components of a CASS provide to a surgical computer in accordance with an embodiment.

FIGS. 5A and 5B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 5A shows examples of some of the control instructions that the Surgical Computer 150 provides to other components of the CASS 100, according to some embodiments. Note that the example of FIG. 5A assumes that the components of the Effector Platform 105 are each controlled directly by the Surgical Computer 150. In embodiments where a component is manually controlled by the Surgeon 111, instructions may be provided on the Display 125 or AR HMD 155 instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 5A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D. In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 5A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images, GUIs, etc. using techniques known in the art. The display 125 can include various portions of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict *varus* and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 also can include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 also can provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 also can preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc. using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW, INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server 180 (see FIG. 5C). As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in WIPO Publication No. 2020/037308, filed Aug. 19, 2019, entitled "Patient Specific Surgical Method and System," the entirety of which is incorporated herein by reference.

FIG. 5B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer 150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150 (see FIG. 5B), the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc. as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

During the post-operative phase of the episode of care, various types of data can be collected to quantify the overall improvement or deterioration in the patient's condition as a result of the surgery. The data can take the form of, for example, self-reported information reported by patients via questionnaires. For example, in the context of a knee replacement surgery, functional status can be measured with an Oxford Knee Score questionnaire, and the post-operative quality of life can be measured with a EQSD-5L questionnaire. Other examples in the context of a hip replacement surgery may include the Oxford Hip Score, Harris Hip Score, and WOMAC (Western Ontario and McMaster Universities Osteoarthritis index). Such questionnaires can be administered, for example, by a healthcare professional directly in a clinical setting or using a mobile app that allows the patient to respond to questions directly. In some embodiments, the patient may be outfitted with one or more wearable devices that collect data relevant to the surgery. For example, following a knee surgery, the patient may be outfitted with a knee brace that includes sensors that monitor knee positioning, flexibility, etc. This information can be collected and transferred to the patient's mobile device for review by the surgeon to evaluate the outcome of the surgery and address any issues. In some embodiments, one or more cameras can capture and record the motion of a patient's body segments during specified activities postoperatively. This motion capture can be compared to a biomechanics model to better understand the functionality of the patient's joints and better predict progress in recovery and identify any possible revisions that may be needed.

The post-operative stage of the episode of care can continue over the entire life of a patient. For example, in some embodiments, the Surgical Computer 150 or other components comprising the CASS 100 can continue to receive and collect data relevant to a surgical procedure after the procedure has been performed. This data may include, for example, images, answers to questions, "normal" patient data (e.g., blood type, blood pressure, conditions, medications, etc.), biometric data (e.g., gait, etc.), and objective and subjective data about specific issues (e.g., knee or hip joint pain). This data may be explicitly provided to the Surgical Computer 150 or other CASS component by the patient or the patient's physician(s). Alternatively or additionally, the Surgical Computer 150 or other CASS component can monitor the patient's EMR and retrieve relevant information as it becomes available. This longitudinal view of the patient's recovery allows the Surgical Computer 150 or other CASS component to provide a more objective analysis of the patient's outcome to measure and track success or lack of success for a given procedure. For example, a condition experienced by a patient long after the surgical procedure can be linked back to the surgery through a regression analysis of various data items collected during the episode of care. This analysis can be further enhanced by performing the analysis on groups of patients that had similar procedures and/or have similar anatomies.

In some embodiments, data is collected at a central location to provide for easier analysis and use. Data can be manually collected from various CASS components in some instances. For example, a portable storage device (e.g., USB stick) can be attached to the Surgical Computer 150 into order to retrieve data collected during surgery. The data can then be transferred, for example, via a desktop computer to the centralized storage. Alternatively, in some embodiments, the Surgical Computer 150 is connected directly to the centralized storage via a Network 175 as shown in FIG. 5C.

Figure 5C:
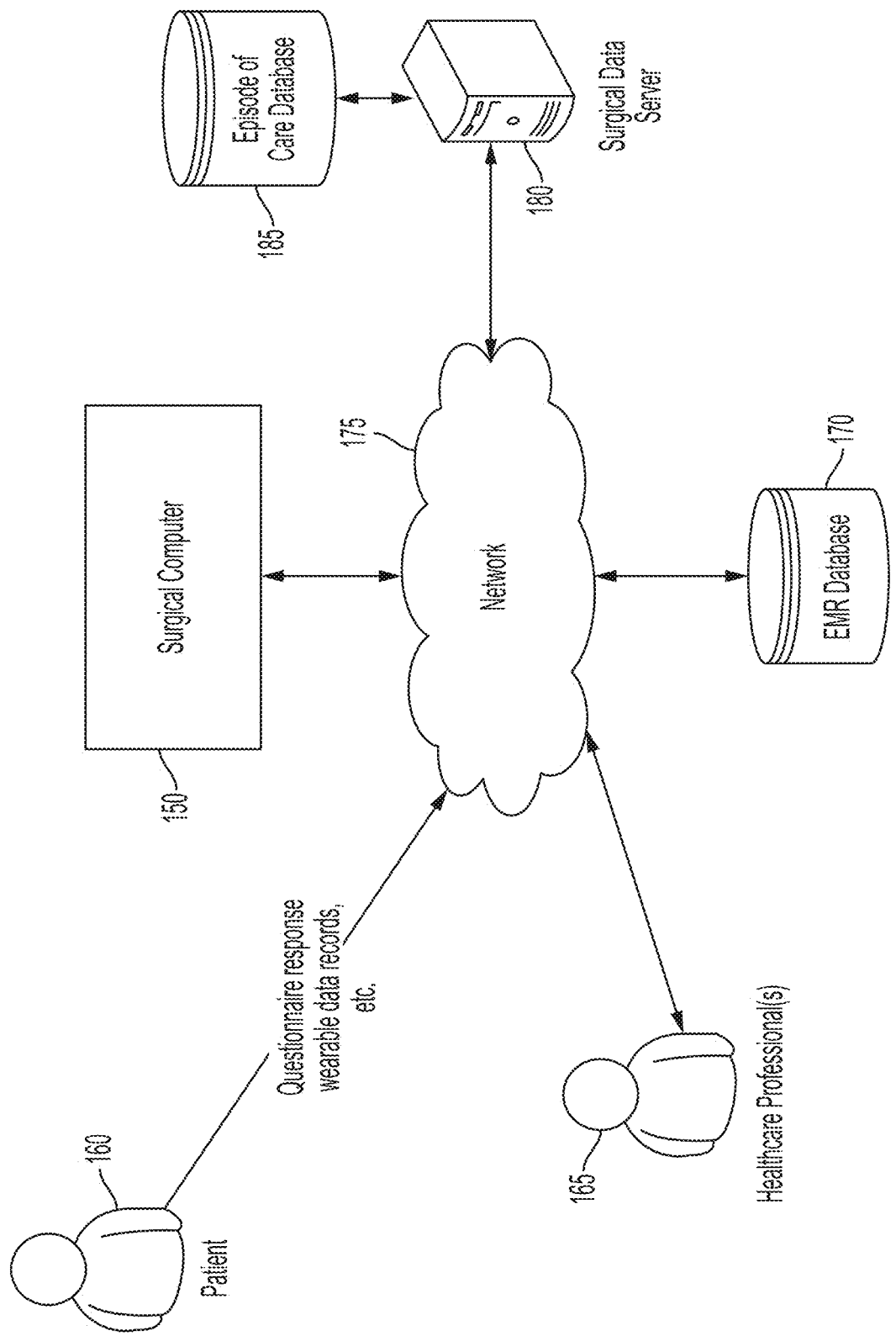
FIG. 5C depicts an illustrative implementation in which a surgical computer is connected to a surgical data server via a network in accordance with an embodiment.

FIG. 5C illustrates a "cloud-based" implementation in which the Surgical Computer 150 is connected to a Surgical Data Server 180 via a Network 175. This Network 175 may be, for example, a private intranet or the Internet. In addition to the data from the Surgical Computer 150, other sources can transfer relevant data to the Surgical Data Server 180. The example of FIG. 5C shows 3 additional data sources: the Patient 160, Healthcare Professional(s) 165, and an EMR Database 170. Thus, the Patient 160 can send pre-operative and post-operative data to the Surgical Data Server 180, for example, using a mobile app. The Healthcare Professional(s) 165 includes the surgeon and his or her staff as well as any other professionals working with Patient 160 (e.g., a personal physician, a rehabilitation specialist, etc.). It should also be noted that the EMR Database 170 may be used for both pre-operative and post-operative data. For example, assuming that the Patient 160 has given adequate permissions, the Surgical Data Server 180 may collect the EMR of the Patient pre-surgery. Then, the Surgical Data Server 180 may continue to monitor the EMR for any updates post-surgery.

At the Surgical Data Server 180, an Episode of Care Database 185 is used to store the various data collected over a patient's episode of care. The Episode of Care Database 185 may be implemented using any technique known in the art. For example, in some embodiments, a SQL-based database may be used where all of the various data items are structured in a manner that allows them to be readily incorporated in two SQL's collection of rows and columns. However, in other embodiments a No-SQL database may be employed to allow for unstructured data, while providing the ability to rapidly process and respond to queries. As is understood in the art, the term "No-SQL" is used to define a class of data stores that are non-relational in their design. Various types of No-SQL databases may generally be grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of No-SQL database may be used to implement the various embodiments described herein and, in some embodiments, the different types of databases may support the Episode of Care Database 185.

Data can be transferred between the various data sources and the Surgical Data Server 180 using any data format and transfer technique known in the art. It should be noted that the architecture shown in FIG. 5C allows transmission from the data source to the Surgical Data Server 180, as well as retrieval of data from the Surgical Data Server 180 by the data sources. For example, as explained in detail below, in some embodiments, the Surgical Computer 150 may use data from past surgeries, machine learning models, etc. to help guide the surgical procedure.

In some embodiments, the Surgical Computer 150 or the Surgical Data Server 180 may execute a de-identification process to ensure that data stored in the Episode of Care Database 185 meets Health Insurance Portability and Accountability Act (HIPAA) standards or other requirements mandated by law. HIPAA provides a list of certain identifiers that must be removed from data during de-identification. The aforementioned de-identification process can scan for these identifiers in data that is transferred to the Episode of Care Database 185 for storage. For example, in one embodiment, the Surgical Computer 150 executes the de-identification process just prior to initiating transfer of a particular data item or set of data items to the Surgical Data Server 180. In some embodiments, a unique identifier is assigned to data from a particular episode of care to allow for re-identification of the data if necessary.

Although FIGS. 5A-5C discuss data collection in the context of a single episode of care, it should be understood that the general concept can be extended to data collection from multiple episodes of care. For example, surgical data may be collected over an entire episode of care each time a surgery is performed with the CASS 100 and stored at the Surgical Computer 150 or at the Surgical Data Server 180. As explained in further detail below, a robust database of episode of care data allows the generation of optimized values, measurements, distances, or other parameters and other recommendations related to the surgical procedure. In some embodiments, the various datasets are indexed in the database or other storage medium in a manner that allows for rapid retrieval of relevant information during the surgical procedure. For example, in one embodiment, a patient-centric set of indices may be used so that data pertaining to a particular patient or a set of patients similar to a particular patient can be readily extracted. This concept can be similarly applied to surgeons, implant characteristics, CASS component versions, etc.

Further details of the management of episode of care data is described in U.S. Patent Application No. 62/783,858 filed Dec. 21, 2018 and entitled "Methods and Systems for Providing an Episode of Care," the entirety of which is incorporated herein by reference.

Open Versus Closed Digital Ecosystems

In some embodiments, the CASS 100 is designed to operate as a self-contained or "closed" digital ecosystem. Each component of the CASS 100 is specifically designed to be used in the closed ecosystem, and data is generally not accessible to devices outside of the digital ecosystem. For example, in some embodiments, each component includes software or firmware that implements proprietary protocols for activities such as communication, storage, security, etc. The concept of a closed digital ecosystem may be desirable for a company that wants to control all components of the CASS 100 to ensure that certain compatibility, security, and reliability standards are met. For example, the CASS 100 can be designed such that a new component cannot be used with the CASS unless it is certified by the company.

In other embodiments, the CASS 100 is designed to operate as an "open" digital ecosystem. In these embodiments, components may be produced by a variety of different companies according to standards for activities, such as communication, storage, and security. Thus, by using these standards, any company can freely build an independent, compliant component of the CASS platform. Data may be transferred between components using publicly available application programming interfaces (APIs) and open, shareable data formats.

To illustrate one type of recommendation that may be performed with the CASS 100, a technique for optimizing surgical parameters is disclosed below. The term "optimization" in this context means selection of parameters that are optimal based on certain specified criteria. In an extreme case, optimization can refer to selecting optimal parameter(s) based on data from the entire episode of care, including any pre-operative data, the state of CASS data at a given point in time, and post-operative goals. Moreover, optimization may be performed using historical data, such as data generated during past surgeries involving, for example, the same surgeon, past patients with physical characteristics similar to the current patient, or the like.

The optimized parameters may depend on the portion of the patient's anatomy to be operated on. For example, for knee surgeries, the surgical parameters may include positioning information for the femoral and tibial component including, without limitation, rotational alignment (e.g., varus/valgus rotation, external rotation, flexion rotation for the femoral component, posterior slope of the tibial component), resection depths (e.g., varus knee, valgus knee), and implant type, size and position. The positioning information may further include surgical parameters for the combined implant, such as overall limb alignment, combined tibiofemoral hyperextension, and combined tibiofemoral resection. Additional examples of parameters that could be optimized for a given TKA femoral implant by the CASS 100 include the following:

| Parameter | Reference | Exemplary Recommendation (s) |
|---|---|---|
| Size | Posterior | The largest sized implant that does not overhang medial/lateral bone edges or overhang the anterior femur. A size that does not result in overstuffing the patella femoral joint |
| Implant Position - Medial Lateral | Medial/lateral cortical bone edges | Center the implant evenly between the medial/lateral cortical bone edges |
| Resection Depth - Varus Knee | Distal and posterior lateral | 6 mm of bone |
| Resection Depth - Valgus Knee | Distal and posterior medial | 7 mm of bone |
| Rotation - Varus/Valgus | Mechanical Axis | 1° varus |
| Rotation - External | Transepicondylar Axis | 1° external from the transepicondylar axis |
| Rotation - Flexion | Mechanical Axis | 3° flexed |

Additional examples of parameters that could be optimized for a given TKA tibial implant by the CASS 100 include the following:

| Parameter | Reference | Exemplary Recommendation (s) |
|---|---|---|
| Size | Posterior | The largest sized implant that does not overhang the medial, lateral, anterior, and posterior tibial edges |

| Parameter | Reference | Exemplary Recommendation (s) |
| --- | --- | --- |
| Implant Position | Medial/lateral and anterior/posterior cortical bone edges | Center the implant evenly between the medial/lateral and anterior/posterior cortical bone edges |
| Resection Depth - Varus Knee | Lateral/Medial | 4 mm of bone |
| Resection Depth - Valgus Knee | Lateral/Medial | 5 mm of bone |
| Rotation - Varus/Valgus | Mechanical Axis | 1° valgus |
| Rotation - External | Tibial Anterior Posterior Axis | 1° external from the tibial anterior paxis |
| Posterior Slope | Mechanical Axis | 3° posterior slope |

For hip surgeries, the surgical parameters may comprise femoral neck resection location and angle, cup inclination angle, cup anteversion angle, cup depth, femoral stem design, femoral stem size, fit of the femoral stem within the canal, femoral offset, leg length, and femoral version of the implant.

Shoulder parameters may include, without limitation, humeral resection depth/angle, humeral stem version, humeral offset, glenoid version and inclination, as well as reverse shoulder parameters such as humeral resection depth/angle, humeral stem version, Glenoid tilt/version, glenosphere orientation, glenosphere offset and offset direction.

Various conventional techniques exist for optimizing surgical parameters. However, these techniques are typically computationally intensive and, thus, parameters often need to be determined pre-operatively. As a result, the surgeon is limited in his or her ability to make modifications to optimized parameters based on issues that may arise during surgery. Moreover, conventional optimization techniques typically operate in a "black box" manner with little or no explanation regarding recommended parameter values. Thus, if the surgeon decides to deviate from a recommended parameter value, the surgeon typically does so without a full understanding of the effect of that deviation on the rest of the surgical workflow, or the impact of the deviation on the patient's post-surgery quality of life.

Operative Patient Care System

Figure 6:
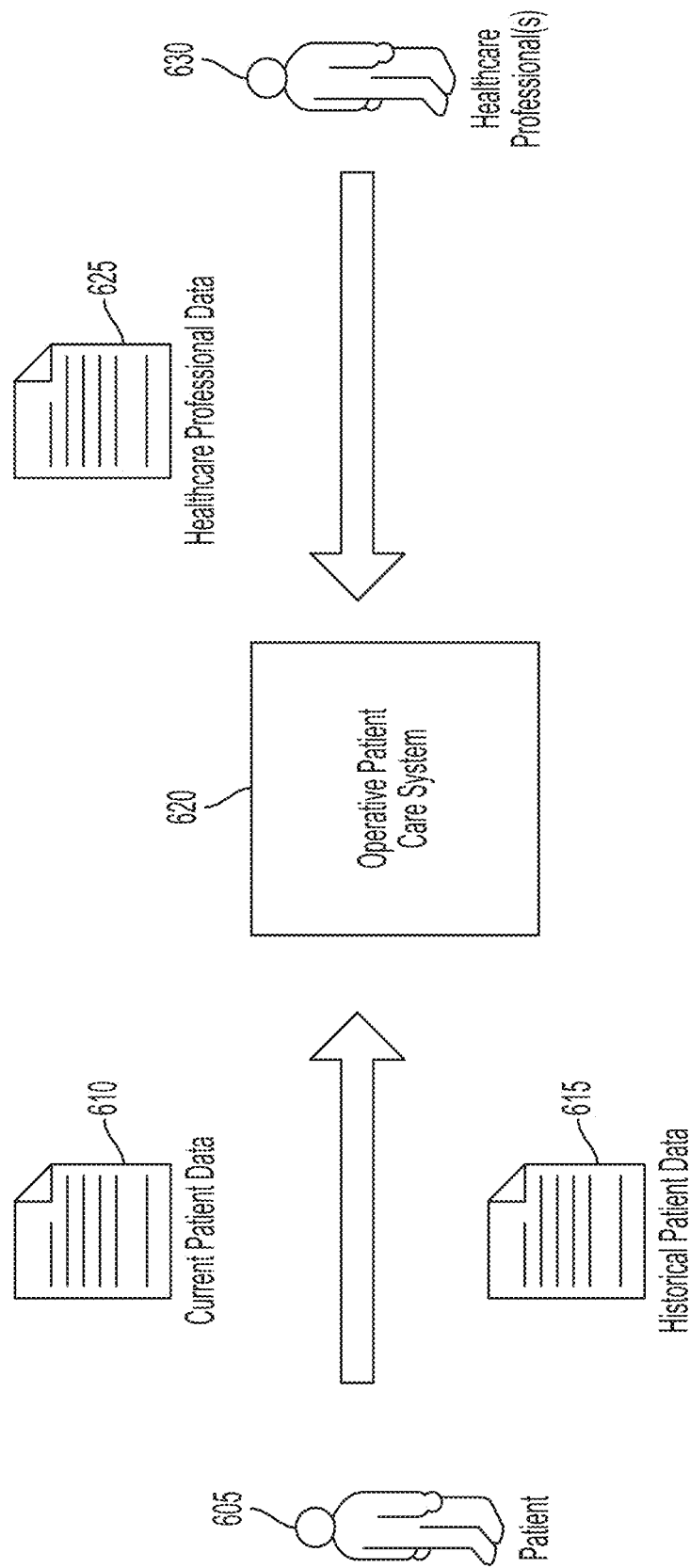
FIG. 6 depicts an operative patient care system and illustrative data sources in accordance with an embodiment.

The general concepts of optimization may be extended to the entire episode of care using an Operative Patient Care System 620 that uses the surgical data, and other data from the Patient 605 and Healthcare Professionals 630 to optimize outcomes and patient satisfaction as depicted in FIG. 6.

Conventionally, pre-operative diagnosis, pre-operative surgical planning, intra-operative execution of a prescribed plan, and post-operative management of total joint arthroplasty are based on individual experience, published literature, and training knowledge bases of surgeons (ultimately, tribal knowledge of individual surgeons and their 'network' of peers and journal publications) and their native ability to make accurate intra-operative tactile discernment of "balance" and accurate manual execution of planar resections using guides and visual cues. This existing knowledge base and execution is limited with respect to the outcomes optimization offered to patients needing care. For example, limits exist with respect to accurately diagnosing a patient to the proper, least-invasive prescribed care; aligning dynamic patient, healthcare economic, and surgeon preferences with patient-desired outcomes; executing a surgical plan resulting in proper bone alignment and balance, etc.; and receiving data from disconnected sources having different biases that are difficult to reconcile into a holistic patient framework. Accordingly, a data-driven tool that more accurately models anatomical response and guides the surgical plan can improve the existing approach.

The Operative Patient Care System 620 is designed to utilize patient specific data, surgeon data, healthcare facility data, and historical outcome data to develop an algorithm that suggests or recommends an optimal overall treatment plan for the patient's entire episode of care (preoperative, operative, and postoperative) based on a desired clinical outcome. For example, in one embodiment, the Operative Patient Care System 620 tracks adherence to the suggested or recommended plan, and adapts the plan based on patient/care provider performance. Once the surgical treatment plan is complete, collected data is logged by the Operative Patient Care System 620 in a historical database. This database is accessible for future patients and the development of future treatment plans. In addition to utilizing statistical and mathematical models, simulation tools (e.g., LIFEMOD®) can be used to simulate outcomes, alignment, kinematics, etc. based on a preliminary or proposed surgical plan, and reconfigure the preliminary or proposed plan to achieve desired or optimal results according to a patient's profile or a surgeon's preferences. The Operative Patient Care System 620 ensures that each patient is receiving personalized surgical and rehabilitative care, thereby improving the chance of successful clinical outcomes and lessening the economic burden on the facility associated with near-term revision.

In some embodiments, the Operative Patient Care System 620 employs a data collecting and management method to provide a detailed surgical case plan with distinct steps that are monitored and/or executed using a CASS 100. The performance of the user(s) is calculated at the completion of each step and can be used to suggest changes to the subsequent steps of the case plan. Case plan generation relies on a series of input data that is stored on a local or cloud-storage database. Input data can be related to both the current patient undergoing treatment and historical data from patients who have received similar treatment(s).

A Patient 605 provides inputs such as Current Patient Data 610 and Historical Patient Data 615 to the Operative Patient Care System 620. Various methods generally known in the art may be used to gather such inputs from the Patient 605. For example, in some embodiments, the Patient 605 fills out a paper or digital survey that is parsed by the Operative Patient Care System 620 to extract patient data. In other embodiments, the Operative Patient Care System 620 may extract patient data from existing information sources, such as electronic medical records (EMRs), health history files, and payer/provider historical files. In still other embodiments, the Operative Patient Care System 620 may provide an application program interface (API) that allows the external data source to push data to the Operative Patient Care System. For example, the Patient 605 may have a mobile phone, wearable device, or other mobile device that collects data (e.g., heart rate, pain or discomfort levels, exercise or activity levels, or patient-submitted responses to the patient's adherence with any number of pre-operative plan criteria or conditions) and provides that data to the Operative Patient Care System 620. Similarly, the Patient 605 may have a digital application on his or her mobile or wearable device that enables data to be collected and transmitted to the Operative Patient Care System 620.

Current Patient Data 610 can include, but is not limited to, activity level, preexisting conditions, comorbidities, prehab performance, health and fitness level, pre-operative expectation level (relating to hospital, surgery, and recovery), a Metropolitan Statistical Area (MSA) driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels of pain or discomfort, care infrastructure information (payer coverage type, home health care infrastructure level, etc.), and an indication of the expected ideal outcome of the procedure.

Historical Patient Data 615 can include, but is not limited to, activity level, preexisting conditions, comorbidities, prehab performance, health and fitness level, pre-operative expectation level (relating to hospital, surgery, and recovery), a MSA driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels or pain or discomfort, care infrastructure information (payer coverage type, home health care infrastructure level, etc.), expected ideal outcome of the procedure, actual outcome of the procedure (patient reported outcomes [PROs], survivorship of implants, pain levels, activity levels, etc.), sizes of implants used, position/orientation/alignment of implants used, soft-tissue balance achieved, etc.

Healthcare Professional(s) 630 conducting the procedure or treatment may provide various types of data 625 to the Operative Patient Care System 620. This Healthcare Professional Data 625 may include, for example, a description of a known or preferred surgical technique (e.g., Cruciate Retaining (CR) vs Posterior Stabilized (PS), up- vs downsizing, tourniquet vs tourniquet-less, femoral stem style, preferred approach for THA, etc.), the level of training of the Healthcare Professional(s) 630 (e.g., years in practice, fellowship trained, where they trained, whose techniques they emulate), previous success level including historical data (outcomes, patient satisfaction), and the expected ideal outcome with respect to range of motion, days of recovery, and survivorship of the device. The Healthcare Professional Data 625 can be captured, for example, with paper or digital surveys provided to the Healthcare Professional 630, via inputs to a mobile application by the Healthcare Professional, or by extracting relevant data from EMRs. In addition, the CASS 100 may provide data such as profile data (e.g., a Patient Specific Knee Instrument Profile) or historical logs describing use of the CASS during surgery.

Information pertaining to the facility where the procedure or treatment will be conducted may be included in the input data. This data can include, without limitation, the following: Ambulatory Surgery Center (ASC) vs hospital, facility trauma level, Comprehensive Care for Joint Replacement Program (CJR) or bundle candidacy, a MSA driven score, community vs metro, academic vs non-academic, postoperative network access (Skilled Nursing Facility [SNF] only, Home Health, etc.), availability of medical professionals, implant availability, and availability of surgical equipment.

These facility inputs can be captured by, for example and without limitation, Surveys (Paper/Digital), Surgery Scheduling Tools (e.g., apps, Websites, Electronic Medical Records [EMRs], etc.), Databases of Hospital Information (on the Internet), etc. Input data relating to the associated healthcare economy including, but not limited to, the socioeconomic profile of the patient, the expected level of reimbursement the patient will receive, and if the treatment is patient specific may also be captured.

These healthcare economic inputs can be captured by, for example and without limitation, Surveys (Paper/Digital), Direct Payer Information, Databases of Socioeconomic status (on the Internet with zip code), etc. Finally, data derived from simulation of the procedure is captured. Simulation inputs include implant size, position, and orientation. Simulation can be conducted with custom or commercially available anatomical modeling software programs (e.g., LIFEMOD®, AnyBody, or OpenSIM). It is noted that the data inputs described above may not be available for every patient, and the treatment plan will be generated using the data that is available.

Prior to surgery, the Patient Data 610, 615 and Healthcare Professional Data 625 may be captured and stored in a cloud-based or online database (e.g., the Surgical Data Server 180 shown in FIG. 5C). Information relevant to the procedure is supplied to a computing system via wireless data transfer or manually with the use of portable media storage. The computing system is configured to generate a case plan for use with a CASS 100. Case plan generation will be described hereinafter. It is noted that the system has access to historical data from previous patients undergoing treatment, including implant size, placement, and orientation as generated by a computer-assisted, patient-specific knee instrument (PSKI) selection system, or automatically by the CASS 100 itself. To achieve this, case log data is uploaded to the historical database by a surgical sales rep or case engineer using an online portal. In some embodiments, data transfer to the online database is wireless and automated.

Historical data sets from the online database are used as inputs to a machine learning model such as, for example, a recurrent neural network (RNN) or other form of artificial neural network. As is generally understood in the art, an artificial neural network functions similar to a biologic neural network and is comprised of a series of nodes and connections. The machine learning model is trained to predict one or more values based on the input data. For the sections that follow, it is assumed that the machine learning model is trained to generate predictor equations. These predictor equations may be optimized to determine the optimal size, position, and orientation of the implants to achieve the best outcome or satisfaction level.

Once the procedure is complete, all patient data and available outcome data, including the implant size, position and orientation determined by the CASS 100, are collected and stored in the historical database. Any subsequent calculation of the target equation via the RNN will include the data from the previous patient in this manner, allowing for continuous improvement of the system.

In addition to, or as an alternative to determining implant positioning, in some embodiments, the predictor equation and associated optimization can be used to generate the resection planes for use with a PSKI system. When used with a PSKI system, the predictor equation computation and optimization are completed prior to surgery. Patient anatomy is estimated using medical image data (x-ray, CT, MRI). Global optimization of the predictor equation can provide an ideal size and position of the implant components. Boolean intersection of the implant components and patient anatomy is defined as the resection volume. PSKI can be produced to remove the optimized resection envelope. In this embodiment, the surgeon cannot alter the surgical plan intraoperatively.

The surgeon may choose to alter the surgical case plan at any time prior to or during the procedure. If the surgeon elects to deviate from the surgical case plan, the altered size, position, and/or orientation of the component(s) is locked, and the global optimization is refreshed based on the new size, position, and/or orientation of the component(s) (using the techniques previously described) to find the new ideal position of the other component(s) and the corresponding resections needed to be performed to achieve the newly optimized size, position and/or orientation of the component(s). For example, if the surgeon determines that the size, position and/or orientation of the femoral implant in a TKA needs to be updated or modified intraoperatively, the femoral implant position is locked relative to the anatomy, and the new optimal position of the tibia will be calculated (via global optimization) considering the surgeon's changes to the femoral implant size, position and/or orientation. Furthermore, if the surgical system used to implement the case plan is robotically assisted (e.g., as with NAVIO® or the MAKO Rio), bone removal and bone morphology during the surgery can be monitored in real time. If the resections made during the procedure deviate from the surgical plan, the subsequent placement of additional components may be optimized by the processor taking into account the actual resections that have already been made.

Figure 7A:
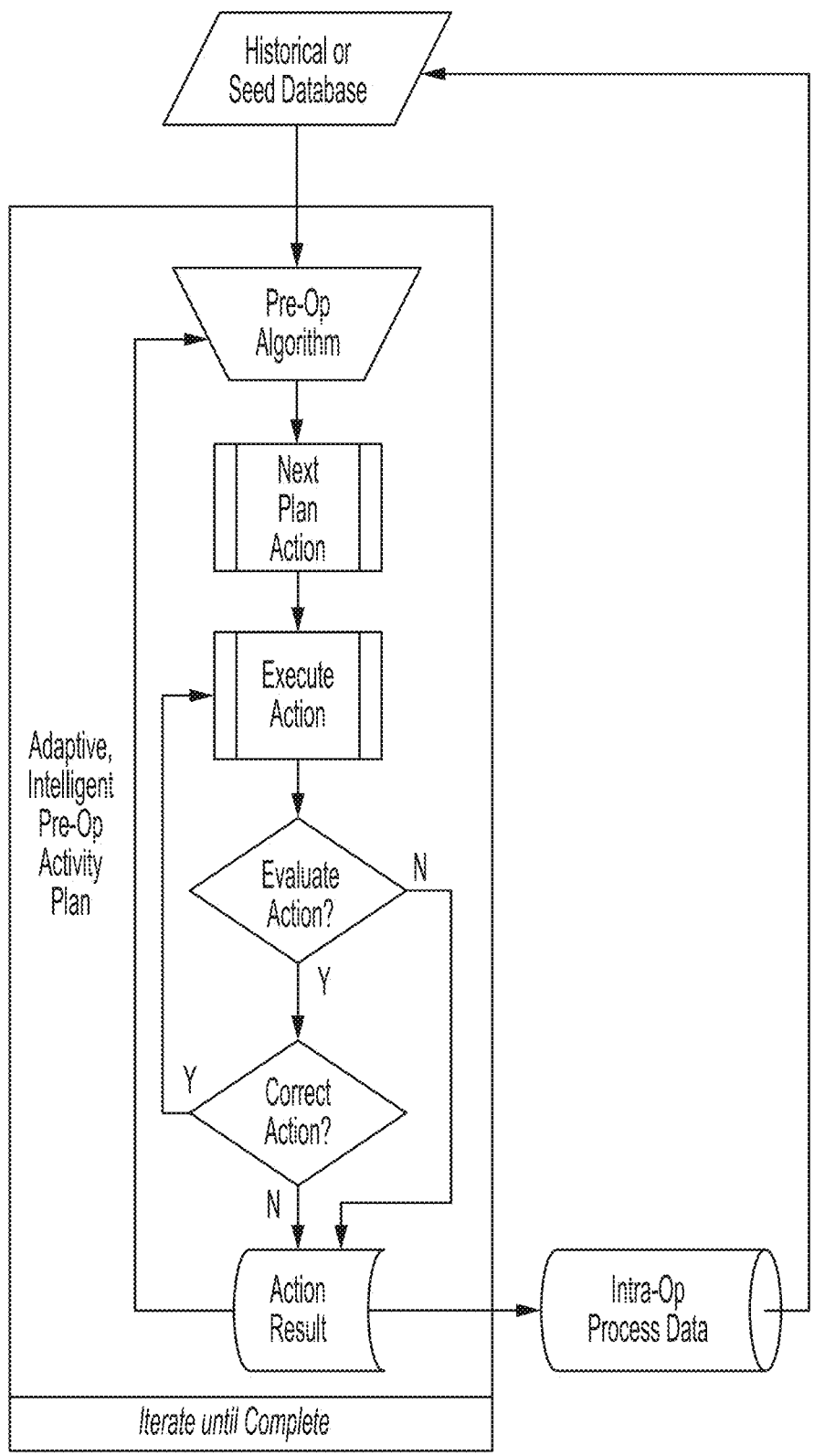
FIG. 7A depicts an illustrative flow diagram for determining a pre-operative surgical plan in accordance with an embodiment.

FIG. 7A illustrates how the Operative Patient Care System 620 may be adapted for performing case plan matching services. In this example, data is captured relating to the current patient 610 and is compared to all or portions of a historical database of patient data and associated outcomes 615. For example, the surgeon may elect to compare the plan for the current patient against a subset of the historical database. Data in the historical database can be filtered to include, for example, only data sets with favorable outcomes, data sets corresponding to historical surgeries of patients with profiles that are the same or similar to the current patient profile, data sets corresponding to a particular surgeon, data sets corresponding to a particular element of the surgical plan (e.g., only surgeries where a particular ligament is retained), or any other criteria selected by the surgeon or medical professional. If, for example, the current patient data matches or is correlated with that of a previous patient who experienced a good outcome, the case plan from the previous patient can be accessed and adapted or adopted for use with the current patient. The predictor equation may be used in conjunction with an intra-operative algorithm that identifies or determines the actions associated with the case plan. Based on the relevant and/or preselected information from the historical database, the intra-operative algorithm determines a series of recommended actions for the surgeon to perform. Each execution of the algorithm produces the next action in the case plan. If the surgeon performs the action, the results are evaluated. The results of the surgeon's performing the action are used to refine and update inputs to the intra-operative algorithm for generating the next step in the case plan. Once the case plan has been fully executed all data associated with the case plan, including any deviations performed from the recommended actions by the surgeon, are stored in the database of historical data. In some embodiments, the system utilizes preoperative, intraoperative, or postoperative modules in a piecewise fashion, as opposed to the entire continuum of care. In other words, caregivers can prescribe any permutation or combination of treatment modules including the use of a single module. These concepts are illustrated in FIG. 7B and can be applied to any type of surgery utilizing the CASS 100.

Surgery Process Display

As noted above with respect to FIGS. 1 and 5A-5C, the various components of the CASS 100 generate detailed data records during surgery. The CASS 100 can track and record various actions and activities of the surgeon during each step of the surgery and compare actual activity to the preoperative or intraoperative surgical plan. In some embodiments, a software tool may be employed to process this data into a format where the surgery can be effectively "played-back." For example, in one embodiment, one or more GUIs may be used that depict all of the information presented on the Display 125 during surgery. This can be supplemented with graphs and images that depict the data collected by different tools. For example, a GUI that provides a visual depiction of the knee during tissue resection may provide the measured torque and displacement of the resection equipment adjacent to the visual depiction to better provide an understanding of any deviations that occurred from the planned resection area. The ability to review a playback of the surgical plan or toggle between different phases of the actual surgery vs. the surgical plan could provide benefits to the surgeon and/or surgical staff, allowing such persons to identify any deficiencies or challenging phases of a surgery so that they can be modified in future surgeries. Similarly, in academic settings, the aforementioned GUIs can be used as a teaching tool for training future surgeons and/or surgical staff. Additionally, because the data set effectively records many elements of the surgeon's activity, it may also be used for other reasons (e.g., legal or compliance reasons) as evidence of correct or incorrect performance of a particular surgical procedure.

Over time, as more and more surgical data is collected, a rich library of data may be acquired that describes surgical procedures performed for various types of anatomy (knee, shoulder, hip, etc.) by different surgeons for different patients. Moreover, information such as implant type and dimension, patient demographics, etc. can further be used to enhance the overall dataset. Once the dataset has been established, it may be used to train a machine learning model (e.g., RNN) to make predictions of how surgery will proceed based on the current state of the CASS 100.

Training of the machine learning model can be performed as follows. The overall state of the CASS 100 can be sampled over a plurality of time periods for the duration of the surgery. The machine learning model can then be trained to translate a current state at a first time period to a future state at a different time period. By analyzing the entire state of the CASS 100 rather than the individual data items, any causal effects of interactions between different components of the CASS 100 can be captured. In some embodiments, a plurality of machine learning models may be used rather than a single model. In some embodiments, the machine learning model may be trained not only with the state of the CASS 100, but also with patient data (e.g., captured from an EMR) and an identification of members of the surgical staff. This allows the model to make predictions with even greater specificity. Moreover, it allows surgeons to selectively make predictions based only on their own surgical experiences if desired.

Figure 7C:
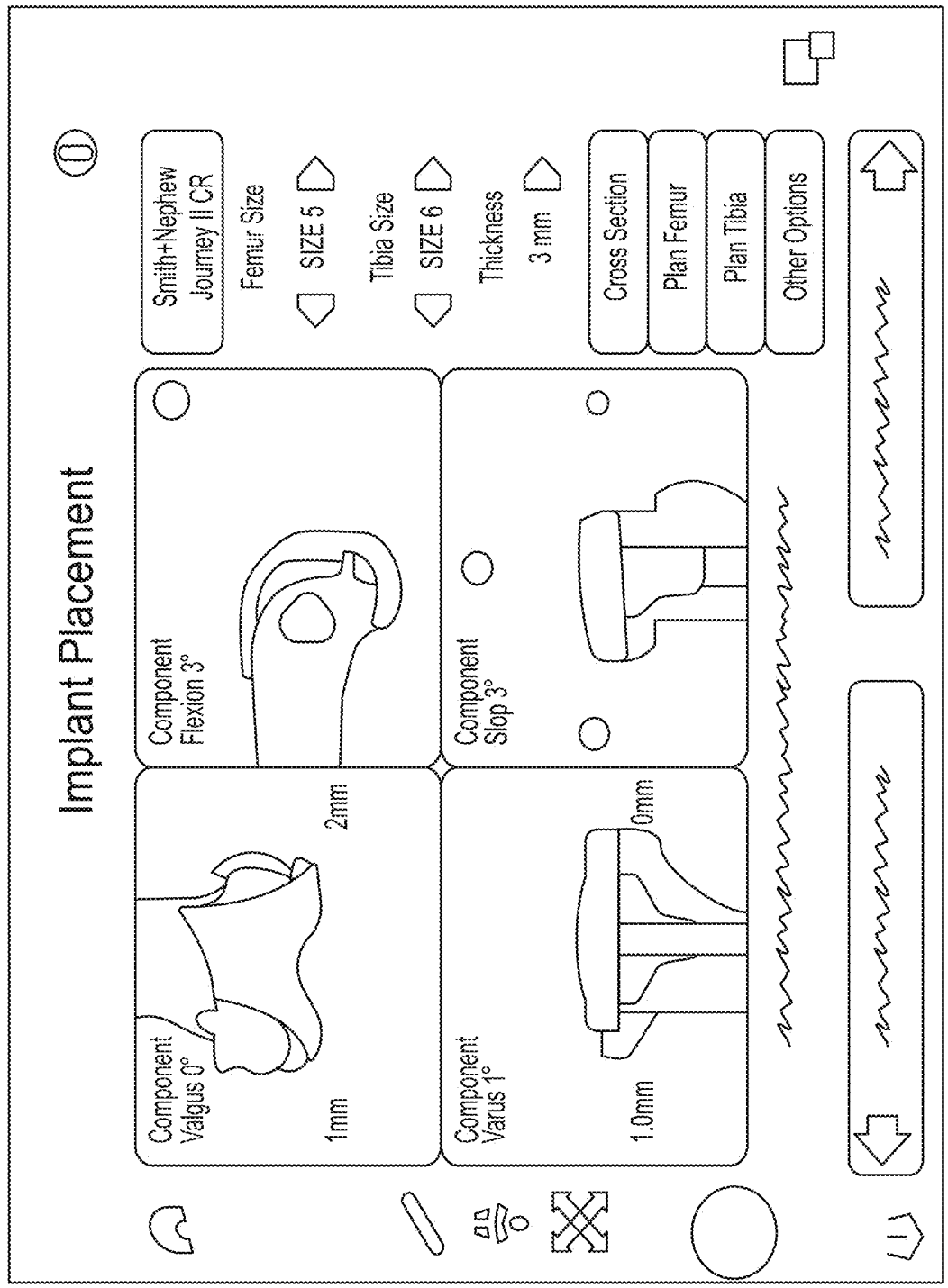
FIG. 7C depicts illustrative graphical user interfaces including images depicting an implant placement in accordance with an embodiment.
Figure 7C:
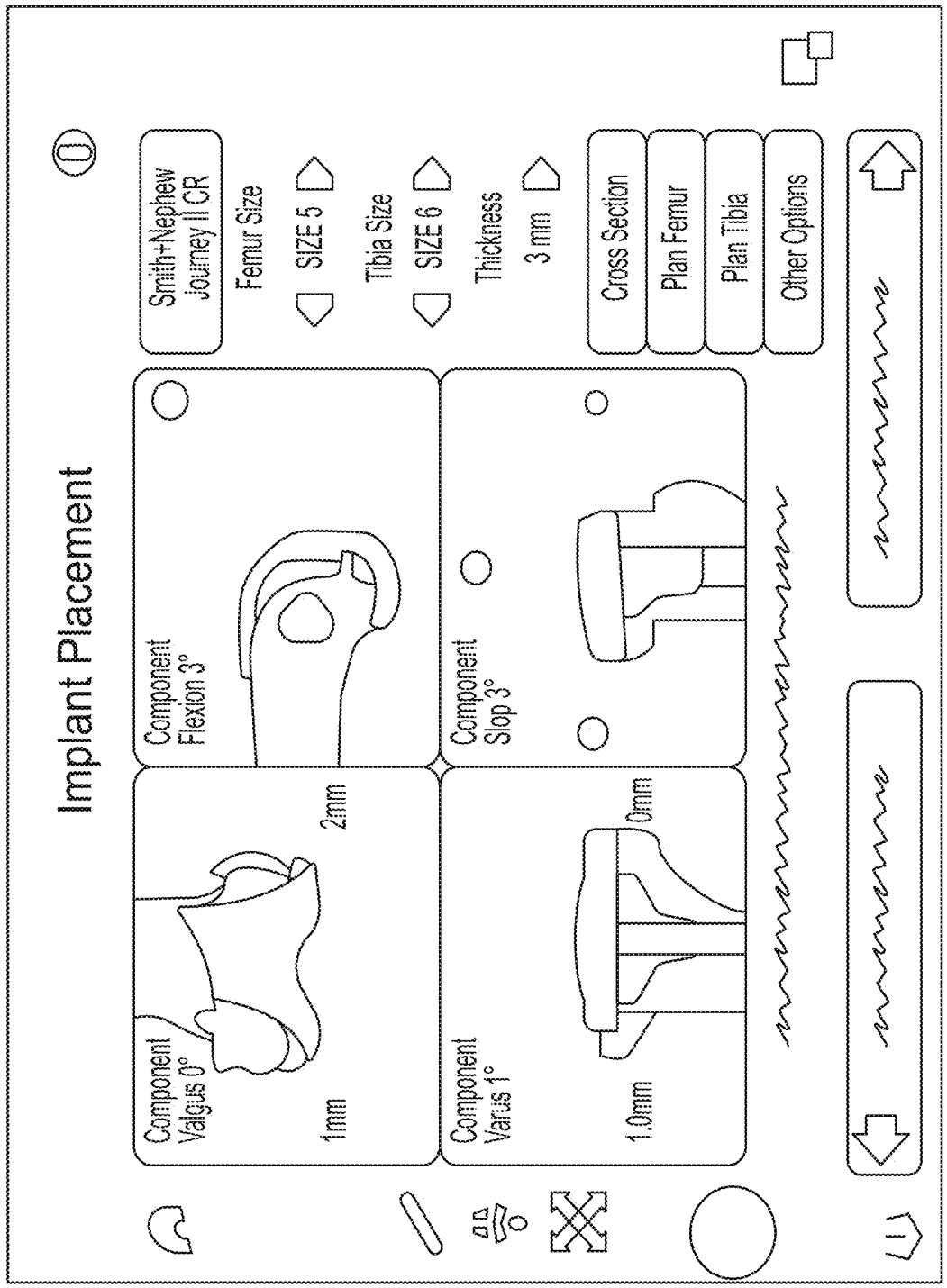
Figure 7C:
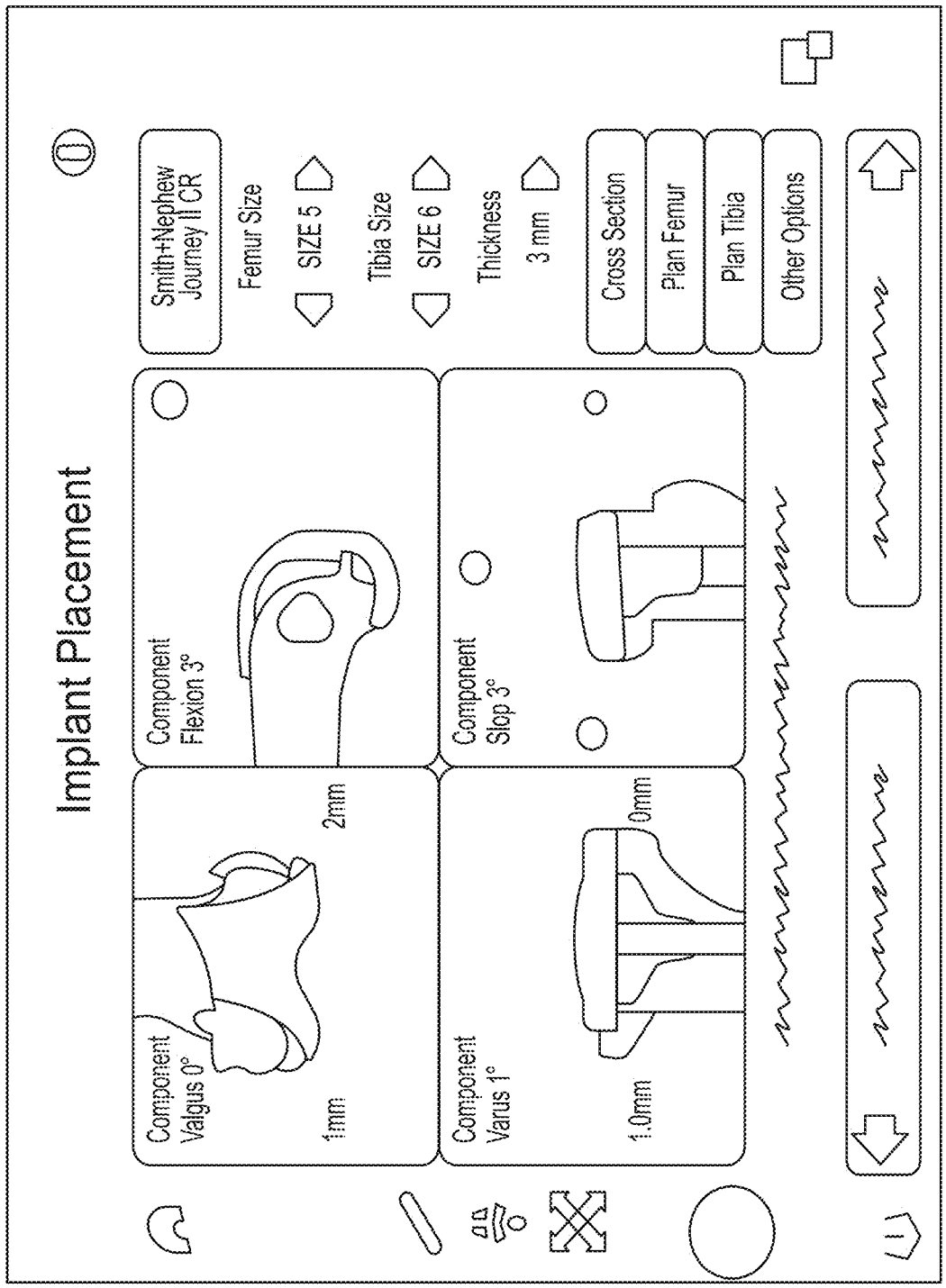

In some embodiments, predictions or recommendations made by the aforementioned machine learning models can be directly integrated into the surgical workflow. For example, in some embodiments, the Surgical Computer 150 may execute the machine learning model in the background making predictions or recommendations for upcoming actions or surgical conditions. A plurality of states can thus be predicted or recommended for each period. For example, the Surgical Computer 150 may predict or recommend the state for the next 5 minutes in 30 second increments. Using this information, the surgeon can utilize a "process display" view of the surgery that allows visualization of the future state. For example, FIG. 7C depicts a series of images that may be displayed to the surgeon depicting the implant placement interface. The surgeon can cycle through these images, for example, by entering a particular time into the display 125 of the CASS 100 or instructing the system to advance or rewind the display in a specific time increment using a tactile, oral, or other instruction. In one embodiment, the process display can be presented in the upper portion of the surgeon's field of view in the AR HMD. In some embodiments, the process display can be updated in real-time. For example, as the surgeon moves resection tools around the planned resection area, the process display can be updated so that the surgeon can see how his or her actions are affecting the other factors of the surgery.

In some embodiments, rather than simply using the current state of the CASS 100 as an input to the machine learning model, the inputs to the model may include a planned future state. For example, the surgeon may indicate that he or she is planning to make a particular bone resection of the knee joint. This indication may be entered manually into the Surgical Computer 150 or the surgeon may verbally provide the indication. The Surgical Computer 150 can then produce a film strip showing the predicted effect of the cut on the surgery. Such a film strip can depict over specific time increments how the surgery will be affected, including, for example, changes in the patient's anatomy, changes to implant position and orientation, and changes regarding surgical intervention and instrumentation, if the contemplated course of action were to be performed. A surgeon or medical professional can invoke or request this type of film strip at any point in the surgery to preview how a contemplated course of action would affect the surgical plan if the contemplated action were to be carried out.

It should be further noted that, with a sufficiently trained machine learning model and robotic CASS, various elements of the surgery can be automated such that the surgeon only needs to be minimally involved, for example, by only providing approval for various steps of the surgery. For example, robotic control using arms or other means can be gradually integrated into the surgical workflow over time with the surgeon slowly becoming less and less involved with manual interaction versus robot operation. The machine learning model in this case can learn what robotic commands are required to achieve certain states of the CASS-implemented plan. Eventually, the machine learning model may be used to produce a film strip or similar view or display that predicts and can preview the entire surgery from an initial state. For example, an initial state may be defined that includes the patient information, the surgical plan, implant characteristics, and surgeon preferences. Based on this information, the surgeon could preview an entire surgery to confirm that the CASS-recommended plan meets the surgeon's expectations and/or requirements. Moreover, because the output of the machine learning model is the state of the CASS 100 itself, commands can be derived to control the components of the CASS to achieve each predicted state. In the extreme case, the entire surgery could thus be automated based on just the initial state information.

Using the Point Probe to Acquire High Resolution of Key Areas During Hip Surgeries Use of the point probe is described in U.S. patent application Ser. No. 14/955,742 entitled "Systems and Methods for Planning and Performing Image Free Implant Revision Surgery," the entirety of which is incorporated herein by reference. Briefly, an optically tracked point probe may be used to map the actual surface of the target bone that needs a new implant. Mapping is performed after removal of the defective or worn-out implant, as well as after removal of any diseased or otherwise unwanted bone. A plurality of points is collected on the bone surfaces by brushing or scraping the entirety of the remaining bone with the tip of the point probe. This is referred to as tracing or "painting" the bone. The collected points are used to create a three-dimensional model or surface map of the bone surfaces in the computerized planning system. The created 3D model of the remaining bone is then used as the basis for planning the procedure and necessary implant sizes. An alternative technique that uses X-rays to determine a 3D model is described in U.S. patent application Ser. No. 16/387,151, filed Apr. 17, 2019 and entitled "Three-Dimensional Selective Bone Matching" and U.S. patent application Ser. No. 16/789,930, filed Feb. 13, 2020 and entitled "Three-Dimensional Selective Bone Matching," the entirety of each of which is incorporated herein by reference.

For hip applications, the point probe painting can be used to acquire high resolution data in key areas such as the acetabular rim and acetabular fossa. This can allow a surgeon to obtain a detailed view before beginning to ream. For example, in one embodiment, the point probe may be used to identify the floor (fossa) of the acetabulum. As is well understood in the art, in hip surgeries, it is important to ensure that the floor of the acetabulum is not compromised during reaming so as to avoid destruction of the medial wall. If the medial wall were inadvertently destroyed, the surgery would require the additional step of bone grafting. With this in mind, the information from the point probe can be used to provide operating guidelines to the acetabular reamer during surgical procedures. For example, the acetabular reamer may be configured to provide haptic feedback to the surgeon when he or she reaches the floor or otherwise deviates from the surgical plan. Alternatively, the CASS 100 may automatically stop the reamer when the floor is reached or when the reamer is within a threshold distance.

As an additional safeguard, the thickness of the area between the acetabulum and the medial wall could be estimated. For example, once the acetabular rim and acetabular fossa has been painted and registered to the pre-operative 3D model, the thickness can readily be estimated by comparing the location of the surface of the acetabulum to the location of the medial wall. Using this knowledge, the CASS 100 may provide alerts or other responses in the event that any surgical activity is predicted to protrude through the acetabular wall while reaming.

The point probe may also be used to collect high resolution data of common reference points used in orienting the 3D model to the patient. For example, for pelvic plane landmarks like the ASIS and the pubic symphysis, the surgeon may use the point probe to paint the bone to represent a true pelvic plane. Given a more complete view of these landmarks, the registration software has more information to orient the 3D model.

The point probe may also be used to collect high-resolution data describing the proximal femoral reference point that could be used to increase the accuracy of implant placement. For example, the relationship between the tip of the Greater Trochanter (GT) and the center of the femoral head is commonly used as reference point to align the femoral component during hip arthroplasty. The alignment is highly dependent on proper location of the GT; thus, in some embodiments, the point probe is used to paint the GT to provide a high-resolution view of the area. Similarly, in some embodiments, it may be useful to have a high-resolution view of the Lesser Trochanter (LT). For example, during hip arthroplasty, the Dorr Classification helps to select a stem that will maximize the ability of achieving a press-fit during surgery to prevent micromotion of femoral components post-surgery and ensure optimal bony ingrowth. As is generated understood in the art, the Dorr Classification measures the ratio between the canal width at the LT and the canal width 10 cm below the LT. The accuracy of the classification is highly dependent on the correct location of the relevant anatomy. Thus, it may be advantageous to paint the LT to provide a high-resolution view of the area.

In some embodiments, the point probe is used to paint the femoral neck to provide high-resolution data that allows the surgeon to better understand where to make the neck cut. The navigation system can then guide the surgeon as they perform the neck cut. For example, as understood in the art, the femoral neck angle is measured by placing one line down the center of the femoral shaft and a second line down the center of the femoral neck. Thus, a high-resolution view of the femoral neck (and possibly the femoral shaft as well) would provide a more accurate calculation of the femoral neck angle.

High-resolution femoral head neck data also could be used for a navigated resurfacing procedure where the software/hardware aids the surgeon in preparing the proximal femur and placing the femoral component. As is generally understood in the art, during hip resurfacing, the femoral head and neck are not removed; rather, the head is trimmed and capped with a smooth metal covering. In this case, it would be advantageous for the surgeon to paint the femoral head and cap so that an accurate assessment of their respective geometries can be understood and used to guide trimming and placement of the femoral component.

Registration of Pre-Operative Data to Patient Anatomy Using the Point Probe

As noted above, in some embodiments, a 3D model is developed during the pre-operative stage based on 2D or 3D images of the anatomical area of interest. In such embodiments, registration between the 3D model and the surgical site is performed prior to the surgical procedure. The registered 3D model may be used to track and measure the patient's anatomy and surgical tools intraoperatively.

During the surgical procedure, landmarks are acquired to facilitate registration of this pre-operative 3D model to the patient's anatomy. For knee procedures, these points could comprise the femoral head center, distal femoral axis point, medial and lateral epicondyles, medial and lateral malleolus, proximal tibial mechanical axis point, and tibial A/P direction. For hip procedures these points could comprise the anterior superior iliac spine (ASIS), the pubic symphysis, points along the acetabular rim and within the hemisphere, the greater trochanter (GT), and the lesser trochanter (LT).

In a revision surgery, the surgeon may paint certain areas that contain anatomical defects to allow for better visualization and navigation of implant insertion. These defects can be identified based on analysis of the pre-operative images. For example, in one embodiment, each pre-operative image is compared to a library of images showing "healthy" anatomy (i.e., without defects). Any significant deviations between the patient's images and the healthy images can be flagged as a potential defect. Then, during surgery, the surgeon can be warned of the possible defect via a visual alert on the display 125 of the CASS 100. The surgeon can then paint the area to provide further detail regarding the potential defect to the Surgical Computer 150.

In some embodiments, the surgeon may use a non-contact method for registration of bony anatomy intra-incision. For example, in one embodiment, laser scanning is employed for registration. A laser stripe is projected over the anatomical area of interest and the height variations of the area are detected as changes in the line. Other non-contact optical methods, such as white light interferometry or ultrasound, may alternatively be used for surface height measurement or to register the anatomy. For example, ultrasound technology may be beneficial where there is soft tissue between the registration point and the bone being registered (e.g., ASIS, pubic symphysis in hip surgeries), thereby providing for a more accurate definition of anatomic planes.

Dual Scale Calibration Device

As discussed herein, certain surgeries, such as joint reconstruction procedures, utilize digital templating to plan the surgical procedure and select suitable implant components. As generally described herein, 2D images may be captured with one or more fiducial markers in the field of view that may be used to scale the 2D images for implant selection and design. Ideally, the fiducial markers enable location of the hip plane (e.g., coronal plane) based on known dimensions of fiducial markers.

Figure 8A:
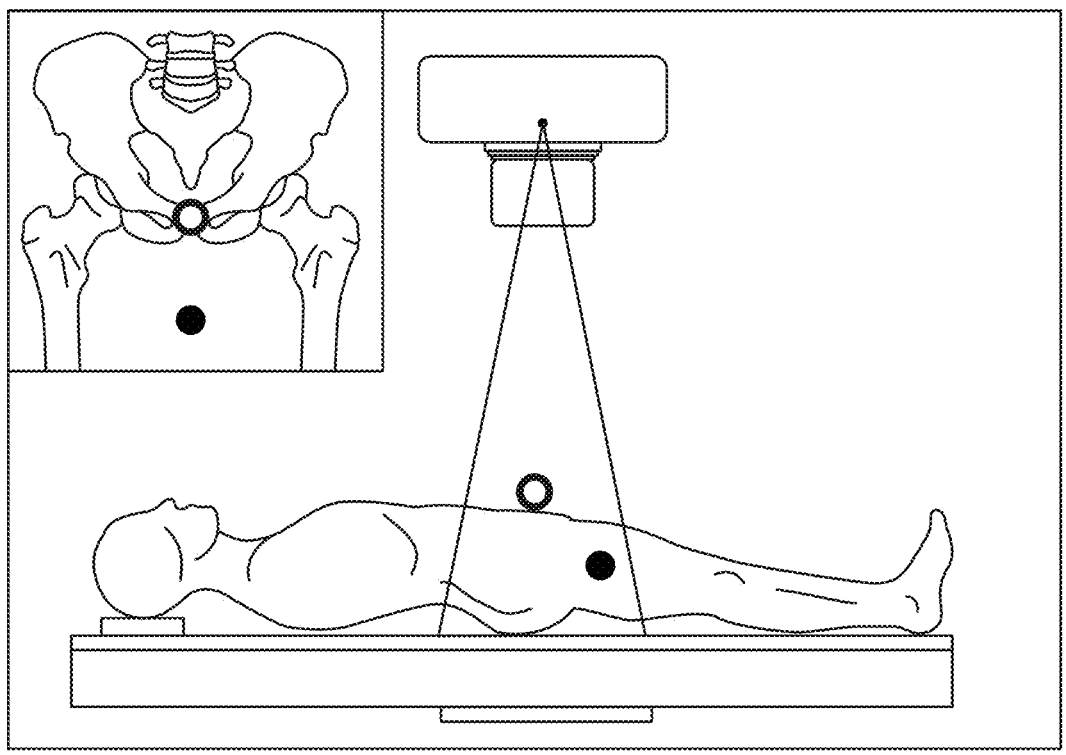
FIG. 8A depicts a conventional supine X-ray imaging system.
Figure 8B:
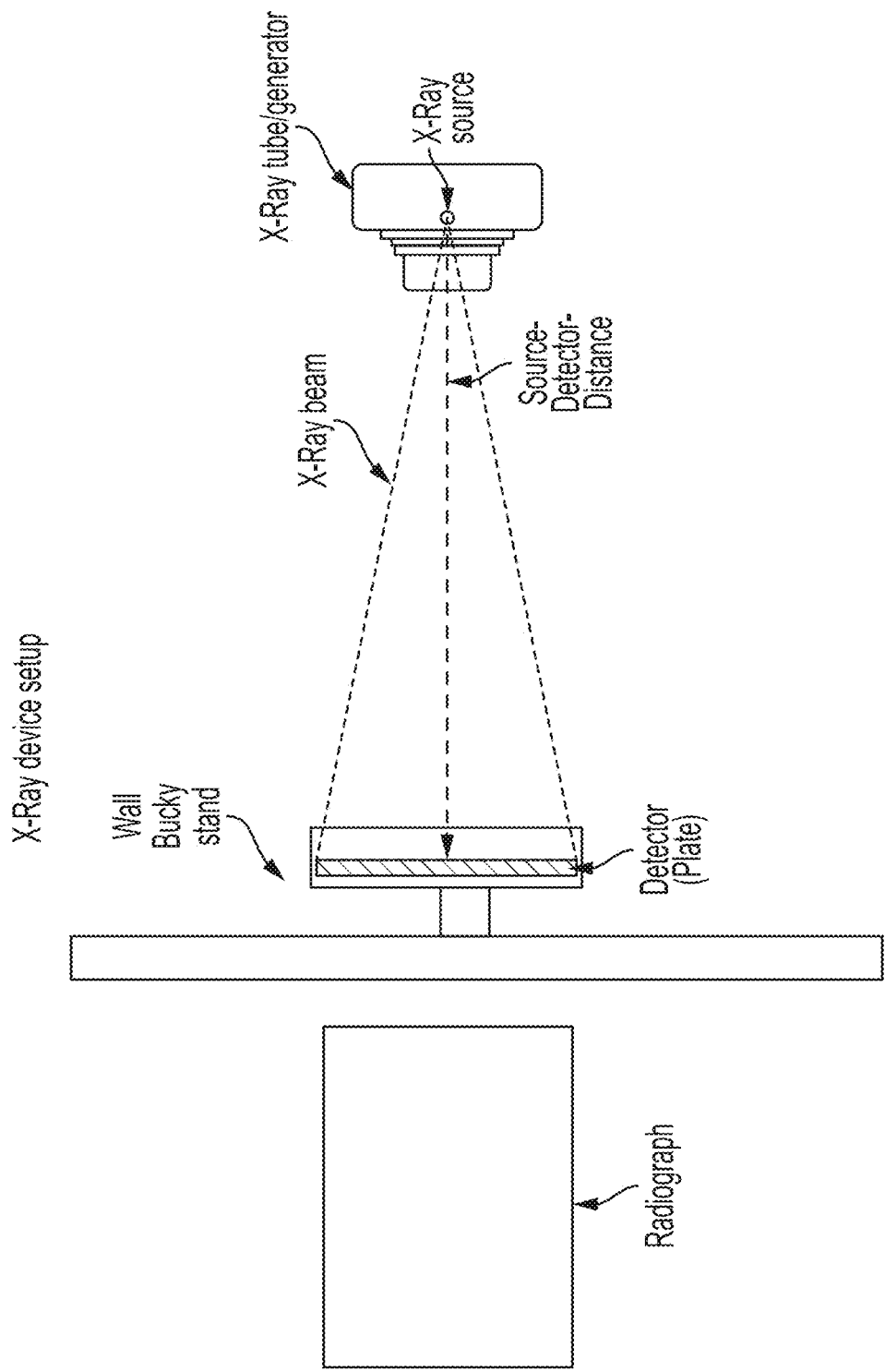
FIG. 8B depicts a conventional standing X-ray imaging system.

For example, FIG. 8A depicts a conventional fiducial marker (represented as a filled circle) positioned between the legs of the patient. In conventional single fiducial marker systems, a medical professional may align the fiducial marker with the coronal plane of the patient and the central beam from the imaging source (e.g., approximated by the sagittal plane of the patient) in order to allow for proper scaling of the resulting 2D images based on the size of the fiducial marker in the 2D images. However, precise positioning of the fiducial marker requires a high degree of skill and may also be invasive and uncomfortable for the patient. Placement between the legs is often unpleasant and/or awkward for the patient and the medical professional, resulting in less care and attention being given to proper fiducial marker placement. In some embodiments, a fiducial marker must be positioned between the legs of the patient at a depth substantially near the hip plane and a lateral position substantially near the sagittal plane (i.e., vertical center line of the anatomy). For example, the fiducial marker may be attached to an adjustable or articulable arm resting on an imaging table. The elevation of the fiducial marker from the imaging table surface may be adjusted to align with the hip plane and the lateral position of the fiducial marker may be adjusted to align with the central beam. Positioning of the fiducial marker anterior or posterior of the hip plane may result in inaccurate scaling of the 2D images. Furthermore, improper lateral positioning of the fiducial marker may result in projectional effects in the 2D image, whereby the fiducial marker appears distorted and complicates the scaling of the 2D image. Proper positioning may require a great deal of expertise, time, and attention to detail by the medical professional. As such, positioning of conventional fiducial markers can be highly variable and prone to errors that result in inaccurate scaling. While fiducial markers may be utilized during imaging with supine imaging systems as depicted in FIG. 8A, it should be understood that it may also be advantageous to use fiducial markers with standing X-ray systems. For example, FIG. 8B depicts a conventional standing X-ray system.

Figure 8C:
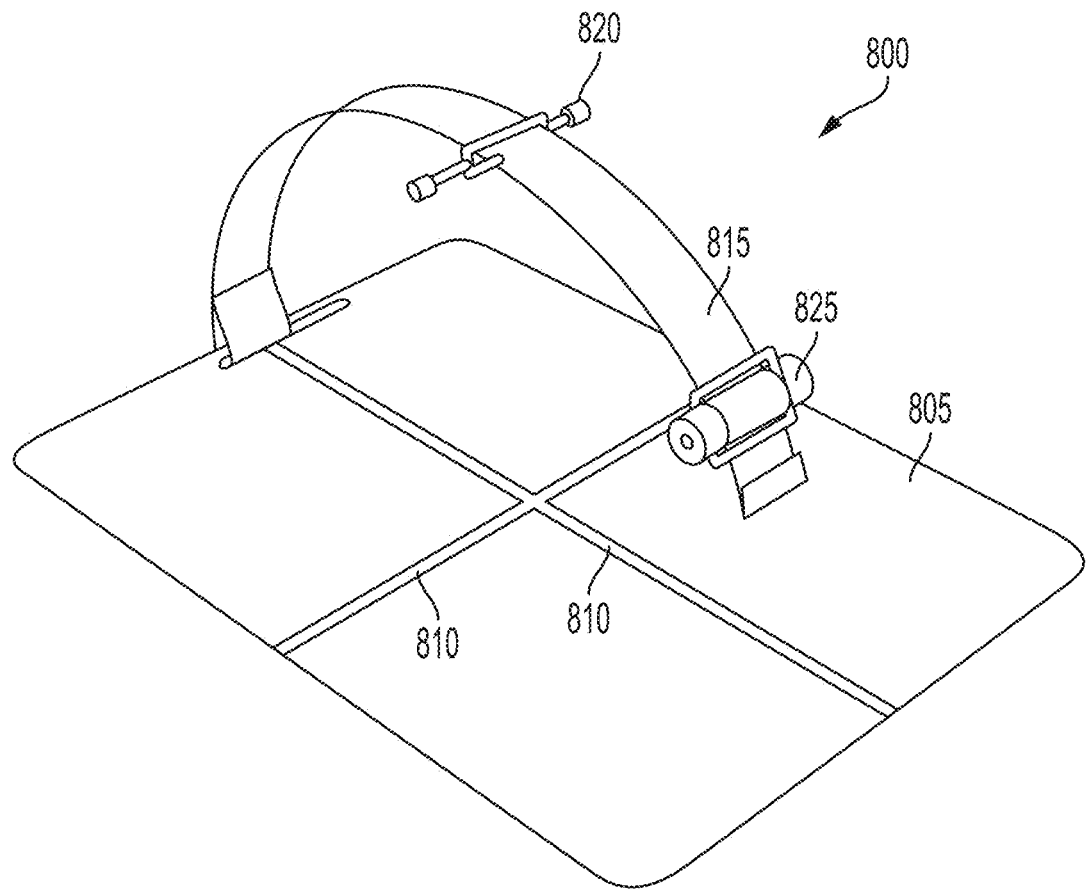
FIG. 8C depicts a conventional multi-fiducial marker system.

In some instances, conventional fiducial marker systems may use a plurality of fiducial markers to estimate the location of the hip plane for scaling of the 2D images. For example, the KINGMARK calibration system from BRAINLAB, INC. is a multi-fiducial marker system that utilizes two fiducial markers placed above and below the patient. Referring now to FIG. 8C, a multi-fiducial marker system 800 such as the KINGMARK system may include a substantially rigid board 805 comprising one or more first fiducial markers 810 (e.g., radiopaque rods) and a strap 815 affixed to the rigid board 810 and having one or more second fiducial markers 820 (e.g., an array of linked radiopaque spheres) affixed thereto. In use, the patient may lay on the rigid board 810 in a supine position such that a posterior surface of the pelvic region is positioned directly over the rigid board 810. The strap 815 may be laid across the patient's pelvis and the one or more second fiducial markers may be positioned directly over the patient's suprapubic region. In some embodiments, the strap 815 may further comprise a weight 825 for pulling the strap 815 taut over the body of the patient and reducing inadvertent movement of the one or more second fiducial markers 820. After collecting 2D images of the patient, a distance of the first fiducial markers and the second fiducial markers from the imaging detector (as depicted in FIG. 8A) may be inferred by comparing the dimensions of the fiducial markers in the 2D images to the known dimensions of the fiducial markers. The position of the first fiducial markers may correspond to a position of the dorsal surface of the patient and the position of the second fiducial markers may correspond to a position of the ventral surface of the patient. Thereafter, a distance of the hip plane from the detector may be calculated based on the dorsal and ventral surface positions. For example, the relative location of the hip plane with respect to the dorsal or ventral surfaces may be relatively constant across populations. Accordingly, based on empirical data and/or historical patient data, a ratio indicative of the distance to the hip plane from the dorsal or ventral surface compared to an overall pelvic depth may be applied to estimate the distance of the hip plane from the detector. Thus, the 2D images may be scaled according to the distance of the hip plane.

However, multi-fiducial marker systems such as those described may still suffer from several drawbacks. For example, laying upon a board or other fiducial marker may be uncomfortable and may affect the patient during imaging. Additionally, where the second fiducial markers are not properly placed at the central beam from the imaging source, inaccuracies in scaling may result due to projectional effects. Furthermore, such systems are not easily adaptable to use with standing X-ray systems such as the system depicted in FIG. 8B.

Figure 9A:
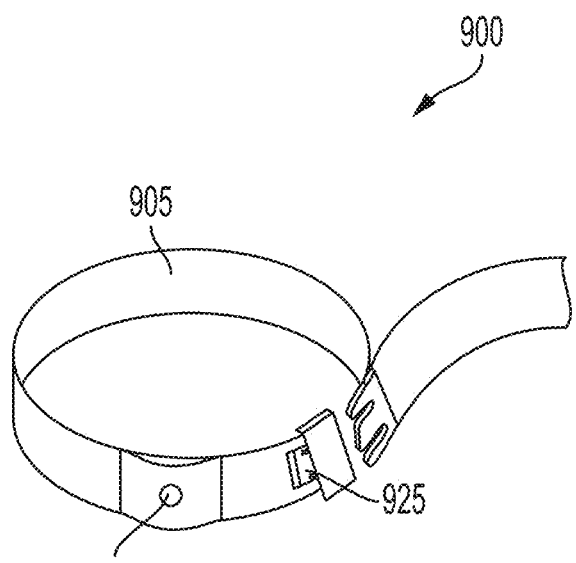
FIGS. 9A-9C depict illustrative views of a dual scale calibration device in accordance with an embodiment.
Figure 9B:
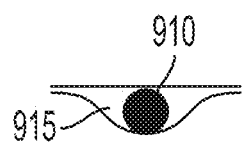
Figure 9C:
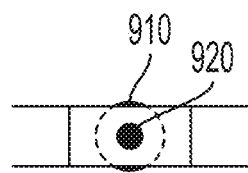
Figure 10:
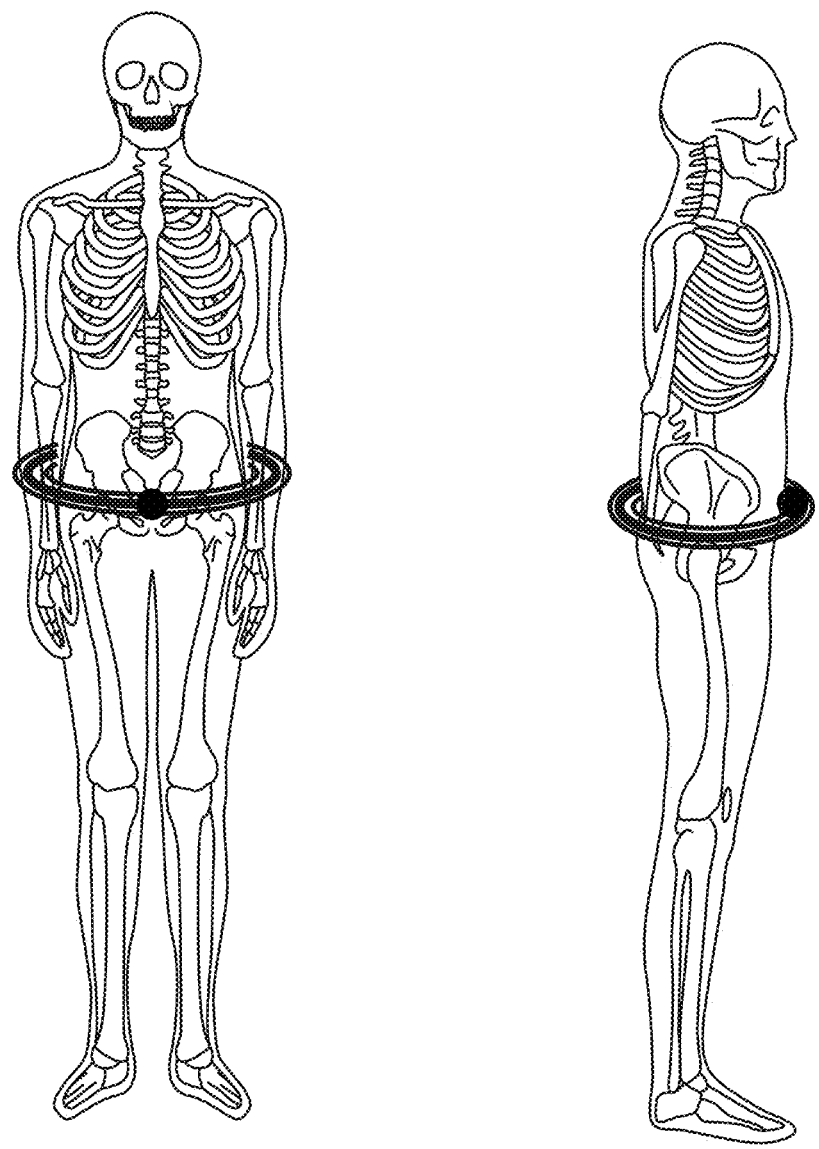
FIG. 10 depicts an illustrative dual scale calibration device applied to the waist of a patient in accordance with an embodiment.

Referring now to FIGS. 9A-9C and 10, an illustrative embodiment of a dual scale calibration device is depicted. The dual scale calibration device 900 may comprise a belt 905 configured to be secured around the waist of a patient and a single fiducial marker 910 (i.e., a monomarker) coupled to the belt 905 and configured for visualization by conventional 2D imaging techniques, such as, for example, X-ray imaging. FIG. 8A also depicts a fiducial marker (represented as a hollow circle) as described herein positioned at the waist of the patient. FIG. 10 further depicts an exemplary dual scale calibration device as described herein attached to the waist of a patient.

As shown in FIGS. 9A-9C, the belt 905 may include a pocket 915 formed along the loop of the belt 905 configured to retain the monomarker 910 in a secure manner. In some embodiments, the pocket 915 may have a width that is substantially equal to the diameter of the monomarker 910 to tightly retain the monomarker 910 therein. As most clearly depicted in FIG. 9B, in some embodiments the pocket 915 may have a width that is less than the diameter of the monomarker 910. A hole 920 may be formed in the material of the pocket 915 so that the monomarker 910 may extend through the hole 920 and bulge out of the pocket 915, thereby securely retaining the monomarker 910 in the pocket 915. In some embodiments, the pocket 915 may be formed of an elastic material such that the pocket 915 conforms to the shape of the monomarker 910 to resiliently retain the monomarker 910 within the pocket 905.

Securing the monomarker 910 within a pocket as shown in FIG. 9B may be particularly advantageous in order to firmly press the monomarker 910 into the soft tissue of the patient. Accordingly, instead of the entire monomarker 910 sitting above the ventral surface of the patient, the monomarker 910 may be pressed into the soft tissue such that the center of the monomarker 910 may be located at the ventral surface of the patient. As further described herein, co-location of the center of the monomarker 910 with the ventral surface of the patient may be advantageous for various calculations. However, in some embodiments, the monomarker 910 may be placed over the ventral surface such that the entire monomarker 910 sits above the ventral surface of the patient. However, in some embodiments, the monomarker 910 may be placed over the ventral surface such that the entire monomarker 910 sits above the ventral surface of the patient. For example, the monomarker 910 may be secured to a front surface of the belt 905. In some embodiments, the monomarker 910 may be secured to a rigid or semi-rigid baseplate on a portion of the belt 905. The baseplate may be radio-transparent such that it does not interfere with the detection of the monomarker 910.

In some embodiments, the belt 905 is a fixed diameter belt. Accordingly, the belt 905 may be configured to fit patients of a particular size or range of sizes. In some embodiments, the belts 905 may be produced in a variety of sizes to fit patients of different sizes or ranges of sizes.

In some embodiments, the belt 905 is an adjustable diameter belt comprising an adjustment mechanism 925. For example, the adjustment mechanism 925 may be an adjustable slide on the belt 905 that may be moved in a first direction to shorten the loop of the belt 905 and in a second direction to lengthen the loop of the belt 905. In this manner, the diameter of the loop may be adjusted to fit patients of various sizes. In some embodiments, the belt 905 and/or adjustment mechanism 925 includes markings to indicate the diameter of the loop as it is adjusted. Accordingly, the belt 905 and adjustment mechanism may be used to measure a circumference of the pelvis. Additionally or alternatively, the belt 905 may be provided in a plurality of sizes corresponding to different standard waist or belt sizes or ranges thereof.

In some embodiments, the adjustable diameter belt 905 may be adjustable by other means. For example, the belt 905 may be formed from an elastic material configured to conform to the shape of the patient (see, e.g., FIG. 10). Accordingly, the belt 905 may pulled apart to be easily placed around the waist of the patient and may shrink to the diameter of the patient upon release.

In some embodiments, the loop of the belt 905 may be selectively opened and closed. For example, as shown in FIG. 9A, the belt 905 may include a side release buckle comprising a male component on a first end of the belt 905 and a female component on the second end of the belt 905. The male and female components may be selectively fastened to close the belt 905 and released to open the belt 905. Accordingly, the loop of the belt 905 may be opened to be placed around the waist of the patient and may be secured thereafter. Alternate means of selectively fastening and releasing the ends of the belt 905 to close and open the loop may be provided and implemented as would be known to a person having an ordinary level of skill in the art. However, in some embodiments (e.g., where the belt 905 is formed with elastic material), the loop of the belt may be fixed and may not be opened.

In some embodiments, the monomarker 910 comprises a radiopaque material configured to be imaged through conventional 2D imaging techniques, e.g., X-ray imaging. In some embodiments, the radiopaque material comprises one or more of titanium, tungsten, barium sulfate, bismuth compounds, zirconium oxide, and/or additional radiopaque materials as would be known to a person having an ordinary level of skill in the art.

In some embodiments, the monomarker 910 has known characteristics including but not limited to a particular shape and/or size (i.e., dimensions). In some embodiments, the monomarker 910 is spherical and has a known diameter. Alternate shapes for the monomarker 910 are contemplated within the scope of this disclosure. In some embodiments, the monomarker 910 has a diameter of about 26 mm to about 36 mm. In additional embodiments, the monomarker 910 has a diameter of 36 mm, 26 mm, 22 mm, 18 mm, 14 mm, 10 mm, less than 10 mm, or individual values or ranges therebetween. In some embodiments, the diameter of the monomarker 910 is sufficiently small to adequately limit overlay with anatomical structures in the 2D imaging field. For example, a smaller monomarker 910 may have a smaller footprint and thus block a smaller portion of the anatomy, thereby providing clearer visualization of the patient anatomy.

As described herein, in some embodiments the monomarker 910 is secured within the pocket 915, e.g., resiliently retained by the material of the pocket 915. However, alternate means of fastening and/or retaining the monomarker 910 may be used as would be apparent to a person having an ordinary level of skill in the art. In some embodiments, rather than being secured with the pocket 915, the monomarker 910 is secured on a front or back surface of the belt 905. For example, the monomarker 910 may be secured to a rigid or semi-rigid baseplate on a portion of the belt 905. The baseplate may be radio-transparent such that it does not interfere with the detection of the monomarker 910. In some embodiments, the monomarker 910 is removable such that the belt 905 and monomarker 910 may be individually cleaned or sterilized. In some embodiments, the monomarker 910 is embedded or otherwise immovably joined within the belt 905. In some embodiments, the monomarker 910 may be substantially stationary with respect to the belt 905. In some embodiments, the position of the monomarker 910 may be adjustable. For example, adjusting the position of the monomarker 910 may increase patient comfort during imaging.

In some embodiments, the monomarker 910 may be used as described herein without a belt 905. In some embodiments, alternate means may be used for securing the monomarker 910 to the patient. For example, the monomarker 910 may secured to the patient by a clip (e.g., a three-fingered clip), a spring clip, a band, an adjustable strap (e.g., a hook and loop strap), a strip of fabric or other material (e.g., tightened in a knot to secure to the patient), adhesives, and additional means as would be apparent to a person having an ordinary level of skill in the art. In some embodiments, the means for securing the monomarker 910 may secure to a patient's clothing (e.g., an edge of a shirt, an edge of a pair of pants, a belt loop, etc.) in a manner to position the monomarker 910 proximate the pubic symphysis as described herein. In additional embodiments, securing means such as those used in conventional systems may be used to secure the monomarker 910. For example, the monomarker 910 may be attached to an adjustable or articulable arm resting on an imaging table such that it may be positioned proximate the pubic symphysis as described herein by a medical professional. In another example, the monomarker 910 may be attached to a strap affixed to the rigid board on an imaging table. The monomarker 910 may be removably or permanently attached to the securing means. In some embodiments, the monomarker 910 may be positioned with respect to the patient without a securing means. For example, in supine imaging, the monomarker 910 may be placed on top of the patient at or near the pubic symphysis for the duration of imaging.

It should be understood that the dual scale calibration device 900 as described herein may be simply and comfortably placed in the suprapubic region with little effort required by both the patient and the medical professional. Accordingly, the high degree of skill associated with precise fiducial marker placement in conventional systems is alleviated. Further, the invasiveness and unpleasant nature of placing a marker directly between the legs of a patient is avoided. As such, greater care and attention may be given to proper fiducial marker placement while providing greater comfort to the patient.

In some embodiments, the dual scale calibration device 900 may be designed as disposable and configured for one-time use. In some embodiments, one or more components of the dual scale calibration device 900 (e.g., the belt 905 and/or the monomarker 910) may be designed as disposable and configured for one-time use. In some embodiments, one or more components of the dual scale calibration device 900 are designed for re-use and configured for washing, sterilizing, and/or autoclaving.

As described herein, the belt 905 may be formed from a variety of materials. For example, the belt 905 may be formed from fabrics, textiles, polymer materials, natural materials, synthetic materials, and/or combinations thereof. In some embodiments, the belt 905 may include elastic or resilient materials. In some embodiments, the belt 905 may include substantially inelastic materials. In some embodiments, the belt 905 may comprise a plurality of layers of material. For example, the belt 905 may include a plurality of layers of the a material and/or a plurality of layers of different materials, e.g., to provide different material properties in different regions of the belt 905. As described further herein, in some embodiments, the dual scale calibration device 900 may be used to obtain a plurality of 2D images of the patient, e.g., a frontal or A-P 2D image and a lateral 2D image. Accordingly, the belt 905 may be configured to maintain the monomarker 910 in substantially the same position on the patient during the imaging procedure to produce the plurality of 2D images. In some embodiments, the belt 905 may comprise a high-friction material (e.g., a silicone or a rubber) configured to maintain its position and orientation with respect to the patient during imaging, thereby maintaining the monomarker 910 in substantially the same position on the patient. In some embodiments, the belt 905 may comprise a material having adhesive properties (e.g., a silicone adhesive material) configured to temporarily adhere to the patient during imaging, thereby maintaining the monomarker 910 in substantially the same position on the patient. The adhesive characteristic of the material may be sufficient to maintain the position of the belt 905 during imaging but low enough to permit removal of the belt after imaging. Additional materials may be utilized to form the belt 905 to maintain the position of the belt 905 and the monomarker 910 on the patient during imaging as would be apparent to a person having an ordinary level of skill in the art.

In some embodiments, the belt 905 may comprise an inner layer (i.e., on a patient facing surface) formed from a high-friction material, e.g., a silicone or a rubber, configured to maintain its position and orientation with respect to the patient during imaging, thereby maintaining the monomarker 910 in substantially the same position on the patient. In some embodiments, the belt 905 may comprise an inner layer (i.e., on a patient facing surface) formed from a material having adhesive properties (e.g., a silicone adhesive material) configured to temporarily adhere to the patient during imaging, thereby maintaining the monomarker 910 in substantially the same position on the patient. The adhesive characteristic of the material may be sufficient to maintain the position of the belt 905 during imaging but low enough to permit removal of the belt after imaging. Additional materials may be utilized as layers of the belt 905 to maintain the position of the belt 905 and the monomarker 910 on the patient during imaging as would be apparent to a person having an ordinary level of skill in the art.

Method of Imaging Patient with Dual Scale Calibration Device

Figure 11:
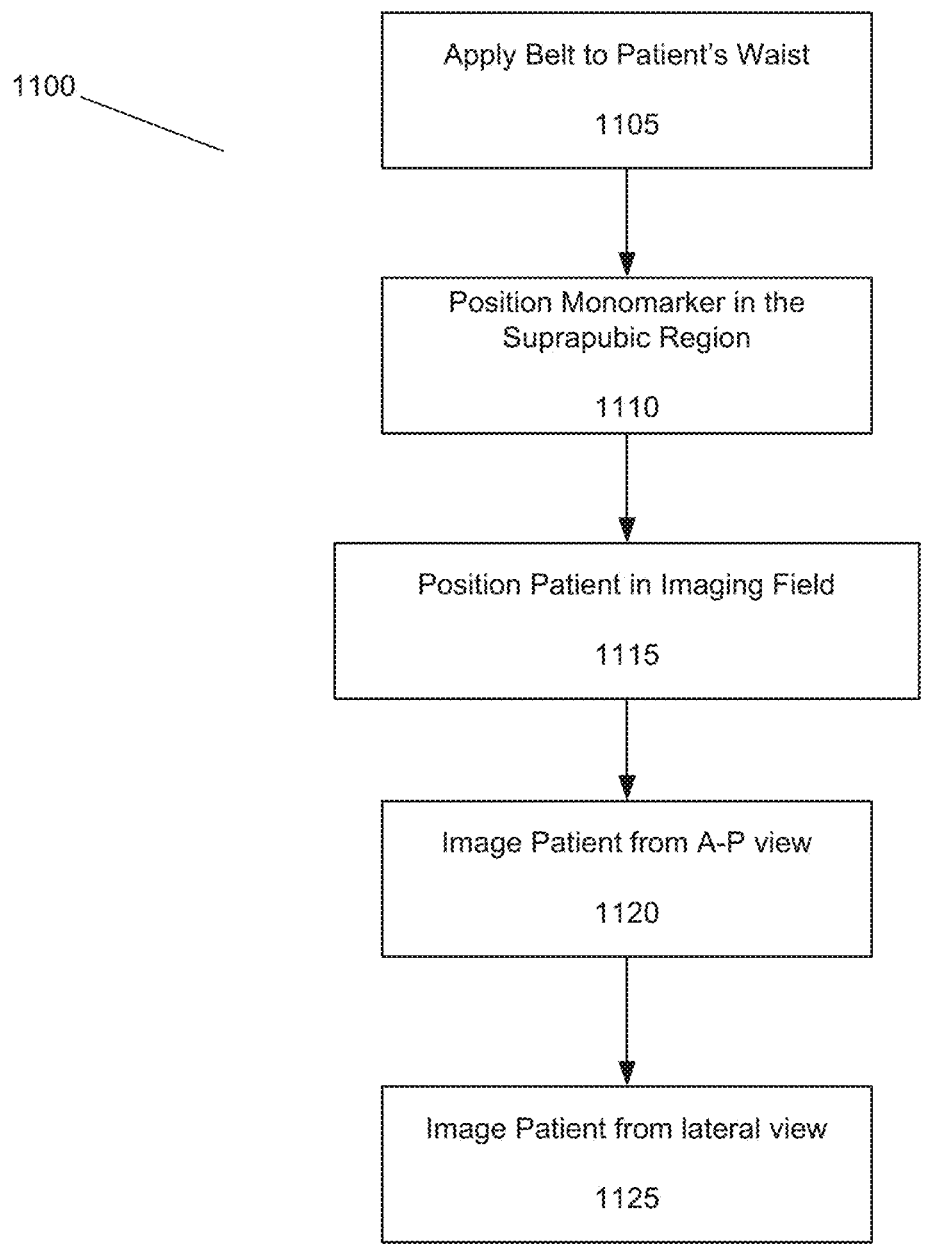
FIG. 11 depicts a flow diagram of an illustrative method 1100 of imaging a patient with a dual scale calibration device in accordance with an embodiment.
Figure 12:
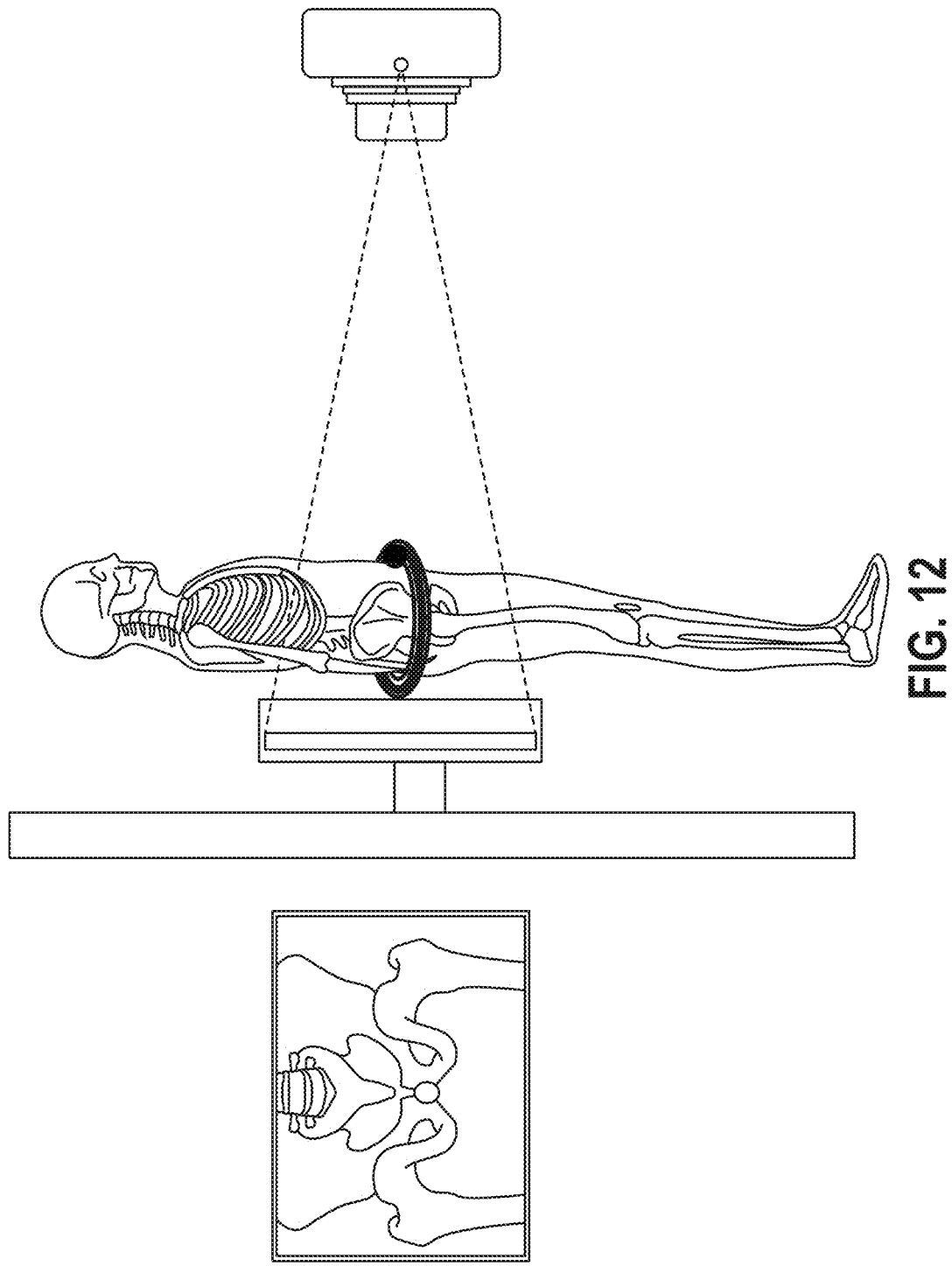
FIG. 12 depicts an exemplary setup for imaging an A-P view of a patient with an imaging system in accordance with an embodiment.
Figure 13:
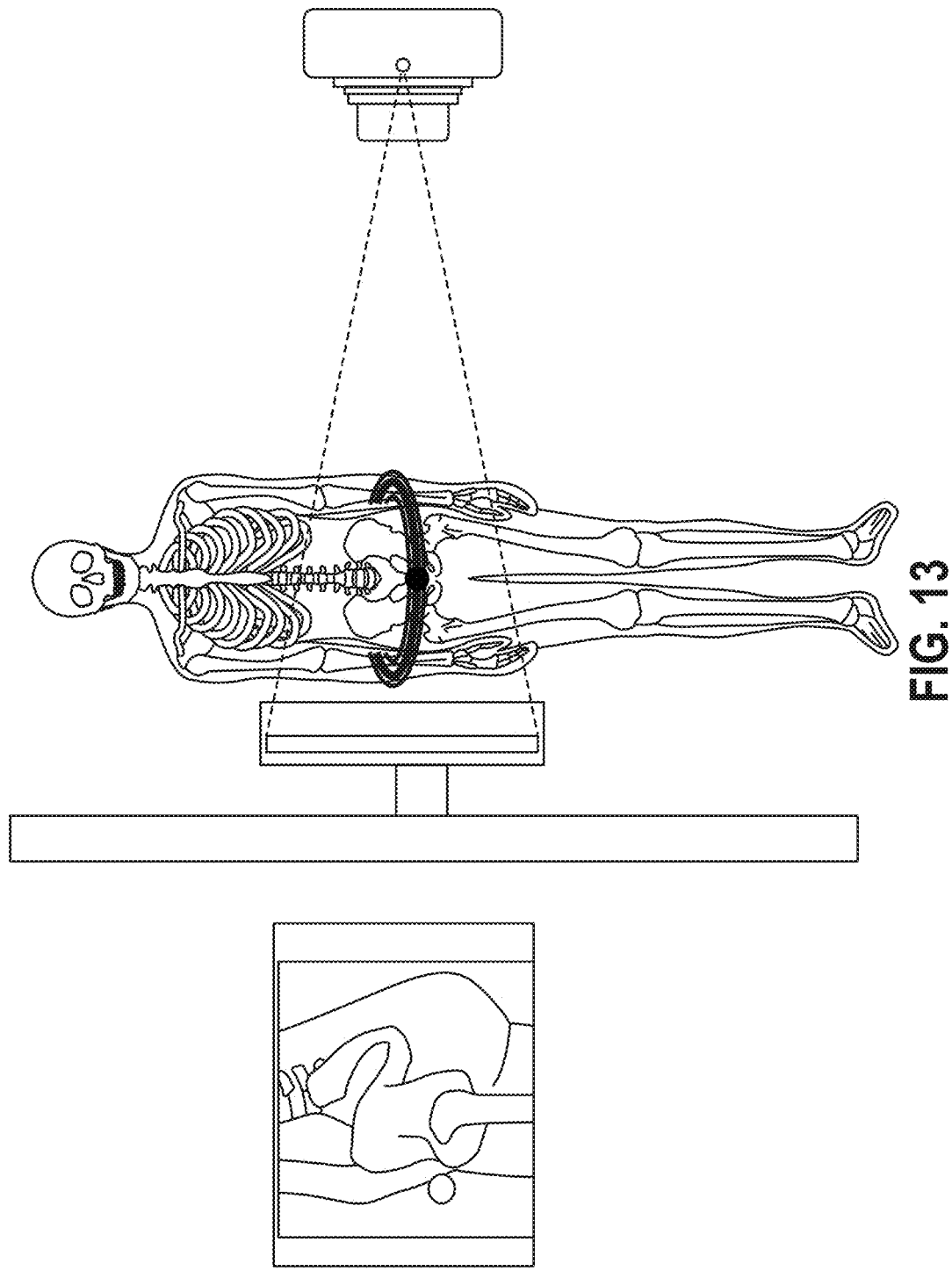
FIG. 13 depicts an exemplary setup for imaging a lateral view of a patient with an imaging system in accordance with an embodiment.

Referring now to FIG. 11, an illustrative method 1100 of imaging a patient with a dual scale calibration device is described in accordance with an embodiment. The method 1100 may be used, for example, according to a dual radiograph calibration approach. The belt may be applied 1105 to the waist, and the monomarker may be placed 1110 on the ventral surface of the patient proximate to the pubic symphysis (i.e., in the suprapubic region). For example, the monomarker may be aligned in front of the pubic symphysis. The patient may be positioned 1115 in an imaging field according to standard procedures. For example, the patient may be placed supine on a table (e.g., in supine X-ray imaging) or with their back against a wall bucky stand (e.g., in standing X-ray imaging). The patient may be imaged 1120 from an anterior-posterior (A-P) view (e.g., as shown in FIG. 12) and may be imaged 1125 from a lateral view (e.g., as shown in FIG. 13). In some embodiments, the monomarker is maintained in substantially the same position on the patient for capturing the A-P view and lateral view images.

In some embodiments, the patient anatomy may be considered when applying 1105 the belt and placing 1110 the monomarker. In some embodiments, the belt position may be adjusted to account for soft tissue of the patient. For example, in the case of an obese patient, fatty tissue in the abdominal region may be present over the suprapubic region. In order to provide greater accuracy in the calculation of the hip plane location as further described herein, it may be preferable to place 1110 the monomarker beneath the fatty tissue in order to be located more proximate to the pubic symphysis (i.e., as opposed to being located over the fatty tissue and thereby at a greater elevation with respect to the pubic symphysis). Accordingly, the belt may be applied 1105 beneath the fatty tissue in the abdominal region and/or slid under the fatty tissue, thereby positioning the monomarker on the ventral surface of the patient proximate to the pubic symphysis.

In some embodiments, placing 1110 the monomarker on the ventral surface of the patient comprises pressing the monomarker into the soft tissue such that the center of the monomarker is located at or near the ventral surface of the patient. The belt may be tightly or snugly applied 1105 around the patient such that the monomarker naturally presses into the soft tissue and maintains its position As further described herein, co-location of the center of the monomarker with the ventral surface of the patient may be advantageous for various calculations. However, in some embodiments, the monomarker may be placed 1110 over the ventral surface such that the entire monomarker sits above the ventral surface of the patient.

In some embodiments, a belt may not be used. For example, the monomarker may be placed 1110 on the ventral surface of the patient proximate in the suprapubic region with other securing means as described herein. In some embodiments, the monomarker may be placed 1110 without securing means and may remain relatively stationary during imaging, e.g., during supine x-ray imaging.

The method 1100 may be performed utilizing a variety of imaging systems as would be apparent to a person having an ordinary level of skill in the art. Exemplary imaging systems that may be used to carry out the method 1100 are depicted in FIGS. 8A-8B. In some embodiments, an imaging system used to carry out the method 1100 as described may have known characteristics. In some embodiments, the imaging system comprises and imaging source and an imaging detector situated about an imaging surface (e.g., an imaging table or a wall bucky stand). In some embodiments, the imaging detector is located at a predetermined distance from the imaging surface. In some embodiments, the imaging system has a known make and model with predetermined specifications. For example, the distance of the imaging detector from the imaging surface may be standard for the make and model of the imaging system. In some embodiments, the distance of the imaging source from the imaging surface and/or the imaging detector may be a predetermined and/or standard distance.

In some embodiments, the method comprises outputting the 2D image as part of an image file. For example, the resulting 2D images may form a portion of a Digital Imaging and COmmunications in Medicine (DICOM) file. In some embodiments, the DICOM file may include additional information. For example, a DICOM file may include header information that identifies or allows for determination of the distance from the relevant surface to the detector. In another example, the DICOM file may identify the model of the imaging system, which may be used to determine the distance based on the imaging system's configuration. In some embodiments, the DICOM file includes information related to the distance of the imaging source (e.g., an X-ray tube/generator) from the detector, which may also be used in furtherance of the calculations described herein as well as additional calculations.

It should be understood that the imaging 1120 from the A-P view and the imaging 1125 from the lateral view may be performed in any order. In some embodiments, the A-P view is captured before the lateral view. In some embodiments, the lateral view is captured before the A-P view. FIGS. 12-13 depict examples of imaging from an A-P view and imaging from a lateral view, respectively, with an imaging system according to some embodiments.

Method of Scaling Images of Patient Captured with Dual Scale Calibration Device

Figure 14:
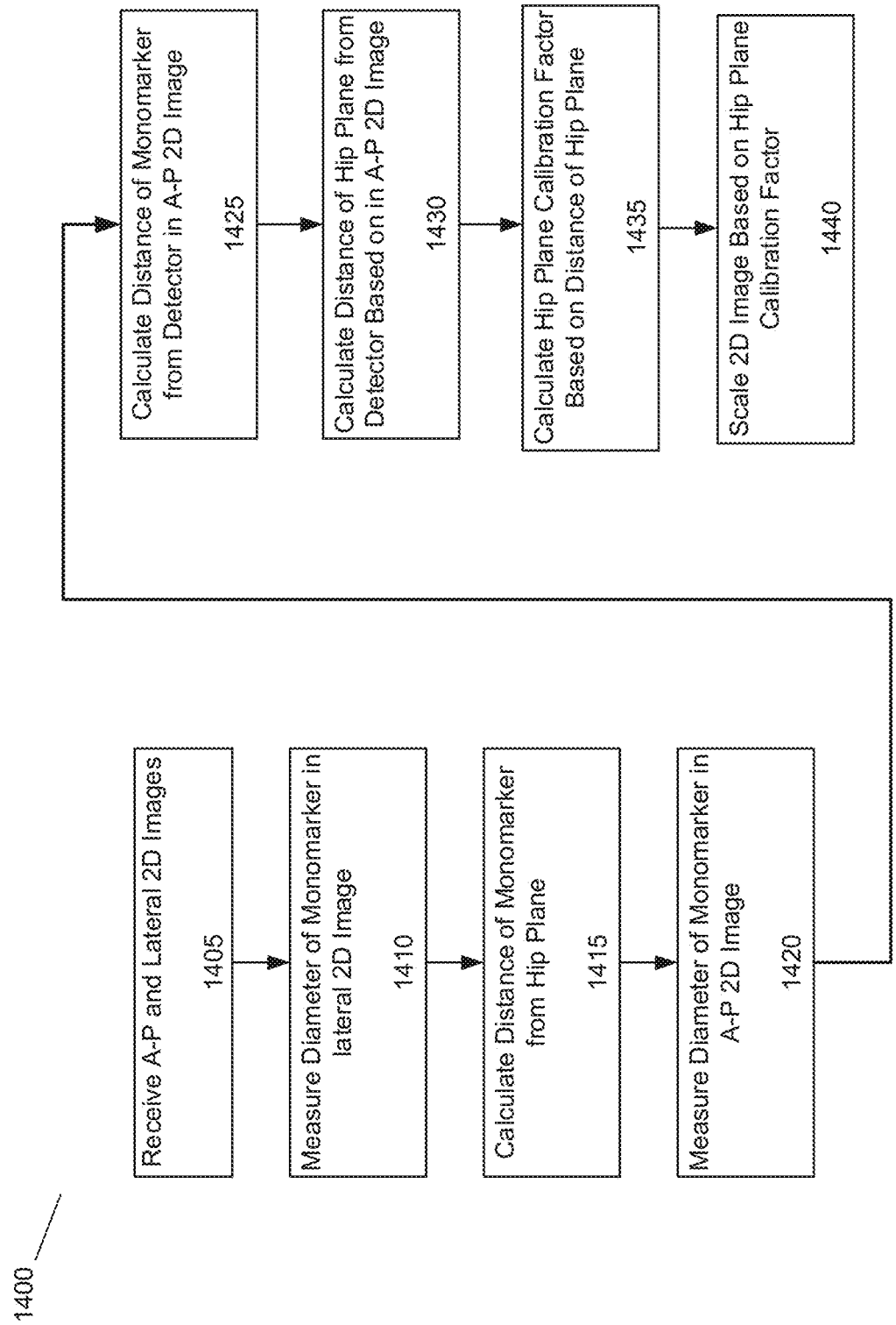
FIG. 14 depicts a flow diagram of an illustrative method of scaling a 2D image in accordance with an embodiment.

Referring now to FIG. 14, a method 1400 of scaling a 2D image is described in accordance with an embodiment. The method 1400 may be used, for example, according to a dual radiograph calibration approach as described with respect to FIG. 11. 2D images of an A-P view and a lateral view of a patient captured with a dual scale calibration device in the manner described herein are received 1405 by a computing device. Using the lateral 2D image, a diameter of the monomarker 1410 in the lateral 2D image is measured 1410 and a distance of the monomarker from the hip plane (hereinafter referred to as $D_{M-HP}$) is calculated 1415 based on the lateral 2D image. Using the A-P 2D image, a diameter of the monomarker in the A-P 2D image is measured 1420 and a distance of the monomarker from the detector of the imaging system (hereinafter referred to as $D_{M-D}$) is calculated 1425. A distance of the hip plane from the detector in the A-P 2D image (hereinafter referred to as $D_{HP-D}$) is calculated 1430 based on $D_{M-HP}$ and $D_{M-D}$. For example, calculating 1430 the $D_{HP-D}$ may comprise subtracting the $D_{M-HP}$ from $D_{M-D}$. Based on the $D_{HP-D}$, a hip plane calibration factor, $CF_{hp}$ (i.e., an indication of the scale of the A-P 2D image with respect to the true anatomy) may be calculated 1435, and the A-P 2D image may be scaled 1440 accordingly to provide an accurately scaled representation of the patient anatomy.

Figure 15:
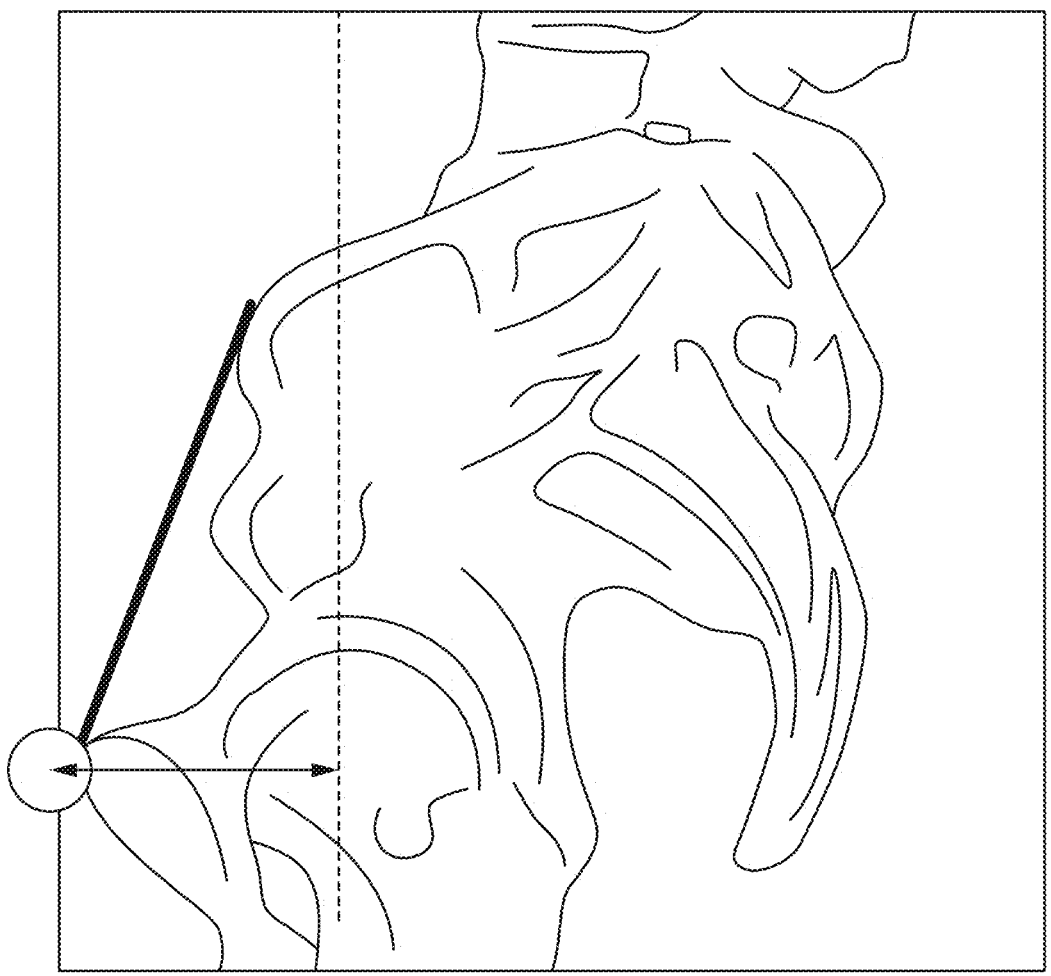
FIG. 15 depicts a lateral 2D image of a patient in accordance with an embodiment.

In some embodiments, the distance of the monomarker from the hip plane in the lateral view (i.e., the $D_{M-HP}$) may be calculated 1415 based on known dimensions of the monomarker. In some embodiments, the distance is calculated 1415 by comparing the diameter of the monomarker in the lateral 2D image to the true diameter of the monomarker to determine a scale of the lateral 2D image. For example, the comparison of the diameter of the monomarker in the 2D image to the true diameter of the monomarker provides a magnification factor according to:

$$m = \frac{\text{Measured diameter}}{\text{True diameter}} \quad (1)$$

where m is the magnification factor. Based on the scale, the $D_{M-HP}$ may be measured on the lateral 2D image because the hip plane is identifiable in the lateral view. For example, FIG. 15 depicts a lateral 2D image of a patient according to an embodiment, where a distance between the monomarker (represented as a circle) and the hip plane (represented as a broken vertical line) is identifiable within the 2D image. In some embodiments, the location of the hip plane may be automatically detected by a computing device, e.g., based on historical imaging data and/or machine learning techniques. In some embodiments, the location of the hip plane may be determined based on user input, e.g., a user may indicate the location of the hip plane through an input device while viewing the lateral 2D image on a display. A measured distance between the hip plane and the monomarker in the lateral 2D image may be scaled based on the calculated magnification factor to determine the true distance $D_{M-HP}$. In some embodiments, the $D_{M-HP}$ may be calculated 1415 with respect to a determined location of the center of the monomarker. In some embodiments, the $D_{M-HP}$ may be calculated 1415 with respect to a determined location of an edge of the monomarker at or near the ventral surface of the patient.

Figure 16A:
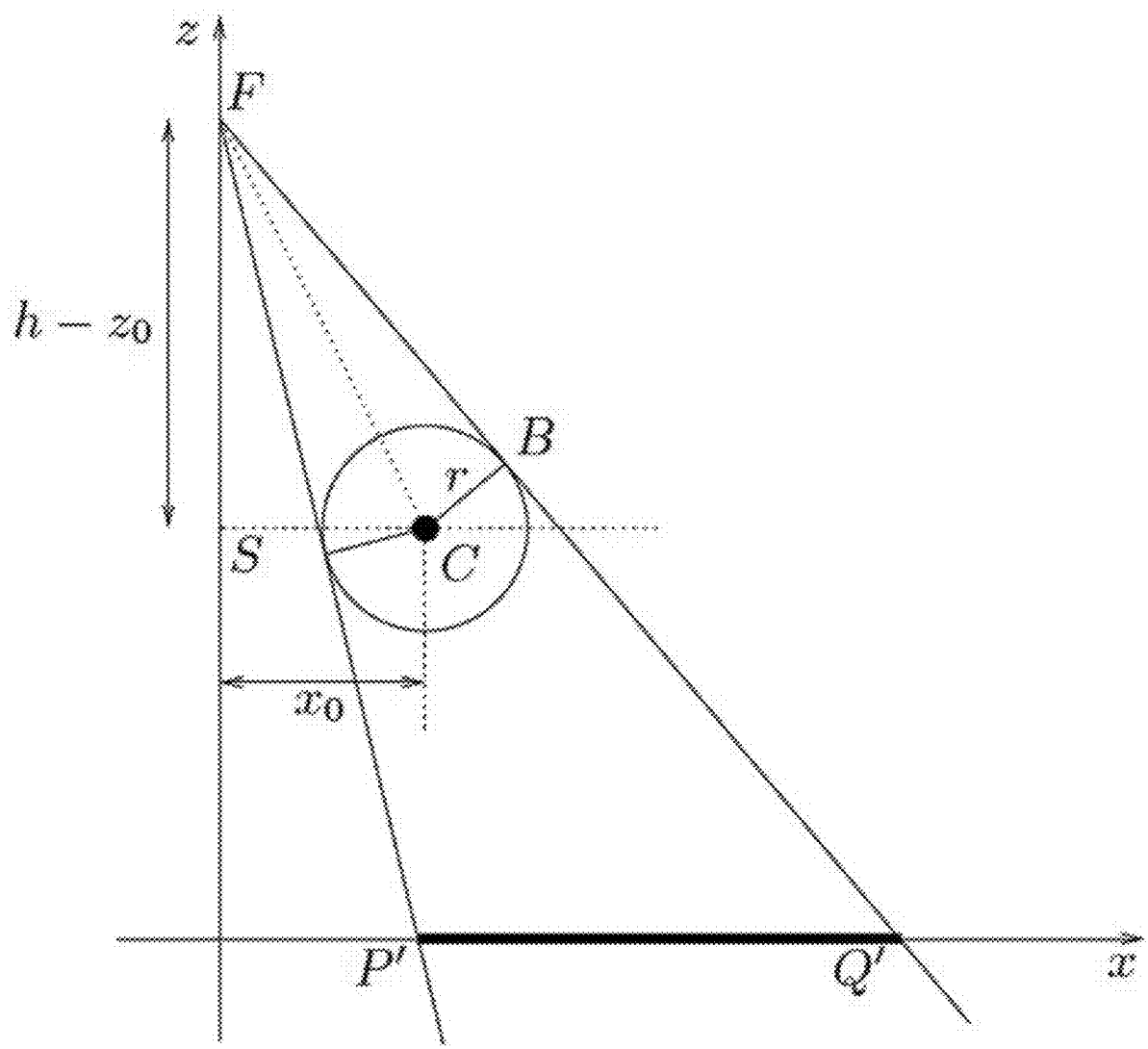
FIGS. 16A-16B depict exemplary diagrams of the projection of a sphere in a radiograph.

In some embodiments, the distance of the monomarker from the detector in the A-P view (i.e., the $D_{M-D}$) may be calculated 1425 based on known dimensions of the monomarker. For example, as described above with respect to $D_{M-HP}$, the distance $D_{M-D}$ may be calculated 1425 by comparing the diameter of the monomarker in the 2D image to the true diameter of the monomarker to determine a magnification factor m for the image using Equation (1). Thereafter, the magnification factor m may be used to solve for $D_{M-D}$ using the intercept theorem:

$$m = CF_z = \frac{h}{h - z_0} \quad (2)$$

where $z_0$ is the distance of the monomarker from the detector plane (i.e., equal to $D_{M-D}$), h is the distance of the imaging source to the imaging detector, and $CF_z$ is the calibration factor at the distance $z_0$ or $D_{M-D}$. As further discussed herein, $z_0$ and/or $D_{M-D}$ generally correspond to a distance of the center of the monomarker from the detector (as shown in FIG. 16A) and is used as an estimation of the distance of the ventral surface of the patient from the detector.

In some embodiments, the distance h may be determined based on a known configuration of the imaging system. For example, while these distances may vary based on the model of the imaging system, in some embodiments, the distance information is included with the 2D image as part of a Digital Imaging and COmmunications in Medicine (DI-COM) file. For example, a DICOM file may include header information that identifies or allows for determination of the distance from the relevant surface to the detector. In another example, the DICOM file may identify the model of the imaging system, which may be used to determine the distance based on the imaging system's configuration. In some embodiments, the DICOM file includes information related to the distance of the imaging source (e.g., an X-ray tube/generator) from the detector, which may also be used in furtherance of the calculations described herein as well as additional calculations. It should be understood that the distances may be determined both in cases of supine imaging, where the detector is fixed to an imaging table, and standing imaging, where the detector is fixed to a wall bucky stand or another patient support. Accordingly, the above equations may be solved for $z_0$ to calculate 1425 the distance $D_{M-D}$.

Once $D_{M-HP}$ and $D_{M-D}$ are calculated as described above, the distance of the hip plane from the detector, $D_{HP-D}$, is calculated 1430 by subtracting $D_{M-HP}$ from $D_{M-D}$:

$$D_{HP-D} = D_{M-D} - D_{M-HP} \quad (3)$$

Based on the $D_{HP-D}$, a hip plane calibration factor, $CF_{hp}$ (i.e., an indication of the scale of the A-P 2D image with respect to the true anatomy) may be calculated 1435 according to the known relationship between the distance of the hip plane and the magnification of the image:

$$CF_{hp} = \frac{h}{h - D_{HP-D}} \quad (4)$$

where $D_{HP-D}$ is the distance of the hip plane from the detector plane and h is the distance of the imaging source to the imaging detector, which is known as described above. Accordingly, the A-P 2D image may be scaled 1440 based on the calculated $CF_{hp}$ to provide an accurately scaled representation of the patient anatomy.

As described herein, in some embodiments, the center of the monomarker is pressed into the soft tissue to be substantially co-located with the ventral surface of the patient. Therefore, the location of the monomarker may be equal to the location of the ventral surface and may be directly used to calculate the $D_{M-HP}$ and the $D_{M-D}$ as described. However, in additional embodiments, the entire monomarker may sit upon and above the ventral surface of the patient. Therefore, the monomarker (i.e., the center of the monomarker) is offset from the ventral surface of the patient by a distance equal to the radius of the monomarker. Accordingly, the calculated distance of the monomarker from the detector may be adjusted by an amount equal to the distance of the monomarker center from the ventral surface. This new value may be used as the distance of the monomarker from the detector for the calculations herein to calculate the distance of the hip plane as described, thereby maximizing the clinical relevance.

In another embodiment, the calculations may be performed without correcting for the offset. The calculation 1415 of the $D_{M-HP}$ in the lateral 2D image and the calculation 1425 of the $D_{M-D}$ in the A-P 2D image may both be performed without correcting for the offset. Thereafter, in the calculation 1430 of the $D_{HP-D}$, the offset in the $D_{M-HP}$ and the $D_{M-D}$ will cancel one another by subtraction. Accordingly, the result may account for the offset without shifting the values of the $D_{M-HP}$ and $D_{M-D}$. In some cases, calculating 1430 the $D_{HP-D}$ as such may provide greater accuracy. For example, it may be likely that the monomarker partially presses into the soft tissue and therefore does not sit entirely above the ventral surface. Accordingly, calculating 1430 the $D_{HP-D}$ as such may substantially account for any depression of the monomarker into the soft tissue without need for determining the degree of depression.

In some embodiments, the method 1400 may be implemented in a system configured to perform each of the described steps. For example, a system may comprise at least one processor and a computer-readable storage medium comprising instructions configured to, when executed, cause the at least one processor to receive A-P and lateral 2D images, measure a diameter of the monomarker in the lateral 2D image, calculate a distance of the monomarker from the hip plane, measure a diameter of the monomarker in the A-P 2D image, calculate a distance of the monomarker from the detector of the imaging system in the A-P 2D image, calculate a distance of the hip plane from the detector, calculate a $CF_{hp}$, and scale the 2D image based on the $CF_{hp}$ to provide an accurately scaled representation of the patient anatomy. In some embodiments, the instructions may cause the processor to carry out additional or alternative steps as described herein.

In some embodiments, the system may further comprise an input device configured to receive the input related to one or more steps of the method 1400. The input device may be implemented in any manner as would be apparent to a person having an ordinary level of skill in the art. It should be understood that the system may prompt a user to provide user input to complete or confirm any number of steps. However, in some embodiments, the process may be further automated by excluding user input. For example, in some embodiments, a system as described herein may retrieve 2D images from a variety of sources, e.g., a remote device or a local storage medium. In some embodiments, the system may measure the diameter of the monomarker, calculate and/or obtain distances, calculate the $CF_{hp}$, and/or scale the 2D image in a semi-automated or entirely automated manner.

Projectional Corrections for Scaling Images of Patient

Figure 16B:
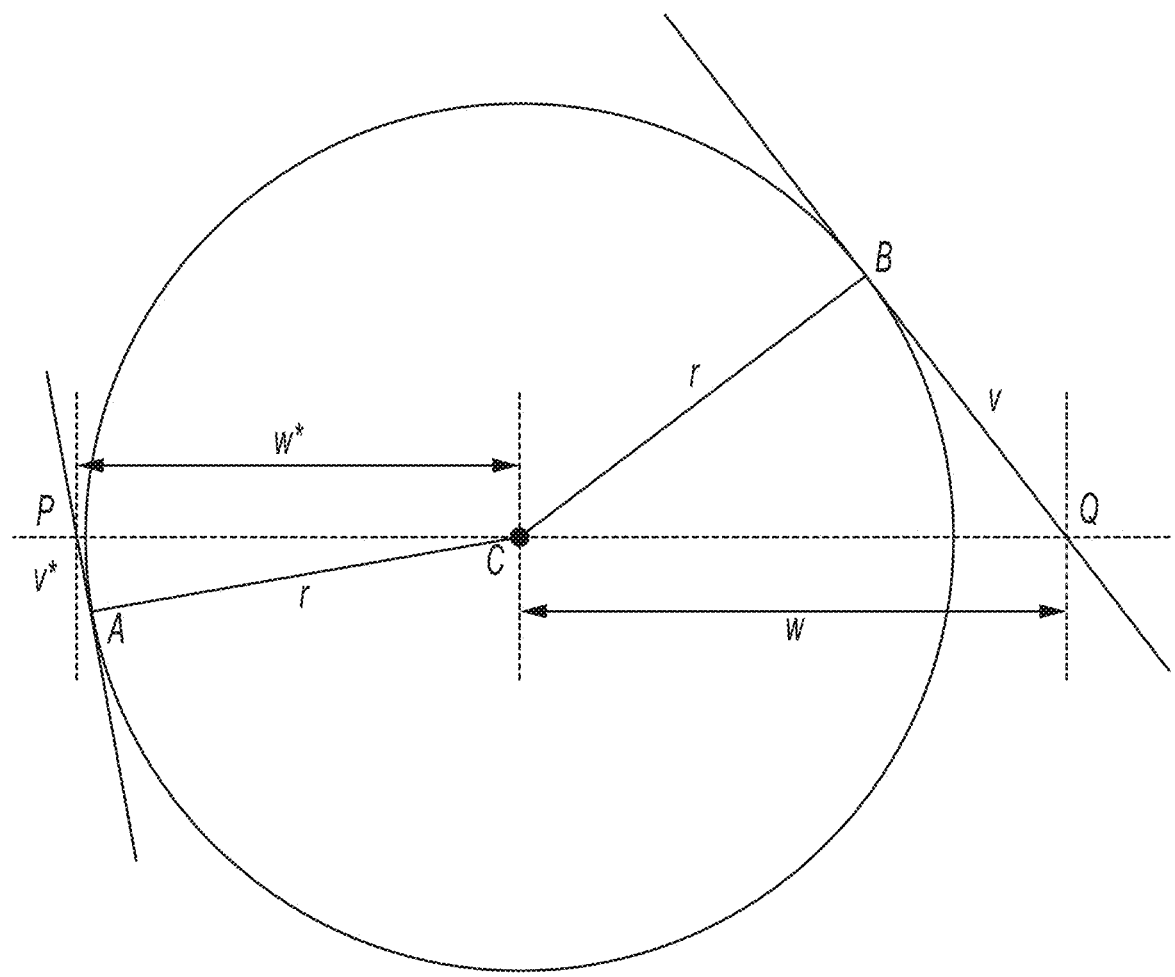

In some embodiments, the determination of $D_{M-HP}$ and/or $D_{M-D}$ as described with respect to the method 1400 may involve further calculation steps to account for projectional effects in the 2D image. In some embodiments, the representation of the monomarker in the 2D image may be distorted based on a distance from the center of the 2D image (i.e., the central beam). For example, a spherical monomarker may appear elliptical. An exemplary diagram of the tangential projection of a sphere in a radiograph is depicted in FIGS. 16A-16B. With reference to FIGS. 14A-14B, the major axis of projection of a sphere is defined by:

$$|P'Q| = m|PQ| = \frac{2rh\sqrt{x_0^2 + (h - z_0)^2 - r^2}}{(h - z_0)^2 - r^2}. \quad (5)$$

where |P'Q'| is the length of the major axis of the projected image (i.e., the diameter of the monomarker measured 1410 in the lateral 2D image or measured 1420 in the A-P 2D image, |PQ| is the distance as shown in FIG. 16B, m is the magnification, $z_0$ is the distance of the monomarker from the detector plane (i.e., equal to $D_{M-D}$), $x_0$ is a horizontal distance of the monomarker from the central beam of the imaging source, h is the distance of the imaging source to the imaging detector, and r is the radius of the monomarker. Accordingly, the projectional effects may be corrected by determining a precise horizontal and vertical position of the monomarker in space based on an inverse formula developed from the above equation:

$$x_0 = \sqrt{\frac{A^2\left[(h-z_0)^2 - r^2\right]^2}{4r^2h^2} - (h-z_0)^2 + r^2} \quad (6)$$

$$z_0 = h - \sqrt{r^2\left(1 + \frac{2h^2}{A^2}\right) + \frac{2rh}{A}\sqrt{\frac{r^2h^2}{A^2} + x_0^2}} \quad (7)$$

where all variables are defined as above and A is equal to |P'Q'|. In some embodiments, the distance $z_0$ or $D_{M-D}$ may be calculated 1425 based on the above formula. In order to perform this calculation, the distance $x_0$ must be known or estimated. In some embodiments, the distance $x_0$ may be measured from the 2D image and used to calculate 1425 the distance $z_0$ or $D_{M-D}$. However, the raw 2D image has not yet been scaled and thus the measured distance $x_0$ may be magnified in the horizontal plane, thus causing a degree of error in the measured distance $x_0$. It should be understood that where the monomarker is properly positioned substantially close to the central beam, the magnification is relatively low and may have a negligible effect on the calculated value of $z_0$ or $D_{M-D}$ by this method. Accordingly, this manner of calculating 1425 may yield a calculated distance $z_0$ or $D_{M-D}$ with an acceptable degree of accuracy that may be used for the subsequent steps of the method 1400 herein.

Figure 17:
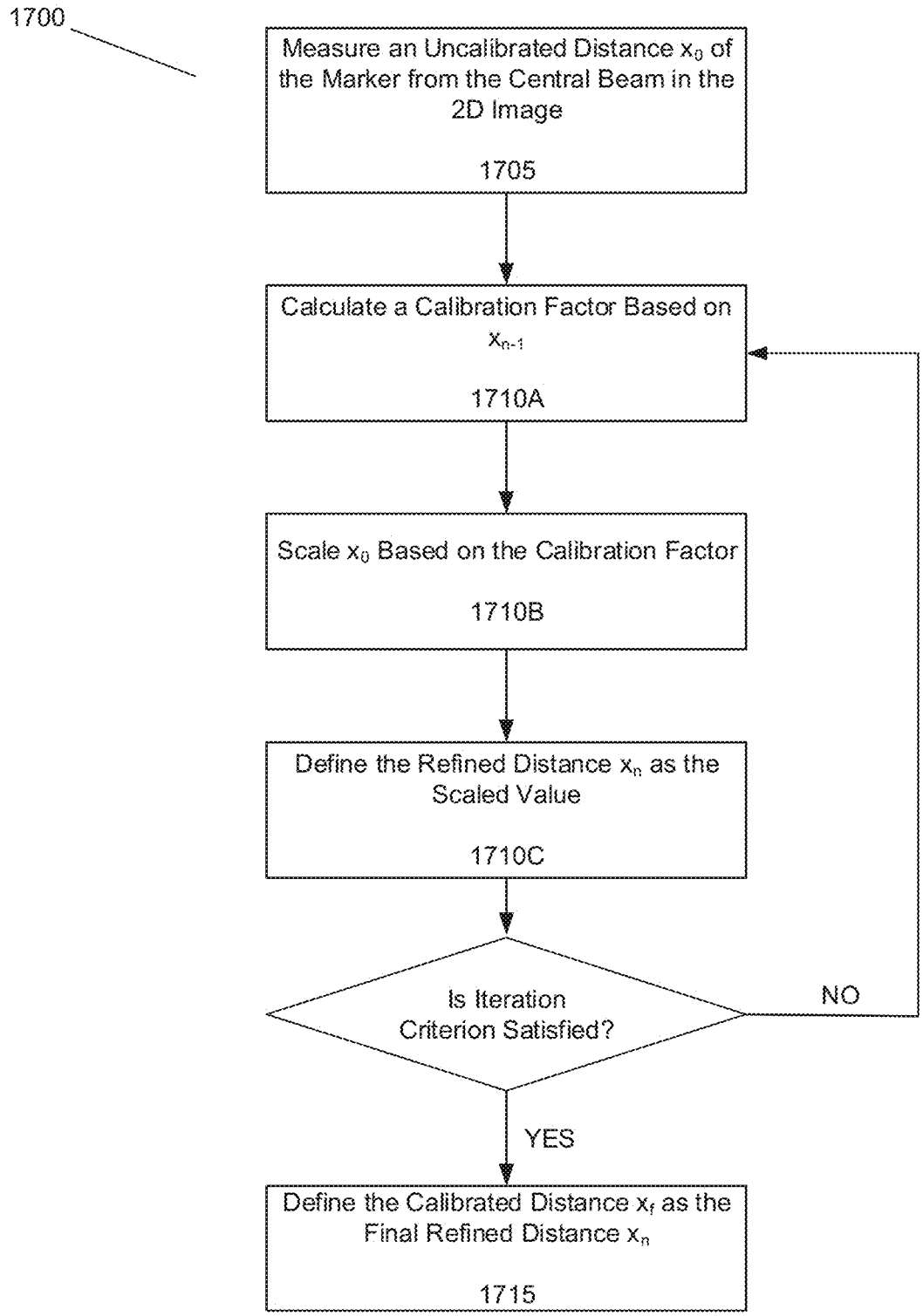
FIG. 17 depicts a flow diagram of an illustrative method of correcting for projectional effects of a monomarker sphere in a 2D image in accordance with an embodiment

However, in some embodiments, the measured value of $x_0$ may be calibrated in order to obtain a more accurate calculation 1425 of the distance $z_0$ or $D_{M-D}$ of the monomarker from the detector. Referring now to FIG. 17, a flow diagram of an illustrative method of correcting for projectional effects of a monomarker sphere in a 2D image is depicted in accordance with an embodiment. The method 1700 may be used to calibrate a measured distance $x_0$ of a monomarker in a 2D image from a central beam of an imaging source. It should be understood that the steps of the method 1700 may be performed as substeps of the calculation 1425 step of the method 1400 as described herein. The method 1700 comprises measuring 1705 an uncalibrated distance $x_0$ from the 2D image and performing 1710 one or more iterations to refine the value of $x_0$, wherein each iteration comprises calculating 1710A a calibration factor based on $x_{n-1}$ where n is equal to the number of the iteration, scaling 1710B the value of $x_0$ based on the calibration factor, and defining 1710C the refined distance $x_n$ as the scaled value. Iterations may be performed 1710 until an iteration criterion is satisfied. Accordingly, where the iteration criterion is not satisfied, the process may return to step 1710A with the iteration number increased by one. Where the iteration criterion has been satisfied, the method further comprises defining 1715 the calibrated distance $x_f$ as the final refined distance $x_n$.

The calibration factor calculated based on x, i.e., $CF_x$, is an approximation of the magnification of the distance $x_0$ in the 2D image. Initially, $CF_x$ may be calculated 1710A by entering $x_0$ and h into the intercept theorem:

$$CF_x = \frac{h}{h - x_0} \tag{8}$$

where $x_0$ is a horizontal distance of the monomarker from the central beam of the imaging source approximated from the 2D image and h is the distance of the imaging source to the imaging detector. The resulting value of $CF_x$ represents an approximated factor by which $x_0$ is magnified.

The uncalibrated distance $x_0$ may be scaled 1710B by the factor $CF_x$ in order to arrive at a scaled value for the distance of the monomarker from the central beam. A refined distance $x_1$ may then be defined 1710C as this scaled value, thereby completing a first iteration.

The refined distance may subsequently be used to perform additional iterations 1710. Each iteration n may comprise calculating 1710A a calibration factor $CF_x$ based on a refined distance $x_{n-1}$ obtained in the previous iteration and scaling 1710B the uncalibrated distance $x_0$ based on $CF_x$. It should be understood that every iteration uses the uncalibrated distance $x_0$ in the scaling 1710B step such that the iterations provide progressively refined scaled values based on progressively refined calibration factors. The iteration is completed by setting the refined distance $x_n$ as the scaled value from the present iteration.

It should be understood that the value of the refined distance $x_n$ and the value of the calibration factor is expected to converge asymptotically towards a limit across the series of iterations. The precise limit may be dependent on several variables, including but not limited to the diameter of the monomarker, the distance h of the imaging source to the imaging detector, the length A of the major axis of the projected image, and the distance $z_0$ or $D_{M-D}$ of the monomarker from the detector. Accordingly, it is contemplated that each subsequent iteration will converge further towards the true calibration factor for the distance $x_0$ in the 2D image.

In some embodiments, iterations may be performed 1710 until an iteration criterion is satisfied. Accordingly, at the completion of each iteration, the iteration criterion may be evaluated to determine the need for an additional iteration as shown in FIG. 17. The iteration criterion may be defined in a variety of manners. In some embodiments, the iteration criterion may be defined by a threshold number of iterations to be performed 1710. In some embodiments, the iteration criterion may be 1 iteration, 2 iterations, 3 iterations, 4 iterations, 5 iterations, 10 iterations, 20 iterations, 30 iterations, 40 iterations, 50 iterations, greater than 50 iterations, or individual values or ranges therebetween. The threshold number of iterations may be selected to provide the degree of accuracy and efficiency in the calculation as desired. For example, due to the asymptotic nature of the iterative process 1710, a predetermined number of iterations may be deemed to provide sufficient accuracy for the calculations herein such that additional iterations may be not be constructive. Accordingly, the predetermined number of iterations may be used as the iteration criterion such that each instance of the method 1700 comprises no more and no less than the predetermined number of iterations.

In some embodiments, the iteration criterion may comprise a threshold amount of correlation between the refined distance $x_n$ of the current iteration and the refined distance $x_{n-1}$ of the previous iteration. In some embodiments, the threshold amount of correlation may comprise a maximum amount of change. For example, due to the asymptotic nature of the process 1710, the threshold amount of correlation may indicate that the change in the refined distance x from the prior iteration to the current iteration is sufficiently small, thereby indicating that the iterative process 1710 has converged on a solution. In some embodiments, the correlation may be measured based on an absolute amount of change in the value of the refined distance x from the prior iteration to the current iteration. In some embodiments, the correlation may be measured based on a percent change in the value of the refined distance x from the prior iteration to the current iteration. Additional measures of correlation may be utilized herein as would be known to a person having an ordinary level of skill in the art. Accordingly, a degree of change below a predetermined amount (i.e., a sufficient amount of correlation) indicates sufficient agreement between consecutive iterations. Conversely, where the degree of change is beyond the predetermined amount, there may not be a sufficient amount of correlation indicating the iterative process 1710 has not yet converged sufficiently.

In some embodiments, the iteration criterion may include multiple criteria such that the determination of whether to perform additional iterations is based upon multiple criteria. For example, the iteration criterion may include a minimum number of iterations performed and a threshold amount of correlation between consecutive iterations.

Upon satisfying the iteration criterion, no further iterations are performed. The calibrated distance $x_f$ is defined 1715 as the refined distance $x_0$ of the final iteration to complete the process. Thereafter, the calibrated distance $x_f$ may then be substituted into the Equation (7) above in place of $x_0$ in order to calculate $z_0$ (i.e., $D_{M-D}$) based on the calibrated distance $x_f$ in the manner described above.

Additional details related to the methodology of correcting for projectional effects are described in Boese C K, Lechler P, Rose L, Dargel J, Oppermann J, et al. (2015), "Calibration Markers for Digital Templating in Total Hip Arthroplasty," PLOS ONE 10(7): e0128529, and Boese C K, Bredow J, Dargel J, Eysel P, Geiges H, Lechler P. (2016), "Calibration Marker Position in Digital Templating of Total Hip Arthroplasty," Journal of Arthroplasty, 31(4):883-887, each of which is incorporated herein by reference in its entirety. Accordingly, the systems and methods described herein allow for greater variation in the placement of the fiducial marker with respect to the patient.

Accordingly, the projectional effects may be accounted for by applying one or more of the series of equations (5) to (8) as described with respect to the method 1700 and FIGS. 16A-16B and 17 to the calculation 1425 of the distance $D_{M-D}$ of the monomarker from the detector. Accordingly, the systems and methods described herein allow for greater variation in the placement of the fiducial marker with respect to the patient. It should also be understood that similar equations may be derived and applied to correct for projectional effects in the lateral 2D image for the purpose of refining the calculation 1415 of the distance $D_{M-HP}$.

Rotational Corrections for Scaling Images of Patient

It should be understood that during the collection of lateral 2D images as described herein with respect to the method 1100 of FIG. 11, a small amount of patient rotation away from the true lateral view (i.e., 90 degrees rotated from the A-P view) in the lateral 2D image may impact the overall calculations. For example, the distance between the monomarker and the hip plane in the 2D image may be distorted because the patient is rotated away from a true lateral view such that the hip plane is not completely orthogonal to the imaging detector. Previously, this impact was considered to be substantially minimal so as to be negligible for the purposes of the calculations of the method 1400 of FIG. 14. Further, it was known that the rotation may be corrected where the rotation angle is known. However, in cases of significant rotation, e.g., 5 degrees of rotation or greater, other factors may accumulate with the rotational offset to create significant calculation errors. Particularly, where the patient orientation is offset from the true lateral view and the positioning of the monomarker is also offset from the pubic symphysis, the distance between the monomarker and the hip plane in the 2D image (i.e., $D_{M-HP}$) may be significantly distorted and impact the measurement 1410 of $D_{M-HP}$ in the method 1400. Furthermore, the combination of these offsets may complicate the process of determining the rotation angle in order to enable correction.

Figure 18A:
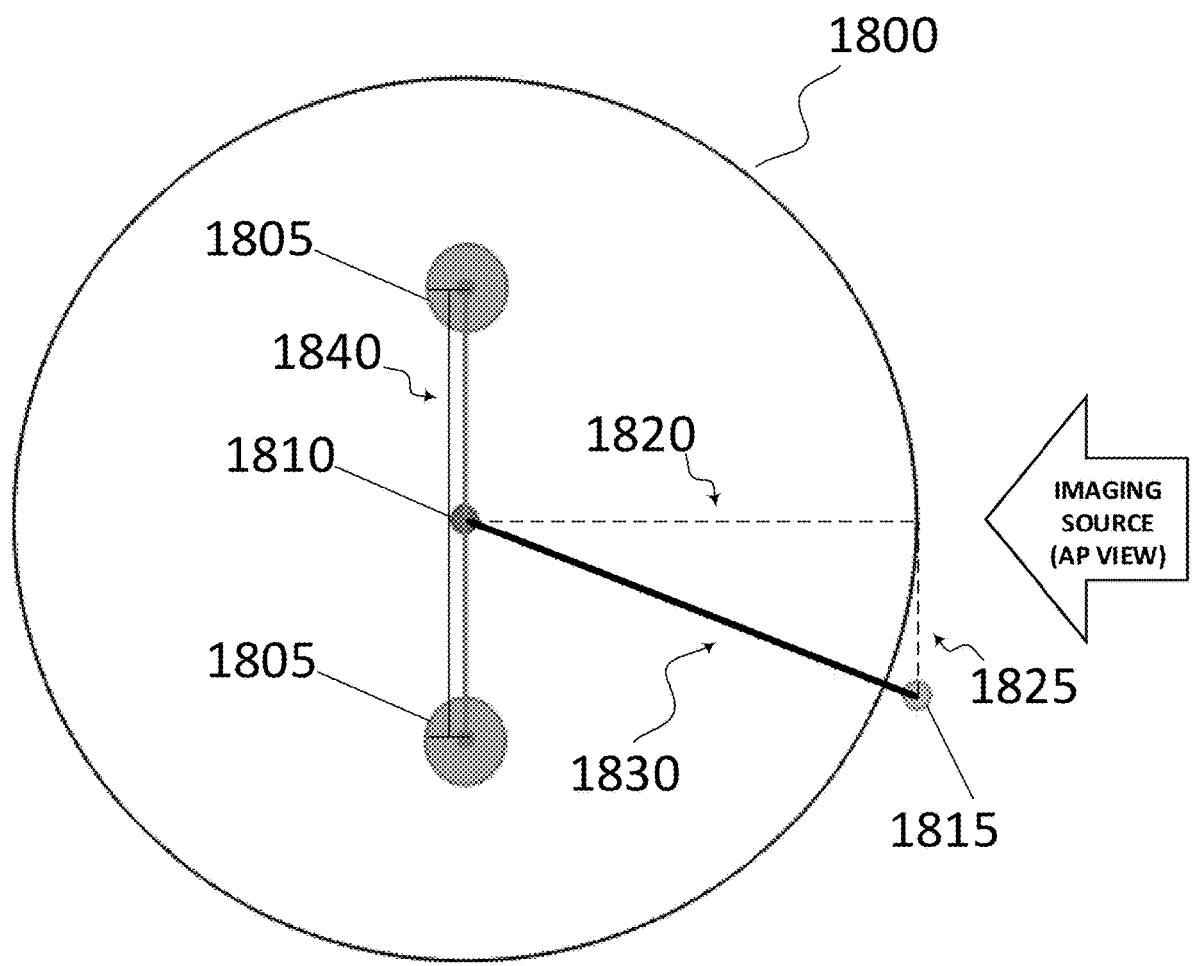
FIG. 18A depicts a top-down view of a patient with an offset monomarker is depicted in accordance with an embodiment.

Referring now to FIG. 18A, a top-down view of a patient with an offset monomarker is depicted in accordance with an embodiment. As shown, the patient 1800 is initially positioned for imaging from the A-P view, i.e. with the hip plane (depicted herein as a line between the hip centers 1805 and the pelvic center 1810) facing the imaging source. Ideally, the monomarker 1815 may be positioned at the midline of the patient over the pubic symphysis (depicted as broken line 1820 in FIG. 18A) and thus substantially centered in the A-P view over the pelvic center 1810. However, as shown, the monomarker 1815 may be positioned with a lateral offset 1825 from the pubic symphysis, such that the monomarker 1815 is located at a distance 1830 from the pelvic center 1810. Although the monomarker 1815 is depicted as being laterally offset towards the right side of the patient 1800, it should be understood that the monomarker 1815 may be laterally offset towards either the left or right side of the patient 1800 due to a variety of factors including but not limited to imprecision during placement of the monomarker 1815, improper securement of the monomarker 1815, and/or an expected degree of movement between the patient anatomy and the monomarker 1815, e.g., due to movement of soft tissue and flexibility in the securing components (e.g., see belt 905 of the dual calibration device 900 of FIGS. 9A-9C). It should also be understood that the monomarker 1815 may likewise be offset in the superior or inferior directions. However, superior or inferior offsets may not materially affect the calculation of $D_{M-HP}$ and are not considered herein.

Figure 18B:
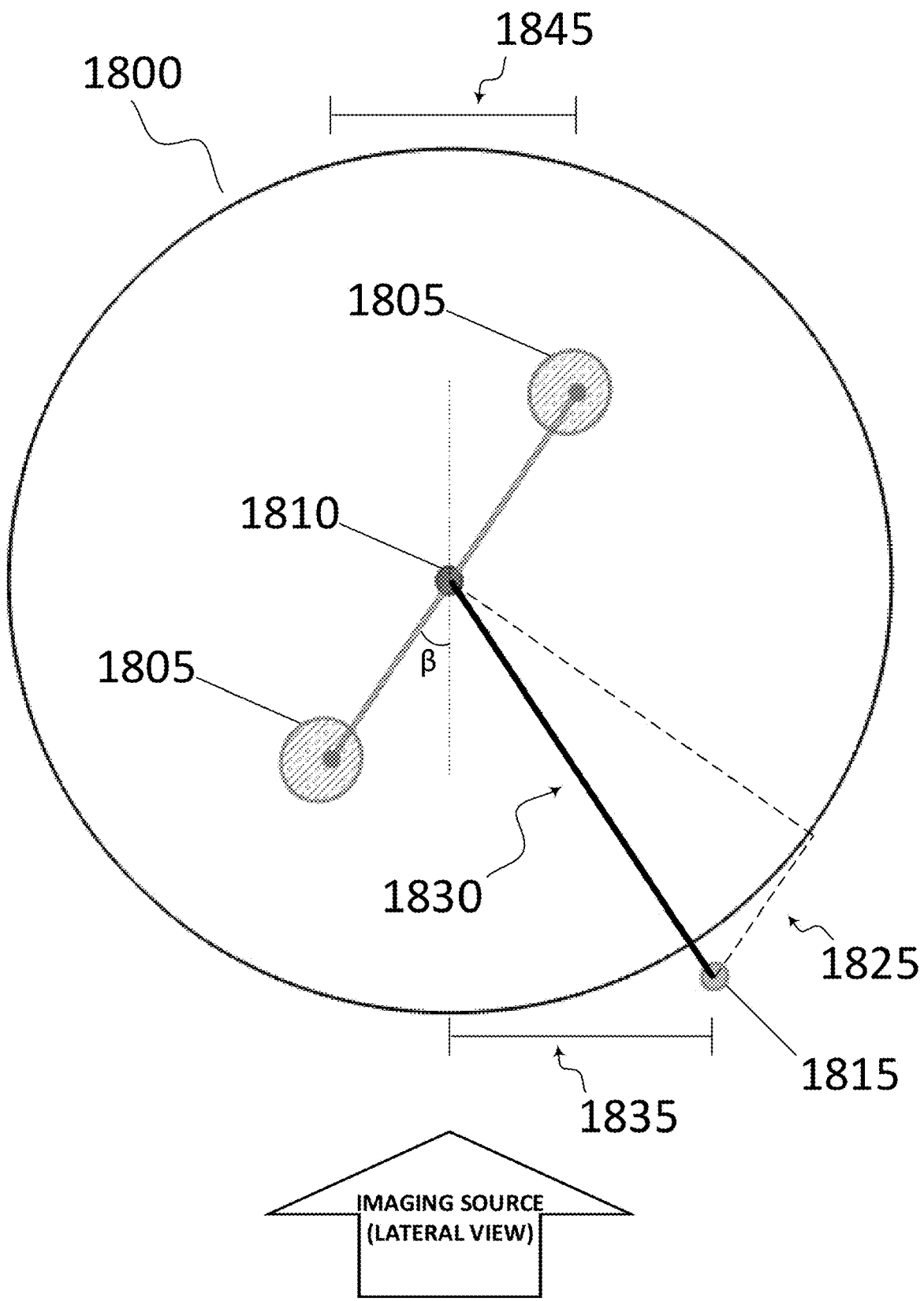
FIG. 18B depicts a top-down view of a patient with an offset monomarker and a rotational offset from the true lateral view for 2D imaging is depicted in accordance with an embodiment.

Referring now to FIG. 18B, a top-down view of a patient with an offset monomarker and a rotational offset from the true lateral view for 2D imaging is depicted in accordance with an embodiment. As shown, the patient 1800 is rotated to a position for imaging from the lateral view. Ideally, the patient is rotated to a true lateral view, i.e., with the hip plane (depicted herein as a line between the hip centers 1805 and the pelvic center 1810) rotated 90 degrees from the A-P view such that the hip plane is parallel to a direction of imaging. However, as shown, the patient 1800 may be rotationally offset from the true lateral view. Furthermore, because the lateral 2D image provides a flattened view of the patient anatomy, the rotational offset compounds with the lateral offset 1825 of the monomarker 1815 and may cause the monomarker 1815 to appear significantly nearer to the pelvic center 1810. For example, the lateral 2D image may depict the monomarker 1815 as being a distance 1835 from the pelvic center 1810, thereby distorting the distance $D_{M-HP}$ that may be measured in the 2D image (see, for comparison, FIG. 18A).

Figure 19:
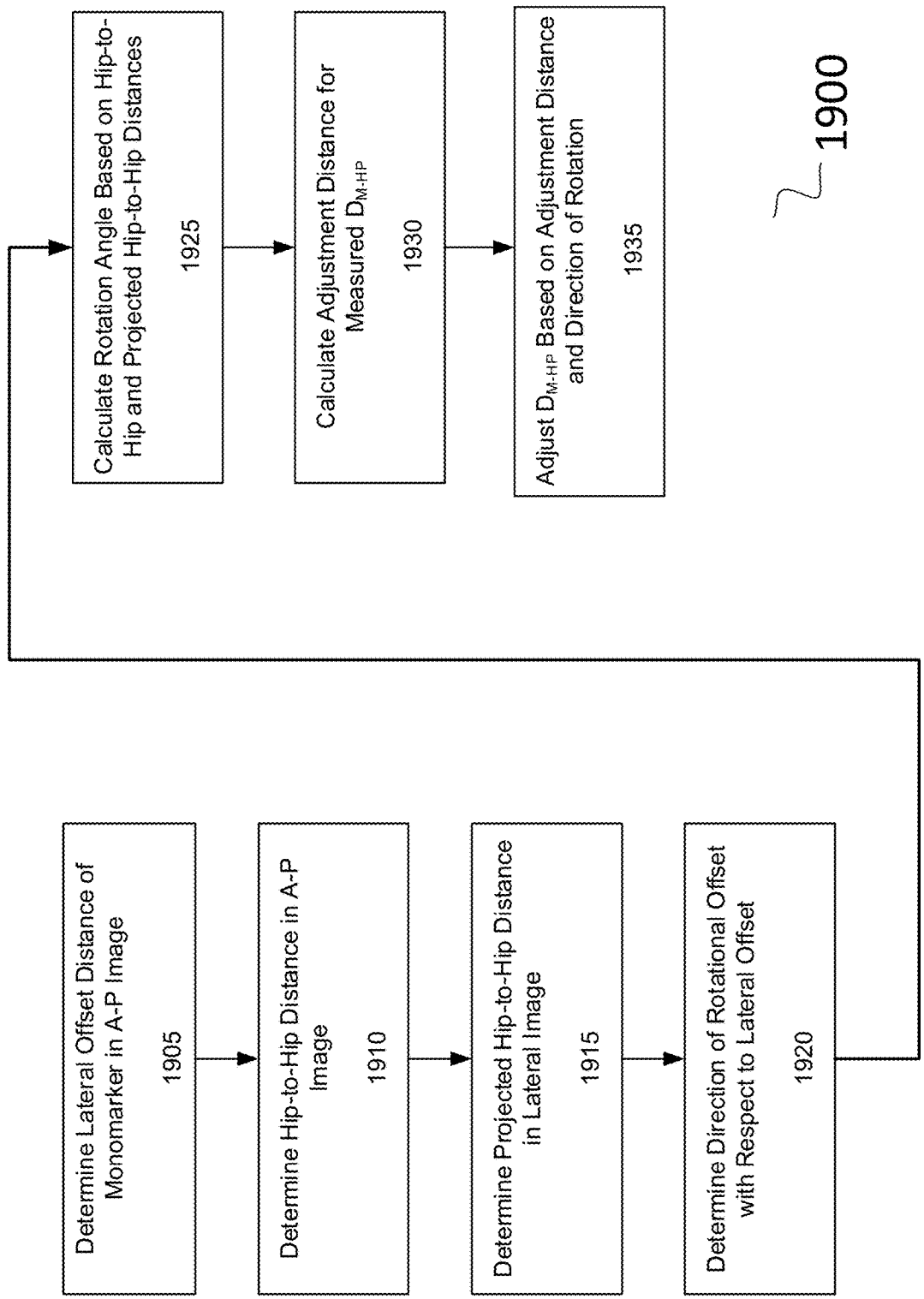
FIG. 19 depicts a flow diagram of an illustrative method of correcting for rotational effects of a patient in a 2D image is depicted in accordance with an embodiment.

Referring now to FIG. 19, a flow diagram of an illustrative method of correcting for rotational effects of a patient in a 2D image is depicted in accordance with an embodiment. As described with respect to the method 1400, a measured distance between the hip plane and the monomarker in the lateral 2D image may be scaled based on the calculated magnification factor to calculate 1415 the true distance $D_{M-HP}$. The method 1900 described herein may be used to correct this distance $D_{M-HP}$ of the monomarker due to rotational offset of the patient and lateral offset of the monomarker. It should be understood that the steps of the method 1900 may be performed as substeps of the calculation 1415 step of the method 1400 as described herein. The method 1900 comprises determining 1905 a lateral offset of the monomarker 1815 in an A-P 2D image, determining 1910 a distance between the hip centers 1805 in the A-P 2D image, determining 1915 a projected distance between the hip centers 1805 in the lateral 2D image, and determining 1920 a direction of rotational offset of the patient 1800 with respect to the lateral offset of the monomarker 1815 in a lateral 2D image. The method 1900 further comprises calculating 1925 a rotation angle β based on the distance between the hip centers and the projected distance between the hip centers, calculating 1930 an adjustment to a measured distance $D_{M-HP}$ between the monomarker and the hip plane based on the rotation angle and the lateral offset of the monomarker, and adjusting 1935 the measured distance $D_{M-HP}$ based on the calculated adjustment and the determined direction of the rotational offset.

In some embodiments, the lateral offset may be equivalent to x as described herein with respect to the method 1700. Accordingly, in some embodiments, one or more steps of the method 1700 may be performed as part of step 1905 in order to correct for projectional effects in the A-P 2D image due to the lateral offset of the monomarker 1815. In some embodiments, the complete method 1700 is performed as part of step 1905. It should be understood that where methods 1700 and 1900 are incorporated into the method 1400, the measurement of the lateral offset in the A-P 2D image and determination of x may only be performed once, and the determined value may be used for multiple calculations as described.

In some embodiments, the lateral offset is measured from the center of the monomarker 1815 to the central beam of the A-P 2D image. In some embodiments, the lateral offset is measured from the center of the monomarker 1815 to the midline (i.e., the pelvic center) in the A-P 2D image. It should be understood that typically, the midline is substantially aligned with the central beam in the A-P 2D image and thus these two measurements may be substantially equivalent.

In some embodiments, the distance between the hip centers 1805 (i.e., a hip-to-hip distance) may be determined 1910 by measuring the distance in the A-P 2D image. For example, as shown in FIG. 18A, the distance between hip centers 1840 may be clearly visible therein. In some embodiments, the A-P 2D image may be substantially undistorted by any rotational offset because positioning for the A-P 2D image is generally accurate and uniform. For example, the patient 1800 may be lying flat on an imaging table or standing flat against a wall, bucky stand, or other support as described herein. Accordingly, it may be assumed that the distance 1840 between the hip centers in the A-P 2D image is substantially undistorted by rotational offsets. Thus, the hip-to-hip distance 1840 may be directly measured in the A-P 2D image. In additional embodiments, the hip-to-hip distance may be determined 1910 by other means. For example, the distance 1840 may be determined from historical images of the patient, from stored anatomical information related to the patient, and the like. In some instances, a hip-to-hip distance obtained from another source may be scaled to represent the approximate distance 1840 in the A-P 2D image. For example, a physically measured distance between the hips of the patient may be scaled down to represent a distance 1840 in the A-P 2D image based on a known magnification factor as described herein.

In some embodiments, the projected distance between the hip centers 1805 may be determined 1915 from the lateral 2D image. As shown in FIG. 18B, the distance 1845 between the hip centers 1805 may be visible and may be directly measured on the lateral 2D image.

In some embodiments, a direction of rotational offset of the patient 1800 in a lateral 2D image may be determined 1920 based on the lateral 2D image. It should be understood that an absolute direction of the rotational offset is not necessarily relevant in this case. Rather, the direction with respect to the direction of the lateral offset of the monomarker 1815 is necessary for the calculations. Accordingly, it may be sufficient to determine whether the rotational offset is in the same direction as the lateral offset or in an opposing direction from the lateral offset. Knowledge of this directional relationship may be relevant to the adjustment of the distance $D_{M-HP}$ because the relationship may affect the sign or direction of the adjustment. For example, where the rotation of the patient moves the monomarker 1815 in the same direction as the lateral offset (i.e., towards or away from the imaging source), the effect of the offsets is compounded. Accordingly, where the rotational and lateral offsets are in the same direction (i.e., +/+ or −/−), the adjustment may be positive, i.e., adding the adjustment value to the measured distance $D_{M-HP}$. In another example, where the rotation of the patient moves the monomarker 1815 in an opposite direction from the lateral offset, the effect of the offsets may partially cancel one another. Accordingly, where the rotational and lateral offsets are in opposite directions, (i.e., +/− or −/+), the adjustment may be negative, i.e., subtracting the adjustment value from the measured distance $D_{M-HP}$. This calculation is discussed in greater detail with respect to step 1935 herein.

In some embodiments, the direction of rotational offset is determined 1920 based on a size of the features of each hip in the lateral 2D image. For example, where the features of one hip are slightly larger than the other hip, the larger hip may be assumed as the near hip during imaging and may be used to assess the direction of rotation.

In some embodiments, the direction of rotational offset is determined 1920 based on distinct anatomical features or abnormalities associated with a particular hip. For example, a known distinguishable anatomical feature of one of the hips may be used to distinguish the hips in the lateral 2D image, thereby providing directional information that may be used to assess the direction of rotation. In some embodiments, the distinguishable anatomical feature may be known or identified based on the A-P 2D image. In some embodiments, the distinguishable anatomical feature may be known or identified based on historical medical information associated with the patient and/or historical images of the patient.

In some embodiments, the direction of rotational offset is determined 1920 based on visible foreign bodies in the lateral 2D image. For example, a foreign body, such as an implant, plate, screw, or the like, with a known location near of one of the hips may be used to distinguish the hips in the lateral 2D image, thereby providing directional information that may be used to assess the direction of rotation. In some embodiments, the known location of the foreign body may be known or identified based on the A-P 2D image. In some embodiments, the known location of the foreign body may be known or identified based on historical medical information associated with the patient and/or historical images of the patient.

In some embodiments, directional markers may be provided on or near the patient during imaging to assist in distinguishing the hips in the lateral 2D image to determine 1920 the direction of rotational offset. Although the monomarker 1815 may be the sole fiducial marker for the purpose of scaling, additional directional markers may be provided solely for determining direction of rotation. Accordingly, the directional markers are qualitative and are not used for quantitative measurements or calculations in the manner of the monomarker 1815. Thus, the directional markers may be less robust, less costly, and may not significantly impact the comfort of the patient. In some embodiments, the directional markers may be adhered to the skin of the patient near the hips. For example, directional markers may be placed at or near the anterior superior iliac spine. In some embodiments, the directional markers may be secured to the patient along with the monomarker 1815, e.g., such as by the dual scale calibration device 900. For example, directional markers may be provided at the sides of the belt 905. In some embodiments, at least one directional marker is applied to a single hip and may be sufficient to distinguish the hips in the lateral 2D image. In some embodiments, at least one direction marker is applied to each of the hips to distinguish the hips in the lateral 2D image. In some embodiments, the directional markers comprise distinct shapes from one another to distinguish therebetween. In some embodiments, the directional markers comprise distinct sizes from one another to distinguish therebetween. Additional manners of distinguishing between directional markers are contemplated herein as would be apparent to a person having an ordinary level of skill in the art.

In some embodiments, the monomarker 1815 may be provided with additional features to assist in distinguishing the hips in the lateral 2D image to determine 1920 the direction of rotational offset. For example, the monomarker 1815 may comprise one or more relatively small protruding features such as antennae, e.g., at a side or sides, such that rotation of the monomarker in either direction is distinguishable in the lateral 2D image. Accordingly, the protruding features may be assessed to determine 1920 the direction of rotational offset.

In some embodiments, the patient may purposely be placed at an angle in order to assist in determining 1920 the direction of rotational offset. For example, markers or guides may be provided on the floor (e.g., marked on the floor or provided on a mat) or elsewhere in the imaging space to direct a slight rotational offset of the patient. In another example, the rotational offset may be accomplished by providing handles or bars at a predetermined orientation for the patient to hold. In another example, visual or haptic feedback may be provided to obtain the predetermined orientation of the patient. In some embodiments, the markers or guides may indicate the patient's feet to be positioned to provide a predetermined degree of rotation in a specific direction. Accordingly, the rotational offset may be known based on this guidance during imaging. It should be noted that while positioning the patient in the true lateral view may be easily overlooked by an imaging technician or medical professional, specific guidance to be placed at an offset angle is more likely to be carefully noted and followed during the imaging procedure. In some embodiments, the markers or guides may also indicate additional desired features of the pose of the patient. For example, the markers or guides may indicate for the patient to internally rotate the feet and hold this pose during imaging. The markers or guides may include supports to assist the patient in holding the pose during imaging.

Figure 20:
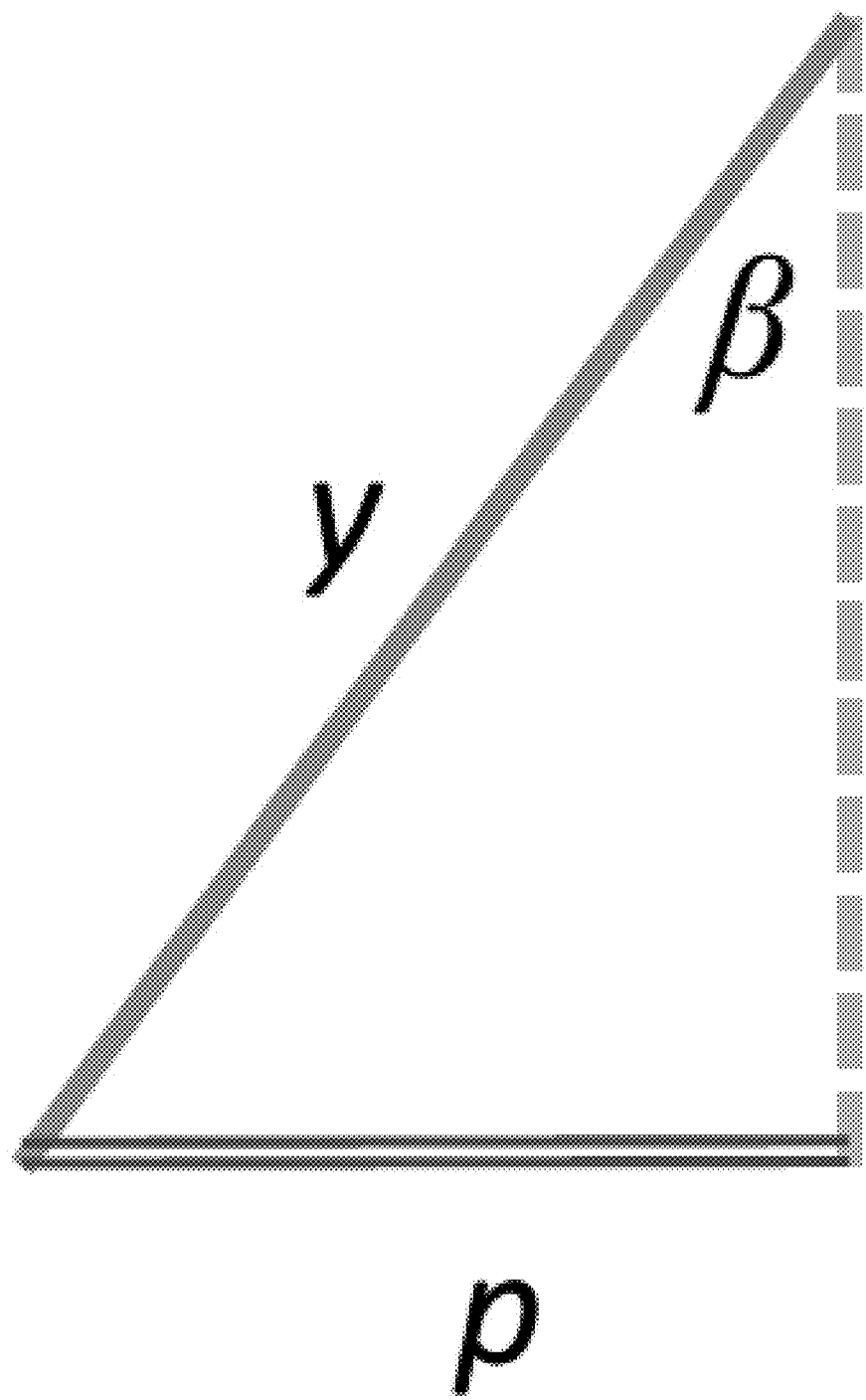
FIG. 20 depicts the relationship between the hip-to-hip distance and the projected hip-to-hip distance in accordance with an embodiment in an image collected as shown in FIG. 18B.

In some embodiments, the rotation angle β may be calculated 1925 based on the distance 1840 between the hip centers and the projected distance 1845 between the hip centers. For example, FIG. 20 depicts the relationship between the distance 1840 between the hip centers and the projected distance 1845 between the hip centers in accordance with an embodiment. Accordingly, the rotation angle β may be calculated 1925 according to the following equations:

$$\sin(\beta) = \frac{\text{Opposite}}{\text{Hypotenuse}} = \frac{p}{y} \qquad (9)$$

$$\beta = a\sin\frac{\text{Opposite}}{\text{Hypotenuse}} = a\sin\frac{p}{y} \qquad (10)$$

where p is the projected distance 1845 between the hip centers and y is the distance 1840 between the hip centers in the 2D images. It should be understood that while the angle β is calculated 1925 according to FIG. 20 based on the full distance 1840 between the hip centers and the full projected distance 1845 between the hip centers, the angle β may also be calculated 1925 by halving these distances (i.e., to represent a proportional right triangle between the pelvic center 1810 and one of the hip centers 1805) to yield the same result.

Figure 21:
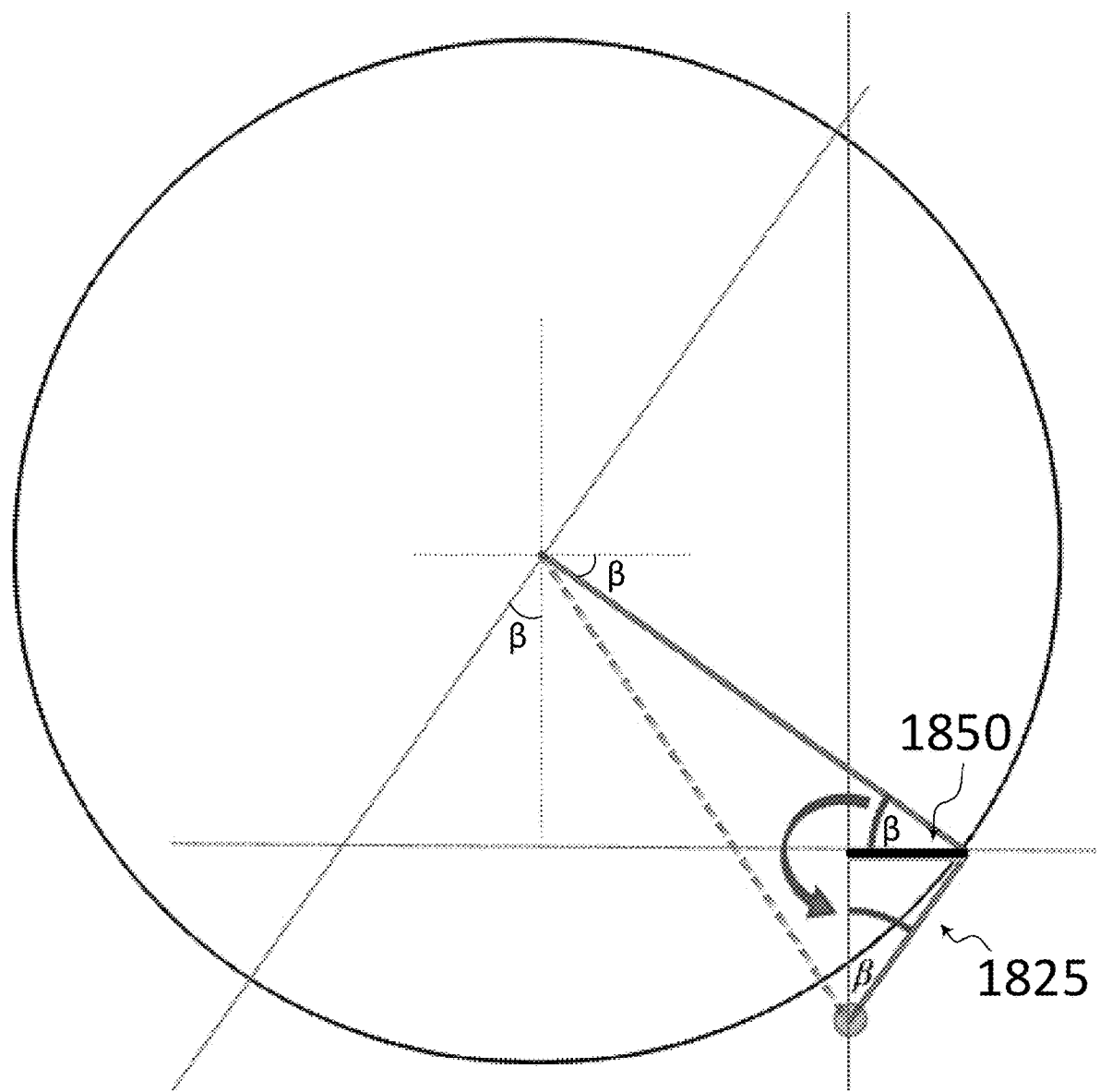
FIG. 21 depicts the relationship between the rotation angle and the lateral offset distance in an image collected as shown in FIG. 18B in accordance with an embodiment.

In some embodiments, the adjustment to a measured distance $D_{M-HP}$ between the monomarker and the hip plane may be calculated 1930 based on the lateral offset of the monomarker 1815 as determined in step 1905 and the rotational angle as determined in step 1925. The adjustment distance 1850 may be a distance by which the measured distance $D_{M-HP}$ may be increased or reduced to correct for the rotational and lateral offsets. For example, FIG. 21 depicts the relationship between the adjustment distance 1850, the rotation angle β, and the lateral offset distance 1825 in accordance with an embodiment. As shown, the angle β may be trigonometrically reflected in a right triangle formed between the lateral offset 1825 and the adjustment distance 1850. Accordingly, the adjustment distance 1850 may be calculated 1930 according to the following equation:

$$A = \sin(\beta) \times L \qquad (11)$$

where A is the adjustment distance 1850, β is the rotation angle, and L is the lateral offset distance 1825. It should be understood that the relationship between these measurements is trigonometric and thus the adjustment distance 1850 may be calculated 1930 in a variety of mathematically equivalent manners to yield the same result.

In some embodiments, the measured distance $D_{M-HP}$ may be adjusted 1935 up or down by the adjustment distance 1850 calculated according to step 1930. In some embodiments, the adjustment is based on the relative direction of rotation determined in step 1920. For example, where the rotational and lateral offsets are in the same direction (i.e., +/+ or −/−), the adjustment may be positive, i.e., adding the adjustment value to the measured distance $D_{M-HP}$. Accordingly, the adjustment distance 1850 may be added to the measured distance $D_{M-HP}$. In another example, where the rotational and lateral offsets are in opposite directions, (i.e., +/− or −/+), the adjustment may be negative, i.e., subtracting the adjustment value from the measured distance $D_{M-HP}$. Accordingly, the adjustment distance 1850 may be subtracted from the measured distance $D_{M-HP}$. The adjusted value of $D_{M-HP}$ may sufficiently correct and/or compensate for the rotational and lateral offsets in the 2D images as described herein.

It should be understood that the measurements and calculated values in the method 1900 are relative to the 2D images. Accordingly, the utilized measurements and calculated distances are unscaled. This does not cause mathematical errors because all distances are substantially equally unscaled, thereby allowing for proper calculation of the relative measurements. However, the final adjusted value of $D_{M-HP}$ may thereafter be used in the manner outlined in the method 1400 and thus scaled in the manner described therein for the final calculation of $CF_{hp}$.

It should be understood that the method 1900 may ideally be used to correct for rotational offsets that are not negligible for the purposes of the method 1400. In some embodiments, the method 1900 may be used to correct for a rotational offset of about 5 degrees or greater. For example, the method 1900 may be used to correct for a rotational offset of about 5 degrees, about 6 degrees, about 7 degrees, about 8 degrees, about 9 degrees, about 10 degrees, about 15 degrees, about 20 degrees, about 30 degrees, about 40 degrees, about 50 degrees, greater than about 50 degrees, or individual values or ranges therebetween.

In some embodiments, the method 1900 may be omitted where the rotational offset is less than about 5 degrees. For example, a lateral 2D image with a rotational offset of less than about 5 degrees may be used for the method 1400 without correcting for rotational offset as described herein. In another example, one or more steps of the method 1900 may be performed to determine a rotational offset angle and, where the rotational offset is less than about 5 degrees, the lateral 2D image may be used for the method 1400 without completing the method 1900 and without correcting for rotational offset as described herein. In some embodiments, the method 1900 may also be used to correct for rotational offsets of less than 5 degrees. For example, measurements in a lateral 2D image with a rotational offset of greater than about 0 degrees and less than about 5 degrees may be corrected using the method 1900 as described herein. Correcting for rotational offset in these cases may nonetheless provide great accuracy in the calculations performed based on the lateral 2D image.

In some embodiments, the method 1900 may be omitted where the rotational offset is about 0 degrees. For example, a lateral 2D image with substantially no rotational offset may be used for the method 1400 without correcting for rotational offset as described herein. In another example, one or more steps of the method 1900 may be performed to determine a rotational offset angle and, where the rotational offset about 0 degrees, the lateral 2D image may be used for the method 1400 without completing the method 1900 and without correcting for rotational offset as described herein.

The devices, systems, and methods as described herein are not intended to be limited in terms of the particular embodiments described, which are intended only as illustrations of various features. Many modifications and variations to the devices, systems, and methods can be made without departing from their spirit and scope, as will be apparent to those of ordinary skill in the art.

While the devices, systems and methods are described and depicted with respect to a pelvis and a hip joint, in some embodiments, the systems and methods may be applied to additional parts of the anatomy. In some embodiments, the systems as described may be utilized with conventional imaging methods in order to image and scale 2D images of additional anatomical regions. For example, the dual scale calibration device 900 may be modified to be secured around an upper leg of a patient (e.g., by using a smaller belt or other securing means) such that the monomarker may be positioned between the legs substantially at an approximate depth of the hip plane as required by conventional methods. Accordingly, the known dimensions of the monomarker may be used to determine a distance to the hip plane and scale the 2D image accordingly as would be apparent to a person having an ordinary level of skill in the art. The manner of securing the monomarker to the patient around the leg or by other means may provide greater comfort to the patient and eliminate at least some of the invasiveness associated with conventional systems.

In some embodiments, the methods 1400, 1700, and/or 1900 may be implemented through a software application on a computing device. For example, a user may be able to import 2D images and provide input information to scale the 2D image according to the methods described herein. For example, a user may input and or adjust information such as the dimensions of the monomarker, the distance of the imaging surface from the detector, the distance of the monomarker from the image center, demographic information or other patient information for the calculations as described herein, and the like. However, the software application may automatically determine various pieces of information from additional sources (e.g., a database and/or information from the 2D images). In some embodiments, the software application may be configured to transmit the scaled 2D images to a variety of external systems as described herein, e.g., a bone modeling system, an implant planning system, a simulation system, a storage device, and/or a database.

In some embodiments, the methods as described may be utilized with conventional fiducial marker systems in order to image and scale 2D images of additional anatomical regions. For example, the systems and methods may be modified as would be apparent to a person having an ordinary level of skill in the art to imaging a leg, an arm, and/or a thorax. The systems and methods may be used to plan surgical procedures and/or design implants related to a shoulder, an elbow, an ankle, a hip, a knee, or the like, within the scope of this disclosure. For example, the dual scale calibration device 900 may be modified to be secured around a shoulder, an elbow, an ankle, a hip, a knee, or the like (e.g., by using a smaller belt or other securing means) and may thus be used to image and accurately scale 2D images of these anatomical regions.

In some embodiments, the systems and methods are utilized with supine 2D imaging (e.g. a supine X-ray system depicted in FIG. 8A). In some embodiments, the systems and methods are utilized with standing 2D imaging (e.g., a standing X-ray system depicted in FIG. 8B). In some embodiments, the patient may be immobilized during 2D imaging with respect to the detector. For example, in standing 2D imaging, the patient may be strapped or otherwise immobilized against the wall bucky stand. In some embodiments, it may not be necessary to immobilize the patient with respect to the detector.

In some embodiments, additional 2D images may be acquired to improve the accuracy of the calculations. For example, an oblique view of the patient anatomy may be captured in additional to the A-P and lateral views. In another example, the lateral view may be substituted with an oblique view at a substantially predetermined angle, thereby simplifying the process of identifying an orientation of the patient as described herein. In some embodiments, the lateral view may be substituted with an oblique view captured without a predetermined angle. Accordingly, the method 1900 may be used to correct for rotational offset in the oblique view to calculate the necessary distances therein. Additional views may also provide information related to the position of the hip plane that can be further incorporated into the calculations.

In some embodiments, the scaled 2D images may be used for anatomy modeling, digital templating, and/or surgical planning including but not limited to implant selection and implant design. In some embodiments, the scaled 2D images may be used to create a patient-specific 3D bone model that can be used in furtherance of surgical planning and/or implant selection. Furthermore, in some embodiments, the devices, systems and methods described herein may also be integrated and/or used in conjunction with various surgical platforms and/or planning tools. For example, a surgical platform or planning tool may be configured to receive 2D images and detect features to scale the 2D images as described herein.

In some embodiments, the devices, systems, and methods described herein may be used in conjunction with a bone modeling system. For example, the dual scale calibration device may be used during imaging and the resulting 2D images may be used with a system for constructing three-dimensional bone models as described in International PCT Patent Application No. PCT/US2020/066357, filed on Dec. 21, 2020, entitled "Three-Dimensional Selective Bone Matching from 2D Image Data," which is incorporated herein by reference in its entirety. As fully described therein, one or more images of a patient bone may be scaled, aligned, and oriented with one or more template bone images and/or historical bone images. Where the dual scale calibration device 900 is used during imaging, the 2D images may be scaled by the method described herein. For example, historical bone images may include a representation of the monomarker if acquired using the dual scale calibration device as described herein such that the representation of the monomarker in the 2D images may be directly compared to the previously scaled historical bone images. In another example, where a representation of the monomarker is not present in the historical bone images, the known dimensions of any features within the historical bone images may be compared to the known dimensions of the monomarker to properly scale the 2D images. In another example, a 3D rendering of a marker may be superimposed on the historical bone images and adjusted to an accurate scale based on the known dimensions of the historical bones for comparison with a monomarker in the 2D images.

Furthermore, because the monomarker has known dimensions, the representation of the monomarker in the 2D images may be used as a reference point to infer various dimensions of the anatomy. In some embodiments, the monomarker and/or any anatomical features of known or inferred dimensions in the 2D images may be compared to features of known dimensions in the historical bone images.

In some embodiments, where the historical bone images were collected using the dual scale calibration device 900 described herein, the representation of the monomarker in each image may be used to scale the images with respect to one another as described herein. In some embodiments, the dimensions of the representation of the monomarker in the 2D images may be utilized to identify closely matching historical bone images (e.g., dimensions of the representation of the monomarker in the 2D images may substantially correlate to a size or girth of the patient). Demographic information and additional information as described herein may also be used to identify closely matching historical bone images. In some embodiments, the bone modeling system may be used with the scaled 2D images to identify closely matching historical 2D images having a treatment plan (e.g., implant sizing information) associated therewith. The treatment plans of closely matching historical 2D images may be predictive of a treatment plan for the current patient.

The inferences and comparisons as described may be used to produce a three-dimensional bone model of the patient bone with more accurate scaling. In some embodiments, the bone modeling system may be configured to scale the 2D images as described herein. For example, the bone modeling system may receive the raw 2D images of the patient and may be configured to scale the 2D images based on the representation of the monomarker in the 2D images. In some embodiments, the bone modeling system may receive user input through a user interface in order to scale the 2D images. In some embodiments, the bone modeling system may be configured to automatically detect the monomarker in the 2D images and scale the 2D images accordingly by the methods described herein. In some embodiments, the bone modeling system may compare the 2D images to historical images and/or template images from a library of scaled 2D images. The dual calibration device 900 and the resulting information and calculations as described herein may be utilized with a database of historical images and/or bone modeling software in additional manners as would be apparent to a person having an ordinary level of skill in the art.

In some embodiments, additional information from the 2D images may be obtained and used to more accurately produce a three-dimensional model. The additional information from the 2D images may include one or more dimensions of one or more features of the patient anatomy in the scaled 2D image. For example, the features of the patient anatomy may include the centers of the femoral heads (e.g., approximated as spheres), the pelvic teardrops, the ischial points, and/or the trochanters. Further non-limiting examples of features for a hip joint are the iliac spines, the anterior superior iliac spine (ASIS), iliac points, the lowest point of the ischiatic bone, the greater trochanter, the lesser trochanter, the acetabulum, the saddle points, the acetabular roof, the obturator foramen, the pubic symphysis, the sacrum, the sacrococcygeal joint, the femoral shaft, the ischial tuberosity, and/or a center of rotation. Further, the additional information may include a distance between features of the patient anatomy in the scaled 2D image, e.g., a length of a line between two features, and/or an angle between features of the patient anatomy, e.g., an angle formed between three features or points of interest. For example, the additional information may comprise a length of a line between femoral heads, an inter-ischial line, an inter-trochanteric line, a teardrop line, a femoral offset, a global offset, a pelvic incidence, and/or an anterior pelvic inclination. In embodiments where A-P and lateral views of the hip are imaged, a greater number of features of the patient anatomy, dimensions thereof, and/or distances therebetween may be identified.

In some embodiments, the devices, systems and methods described herein may be used in conjunction with an implant planning system. For example, the dual scale calibration device may be used during imaging and the resulting 2D images may be used with PRESTO planning software from SMITH & NEPHEW, INC. PRESTO generally uses a combination of demographic information for the patient such as gender, age, height, weight, and body mass index (BMI) to predict an implant size for planning an arthroplasty procedure. In some embodiments, the implant planning system may receive information from the scaled 2D images (e.g., one or more dimensions of the patient anatomy) as an additional input in the prediction model. In some embodiments, the implant planning system may receive the scaled 2D images directly and identify information or dimensions therein to determine the additional inputs. The additional inputs may yield greater accuracy in the implant predictions. In some embodiments, the planning system may be configured to scale the 2D images as described herein. For example, the implant planning system may receive the raw 2D images of the patient and may be configured to scale the 2D images based on the representation of the monomarker in the 2D images. In some embodiments, the implant planning system may receive user input through a user interface in order to scale the 2D images. In some embodiments, the implant planning system may be configured to automatically detect the monomarker in the 2D images and scale the 2D images accordingly by the methods described herein.

The implant planning system may compare the demographic information and additional information from the 2D images to identify historical patients having similar characteristics. Based on the implant selection and outcomes from the similar historical patients, the implant planning system may predict an implant size and/or implant make and model for the patient. Accordingly, precisely scaled images may provide the most accurate dimensions for implant prediction during surgical planning.

The additional information from the 2D images may include one or more dimensions of one or more features of the patient anatomy in the scaled 2D image. For example, the features of the patient anatomy may include the centers of the femoral heads (e.g., approximated as spheres), the pelvic teardrops, the ischial points, the trochanters, and/or additional features as described above with respect to the bone modeling system. Further, the additional information may include a distance between features of the patient anatomy in the scaled 2D image, e.g., a length of a line between two features, and/or an angle between features of the patient anatomy, e.g., an angle formed between three features or points of interest as described above with respect to the bone modeling system. In embodiments where A-P and lateral views of the hip are imaged, a greater number of features of the patient anatomy, dimensions thereof, and/or distances therebetween may be identified.

In some embodiments, the devices, systems and methods described herein may be used in conjunction with a simulation system. For example, the dual scale calibration device may be used during imaging and the resulting 2D images may be used with RI.HIP MODELER simulation and planning software (also referred to as HipPRO) from SMITH & NEPHEW, INC, which is an application that may be implemented on a personal computer, tablet, mobile device, or other computing device. RI.HIP MODELER generally uses 2D images to evaluate a patient's desired range of motion and optimize implant orientation (e.g., acetabular cup orientation) for a selected make, model, and size of implant. RI.HIP MODELER may identify one or more landmarks in one or more 2D images (e.g., sitting and standing x-rays) and assess one or more features of the patient anatomy such as one or more dimensions of features and/or one or more angles between landmarks (e.g., a sacral slope). RI.HIP MODELER may condition an anatomical model to mimic the mobility of a patient based on the one or more angles and simulate various activities to determine a desired range of motion. Based on the desired range of motion and the selected make, model, and size of the implant, RI.HIP MODELER may evaluate various acetabular cup orientations with respect to the patient anatomy to provide a range of motion encompassing all or portions of the desired range of motion in an optimal manner. In addition to the information associated with the patient, RI.HIP MODELER may use information associated with the particular selected implant. For example, the particular implant set may comprise characteristics and/or a unique range of motion signature (e.g., a specific range and/or specific limitations on the range. Accordingly, information associated with the particular selected implant set may be considered for evaluating acetabular cup orientations in the context of simulated activities. The features and functions associated with RI.HIP are described in detail in International PCT Patent Application No. PCT/US2021/051435, filed on Sep. 22, 2021, entitled "Systems and Methods for Hip Modeling and Simulation," which is incorporated herein by reference in its entirety.

In some embodiments, the simulation and planning system may receive the scaled 2D images as described herein and use the scaled 2D images to assess features of the patient anatomy. In some embodiments, the simulation and planning system may be configured to receive the raw 2D images and scale the 2D images as described herein based on the representation of the monomarker in the 2D images. In some embodiments, the simulation and planning system may receive user input through a user interface in order to scale the 2D images. In some embodiments, the simulation and planning system may be configured to automatically detect the monomarker in the 2D images and scale the 2D images accordingly by the methods described herein. In some embodiments, the simulation and planning system may receive raw or scaled 2D images electronically from a local or remote computing device (e.g., a database). In some embodiments, the simulation and planning system may receive raw or scaled 2D images by image capture through a camera communicating with the computing device (e.g., a camera of a mobile device). Where the 2D images are received by image capture, a reference marker may be provided on the physical 2D images (e.g., on an X-ray film) with known size to effectuate proper scaling. For example, the image captured by the camera may alter the scale of an X-ray image. Accordingly, a reference marker of known dimensions included on the X-ray film may be used to correct for scaling from the image capture. Subsequently or simultaneously, the 2D image may be scaled as described herein using a fiducial marker to account for the arrangements in the imaging environment, thereby producing accurately scaled 2D images.

Using the accurately scaled 2D images, the simulation and planning system may achieve more accurate measurements and refine or condition the simulation model accordingly. The simulation and planning system may use measurements from the scaled 2D images to adjust dimensions of the simulation model, limit the movement of the simulation model (i.e., conditioning), and/or select an implant make, model, and/or size. Based on the implant selection and simulations, the implant planning system may determine a more accurate post-operative range of motion for each implant orientation. Accordingly, precisely scaled images may provide improved assessment and optimization of implant orientation during surgical planning.

In some embodiments, the simulation and planning system may further evaluate various acetabular cup positions. The scaled 2D images as described may provide accurate dimensions and measurements of the patient anatomy including the pelvis. Accordingly, in addition to evaluation of acetabular cup orientations as described, the simulation and planning system may evaluate range of motion for one or more acetabular cup positions. In some embodiments, the simulation and planning system may evaluate range of motion for one or more acetabular cup placements, wherein each placement comprises a position and an orientation. The simulation and planning system may suggest an acetabular cup placement based on the determined range of motion as described herein.

In some embodiments, the simulation and planning system may additionally evaluate one or more sizes of a ball head of an implant component. For example, a range of motion may be affected by the size of the ball head. Accordingly, the simulation and planning system may evaluate range of motion based on one or more sizes of the ball head and select a size based the range of motion. In some embodiments, the simulation and planning system may evaluate range of motion for one or more sets of implant parameters, wherein each set comprises an acetabular cup position, an acetabular cup orientation, and a ball head size. The simulation and planning system may suggest a set of implant parameters based on the determined range of motion as described herein.

In some embodiments, the simulation and planning system may additionally suggest a size of a stem of an implant component and/or a size of an acetabular cup. The scaled 2D images as described may provide accurate dimensions and measurements of the patient anatomy including the pelvis that facilitate evaluation of stem size and/or acetabular cup size. The stem size and the acetabular cup size may be selected based on the dimensions of the patient anatomy and may not affect range of motion.

In some embodiments, the devices, systems and methods described herein may be used in conjunction with a bone modeling system, an implant planning system, and/or a simulation system as part of a unified approach. For example, the dual scale calibration device 900 may be used during imaging, and the resulting 2D images may be scaled and used with a bone modeling system as described herein to produce a precisely scaled three-dimensional bone model. Further, the scaled 2D images and/or the three-dimensional bone model may be used by an implant planning system as described herein to predict suitable implant parameters (i.e., make, model, and/or size) for the patient. Further, the scaled 2D images, the three-dimensional bone model, and/or the predicted implant parameters may be used by a simulation system to condition a simulation model in accordance with the conditions of the patient and evaluate the range of motion for one or more implant orientations. Accordingly, the use of the devices, systems, and methods described herein may yield scaled 2D images that provide anatomical information for use by a combination of tools to holistically plan an arthroplasty procedure. For example, the scaled 2D images may be used by a bone modeling system to generate an accurate three-dimensional model of the patient anatomy as described. The three dimensional model and information associated therewith (e.g., various dimensions, measurements, geometries, and the like) may be used by the simulation system to produce an accurate simulation model that accounts for the specific anatomy of the patient. Further, the implant planning system may predict an implant size that may be suitable for the patient and the implant information may be incorporated into the simulation model. Finally, the simulation model may evaluate various implant parameters as described to generate an optimal surgical plan including but not limited to acetabular cup position, acetabular cup orientation, and/or ball head size.

In some embodiments, the implant planning system may be used as a redundant calculation to validate the plan. For example, the scaled 2D images may be used by a bone modeling system to generate an accurate three-dimensional model of the patient anatomy and the simulation system may use the information from the three-dimensional model to produce an accurate simulation model that accounts for the specific anatomy of the patient. An implant size may also be selected based on the scaled 2D images by one or more of the bone modeling system and the simulation system. In some cases, an implant size may also be selected according to user input based on assessment of the scaled 2D images. Separately, an implant planning system as described may be used to predict an implant size based on demographic information (i.e., without using information from the scaled 2D images. The predicated implant size from the implant planning system may be compared to the selected implant size to validate the selection. In some embodiments, a selected implant size within one size of the predicted implant size may be sufficient to provide confidence in the selected implant size and the overall surgical plan. Where a greater deviation exists between the selected implant size and the predicted implant size, the system may draw attention to this discrepancy for the user to further assess the selection. In some embodiments, a large deviation may indicate issues or errors with the capture of the 2D images and therefore the surgical plan may require re-assessment. In some embodiments, a large deviation may indicate an "abnormal" patient for which the predicated implant size is inaccurate because the patient's anatomy does not closely align with overall expectations based on demographic information and thus the surgical plan may nonetheless be suitable for the patient.

The devices, systems, and methods described herein represent a significant advancement over conventional fiducial marker systems and calibration methods associated therewith. As described, the technical solution presented herein does not require a secondary marker, thereby allowing patients to be positioned on a standard cushion while laying down, which may result in greater patient comfort. Furthermore, the described methods may calculate a calibration factor with increased accuracy by accounting for projectional effects. Additionally, the calibration factor calculated by the method herein may have increased accuracy by accounting for rotational effects associated with the orientation of the patient during imaging. Accordingly, the methods herein enable correction of various errors or inconsistencies that may occur during imaging due to a variety of factors. Thus, the reliance on imaging technicians and other medical professionals to generate pristine medical images according to precise instructions is somewhat relieved by the correction methods herein.

Nonetheless, in some embodiments, one or more features of the present disclosure may be implemented with a conventional fiducial marker system. For example, a conventional fiducial marker may be positioned on the ventral surface of the patient during imaging according to the method herein, and the resulting 2D images may be scaled using the methods described herein. In another example, the dual scale calibration device may be positioned on the patient during imaging as described herein, and the resulting 2D images may be scaled using conventional methods. In another example, the dual scale calibration device may be secured to the patient in the manner of conventional systems, e.g., an articulating arm and/or a strap extending from a base board, and 2D images may be captured and scaled by the methods described herein. In another example, a conventional multi-fiducial marker system may be used during imaging and the anterior and posterior fiducial markers may be used to identify a distance between the ventral and dorsal surfaces of the patient. Thereafter, the resulting 2D images may be scaled using the methods described herein. It should be understood that other features of the present disclosure may be implemented, individually or in combination, in conventional systems and methods as would be apparent to a person having an ordinary level of skill in the art.

The devices, systems, and methods as described herein are not intended to be limited in terms of the particular embodiments described, which are intended only as illustrations of various features. Many modifications and variations to the devices, systems, and methods can be made without departing from their spirit and scope, as will be apparent to those skilled in the art.

Data Processing Systems for Implementing Embodiments Herein

Figure 22:
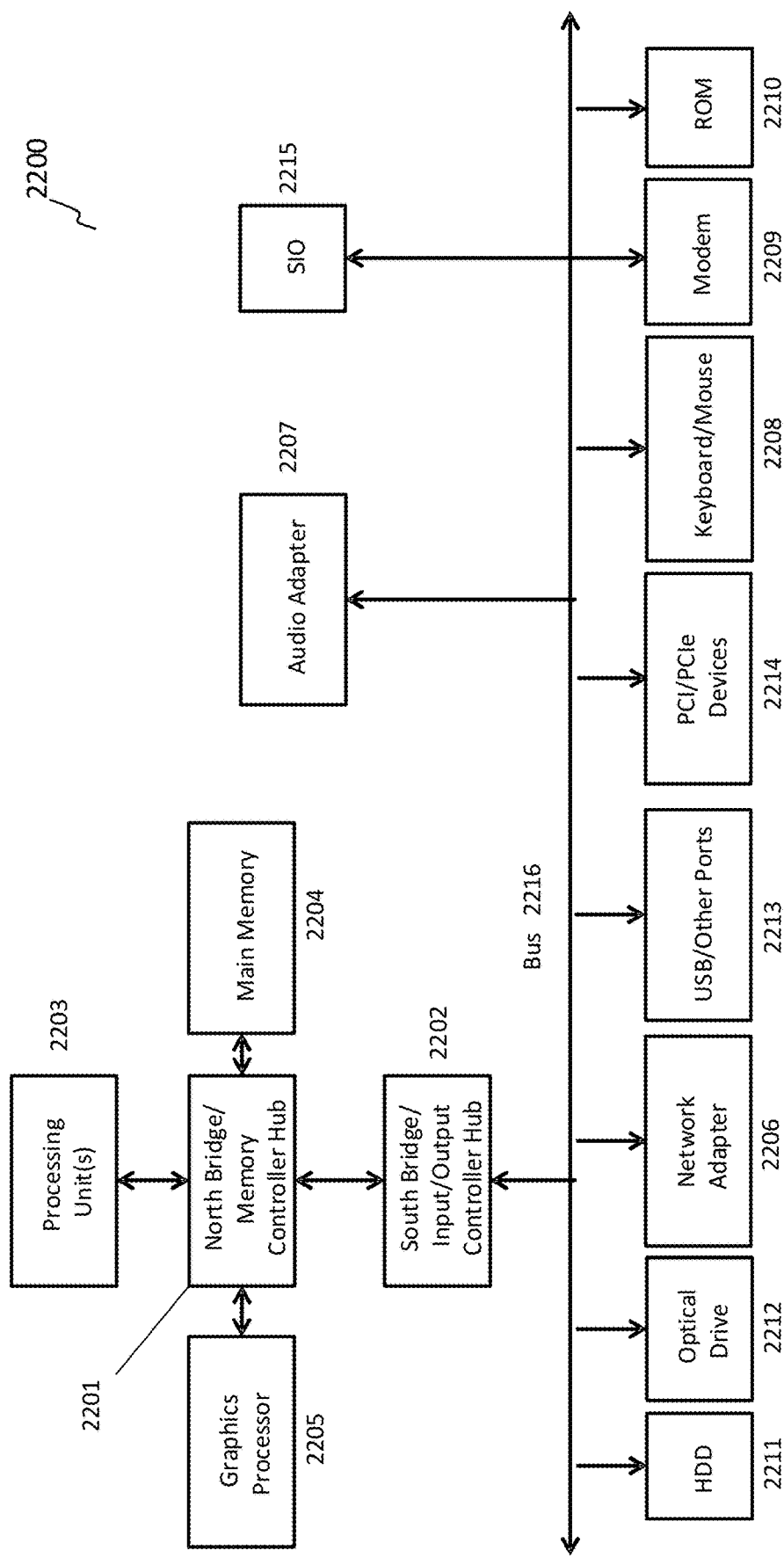
FIG. 22 illustrates a block diagram of an illustrative data processing system in which features of the illustrative embodiments are implemented.

FIG. 22 illustrates a block diagram of an exemplary data processing system 2200 in which embodiments are implemented. The data processing system 2200 is an example of a computer, such as a server or client, in which computer usable code or instructions implementing the process for illustrative embodiments of the present invention are located. In some embodiments, the data processing system 2200 may be a server computing device. For example, data processing system 2200 can be implemented in a server or another similar computing device operably connected to a surgical system 100 as described above. The data processing system 2200 can be configured to, for example, transmit and receive information related to a patient and/or a related surgical plan with the surgical system 100.

In the depicted example, data processing system 2200 can employ a hub architecture including a north bridge and memory controller hub (NB/MCH) 2201 and south bridge and input/output (I/O) controller hub (SB/ICH) 2202. Processing unit 2203, main memory 2204, and graphics processor 2205 can be connected to the NB/MCH 2201. Graphics processor 2205 can be connected to the NB/MCH 2201 through, for example, an accelerated graphics port (AGP).

In the depicted example, a network adapter 2206 connects to the SB/ICH 2202. An audio adapter 2207, keyboard and mouse adapter 2208, modem 2209, read only memory (ROM) 2210, hard disk drive (HDD) 2211, optical drive (e.g., CD or DVD) 2212, universal serial bus (USB) ports and other communication ports 2213, and PCI/PCIe devices 2214 may connect to the SB/ICH 2202 through bus system 2216. PCI/PCIe devices 2214 may include Ethernet adapters, add-in cards, and PC cards for notebook computers. ROM 2210 may be, for example, a flash basic input/output system (BIOS). The HDD 2211 and optical drive 2212 can use an integrated drive electronics (IDE) or serial advanced technology attachment (SATA) interface. A super I/O (SIO) device 2215 can be connected to the SB/ICH 2202.

An operating system can run on the processing unit 2203. The operating system can coordinate and provide control of various components within the data processing system 2200. As a client, the operating system can be a commercially available operating system. An object-oriented programming system, such as the Java™ programming system, may run in conjunction with the operating system and provide calls to the operating system from the object-oriented programs or applications executing on the data processing system 2200. As a server, the data processing system 2200 can be an IBM® eServer™ System® running the Advanced Interactive Executive operating system or the Linux operating system. The data processing system 2200 can be a symmetric multiprocessor (SMP) system that can include a plurality of processors in the processing unit 2203. Alternatively, a single processor system may be employed.

Instructions for the operating system, the object-oriented programming system, and applications or programs are located on storage devices, such as the HDD 2211, and are loaded into the main memory 2204 for execution by the processing unit 2203. The processes for embodiments described herein can be performed by the processing unit 2203 using computer usable program code, which can be located in a memory such as, for example, main memory 2204, ROM 2210, or in one or more peripheral devices.

A bus system 2216 can be comprised of one or more busses. The bus system 2216 can be implemented using any type of communication fabric or architecture that can provide for a transfer of data between different components or devices attached to the fabric or architecture. A communication unit such as the modem 2209 or the network adapter 2206 can include one or more devices that can be used to transmit and receive data.

Those of ordinary skill in the art will appreciate that the hardware depicted in FIG. 22 may vary depending on the implementation. Other internal hardware or peripheral devices, such as flash memory, equivalent non-volatile memory, or optical disk drives may be used in addition to or in place of the hardware depicted. Moreover, the data processing system 2200 can take the form of any of a number of different data processing systems, including but not limited to, client computing devices, server computing devices, tablet computers, laptop computers, telephone or other communication devices, personal digital assistants, and the like. Essentially, data processing system 2200 can be any known or later developed data processing system without architectural limitation.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is also to be understood that the terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices also can "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A computer-implemented method of calibrating a frontal 2D image of a pelvis of a patient positioned on an imaging surface, the method comprising:
   receiving a frontal 2D image of the pelvis captured by an imaging detector, wherein the frontal 2D image comprises a first representation of a fiducial marker positioned on a suprapubic region of the patient during capture;
   measuring a diameter of the first representation of the fiducial marker in the frontal 2D image;
   determining, based on the diameter of the first representation and a known diameter of the fiducial marker, a first distance of the fiducial marker from the imaging detector;
   receiving a lateral 2D image of the pelvis, wherein the lateral 2D image comprises a second representation of the fiducial marker positioned on the suprapubic region of the patient during capture;
   measuring a diameter of the second representation of the fiducial marker in the lateral 2D image;
   determining, based on the diameter of the second representation and the known diameter of the fiducial marker, a second distance of the fiducial marker from a coronal plane of the pelvis in the lateral 2D image;
   correcting the second distance based on a rotational offset of the patient in the lateral 2D image;
   calculating, based on the first distance and the corrected second distance, a third distance of the coronal plane from the imaging detector in the frontal 2D image;
   calculating, based on the third distance, a calibration factor for the frontal 2D image;
   scaling the frontal 2D image based on the calibration factor; and
   outputting the scaled frontal 2D image to a computer-readable storage device.

2. The computer-implemented method of claim 1, wherein calculating the third distance comprises subtracting the corrected second distance from the first distance.

3. The computer-implemented method of claim 1, wherein correcting the second distance comprises:
   measuring a lateral offset of a center of the first representation from a central beam in the frontal 2D image;
   calculating an angle of the rotational offset based on the frontal 2D image and the lateral 2D image;
   calculating an adjustment distance based on the lateral offset and the angle; and
   adjusting the second distance by the adjustment distance to correct the second distance.

4. The computer-implemented method of claim 3, wherein calculating an angle of the rotational offset comprises:
   determining a hip-to-hip distance in the frontal 2D image;
   determining a projected hip-to-hip distance in the lateral 2D image; and
   calculating the angle based on the hip-to-hip distance and the projected hip-to-hip distance.

5. The computer-implemented method of claim 3, wherein correcting the second distance further comprises determining a direction of the rotational offset based on one or more of the frontal 2D image and the lateral 2D image.

6. The computer-implemented method of claim 5, wherein determining a direction of the rotational offset comprises assessing a size of one or more features of the pelvis in the lateral 2D image.

7. The computer-implemented method of claim 5, wherein determining a direction of the rotational offset comprises identifying one or more anatomical abnormalities associated with a hip joint of the pelvis.

8. The computer-implemented method of claim 5, wherein determining a direction of the rotational offset comprises identifying one or more foreign bodies associated with a hip joint of the pelvis.

9. The computer-implemented method of claim 5, wherein determining a direction of the rotational offset comprises assessing a representation of one or more directional markers in the one or more of the frontal 2D image and the lateral 2D image, wherein the one or more directional markers are positioned on the patient during capture.

10. The computer-implemented method of claim 9, wherein the one or more directional markers are positioned on a portion of the pelvis of the patient.

11. The computer-implemented method of claim 9, wherein the one or more directional markers are positioned on or near an anterior superior iliac spine of the pelvis.

12. The computer-implemented method of claim 9, wherein the one or more directional markers are coupled to the fiducial marker.

13. The computer-implemented method of claim 3, wherein adjusting the second distance by the adjustment distance comprises subtracting the adjustment distance from the second distance.

14. The computer-implemented method of claim 3, wherein adjusting the second distance by the adjustment distance comprises adding the adjustment distance to the second distance.

15. The computer-implemented method of claim 1, wherein determining the first distance comprises:
measuring a lateral offset of a center of the first representation from a central beam in the frontal 2D image; and
calculating the first distance based on the lateral offset, the diameter of the first representation, and the known diameter of the fiducial marker.

16. The computer-implemented method of claim 1, wherein determining the second distance comprises:
measuring a lateral offset of a center of the second representation from a central beam in the lateral 2D image; and
calculating the second distance based on the lateral offset, the diameter of the second representation, and the known diameter of the fiducial marker.

17. The computer-implemented method of claim 1, wherein the frontal 2D image is an anterior-posterior 2D image of the hip joint of the patient.

18. A system for calibration of a 2D image of a hip of a patient, the system comprising:
a calibration device comprising:
a belt configured to be positioned about a waist of the patient; and
a single fiducial marker coupled to the belt, where the single fiducial marker is configured to be positioned on the suprapubic region of the patient;
at least one processor; and
a non-transitory, computer-readable medium storing instructions that, when executed, cause the at least one processor to:
receive a frontal 2D image of the pelvis captured by an imaging detector, wherein the frontal 2D image comprises a first representation of a fiducial marker positioned on a suprapubic region of the patient during capture;
measure a diameter of the first representation of the fiducial marker in the frontal 2D image;
determine, based on the diameter of the first representation and a known diameter of the fiducial marker, a first distance of the fiducial marker from the imaging detector;
receive a lateral 2D image of the pelvis, wherein the lateral 2D image comprises a second representation of the fiducial marker positioned on the suprapubic region of the patient during capture;
measure a diameter of the second representation of the fiducial marker in the lateral 2D image;
determine, based on the diameter of the second representation and the known diameter of the fiducial marker, a second distance of the fiducial marker from a coronal plane of the pelvis in the lateral 2D image;
correct the second distance based on a rotational offset of the patient in the lateral 2D image;
calculate, based on the first distance and the corrected second distance, a third distance of the coronal plane from the imaging detector in the frontal 2D image;
calculate, based on the third distance, a calibration factor for the frontal 2D image;
scale the frontal 2D image based on the calibration factor; and
output the scaled frontal 2D image to a computer-readable storage device.

19. The system of claim 18, wherein the instructions that cause the at least one processor to correct the second distance comprise instructions that, when executed, cause the at least one processor to:
measure a lateral offset of a center of the first representation from a central beam in the frontal 2D image;
calculate an angle of the rotational offset based on the frontal 2D image and the lateral 2D image;
calculate an adjustment distance based on the lateral offset and the angle; and
adjust the second distance by the adjustment distance to correct the second distance.

20. The system of claim 19, wherein the instructions that cause the at least one processor to calculate an angle of the rotational offset comprise instructions that, when executed, cause the at least one processor to:
determine a hip-to-hip distance in the frontal 2D image;
determine a projected hip-to-hip distance in the lateral 2D image; and
calculate the angle based on the hip-to-hip distance and the projected hip-to-hip distance.

21. The system of claim 19, wherein the instructions that cause the at least one processor to correct the second distance further comprise instructions that, when executed, cause the at least one processor to determine a direction of the rotational offset based on one or more of the frontal 2D image and the lateral 2D image.

* * * * *